US008889691B2

(12) United States Patent
Kim et al.

(10) Patent No.: US 8,889,691 B2
(45) **Date of Patent: *Nov. 18, 2014**

(54) INDOLE COMPOUNDS AS AN INHIBITOR OF CELLULAR NECROSIS

(71) Applicant: LG Life Sciences Ltd., Seoul (KR)

(72) Inventors: Soon Ha Kim, Daejeon (KR); Hyoung Jin Kim, Daejeon (KR); Sun Young Koo, Daejeon (KR); Sung Bae Lee, Daejeon (KR); Heui Sul Park, Daejeon (KR); Seung Hyun Yoon, Daejeon (KR); Seung Yup Paek, Daejeon (KR); Hyo Shin Kwak, Daejeon (KR); Dong Ook Seo, Daejeon (KR); Eok Park, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/034,234

(22) Filed: Sep. 23, 2013

(65) Prior Publication Data

US 2014/0024618 A1 Jan. 23, 2014

Related U.S. Application Data

(60) Continuation of application No. 13/493,045, filed on Jun. 11, 2012, now Pat. No. 8,569,307, which is a division of application No. 12/671,180, filed as application No. PCT/KR2008/004783 on Aug. 18, 2008, now Pat. No. 8,222,414.

(30) Foreign Application Priority Data

Aug. 17, 2007 (KR) ........................ 10-2007-0082687

(51) Int. Cl.

| | |
|---|---|
| ***A61K 31/496*** | (2006.01) |
| ***A61K 31/541*** | (2006.01) |
| ***C07D 413/14*** | (2006.01) |
| ***A61K 31/445*** | (2006.01) |
| ***A61K 31/4439*** | (2006.01) |
| ***A61K 45/06*** | (2006.01) |
| ***A61K 31/4545*** | (2006.01) |
| ***A61K 31/427*** | (2006.01) |
| ***C07D 417/14*** | (2006.01) |
| ***A61K 31/5377*** | (2006.01) |
| ***C07F 9/6558*** | (2006.01) |
| ***C07D 487/04*** | (2006.01) |
| ***A61K 31/404*** | (2006.01) |
| ***C07D 413/04*** | (2006.01) |
| ***A61K 31/675*** | (2006.01) |
| ***A61K 31/416*** | (2006.01) |
| ***A61K 31/454*** | (2006.01) |
| ***C07D 417/06*** | (2006.01) |
| ***A61K 31/497*** | (2006.01) |
| ***C07D 417/04*** | (2006.01) |

(52) U.S. Cl.

CPC ............ *C07D 417/06* (2013.01); *A61K 31/541* (2013.01); *C07D 413/14* (2013.01); *A61K 31/496* (2013.01); *A61K 31/445* (2013.01); *A61K 31/4439* (2013.01); *A61K 45/06* (2013.01); *A61K 31/4545* (2013.01); *A61K 31/427* (2013.01); *C07D 417/14* (2013.01); *A61K 31/5377* (2013.01); *C07F 9/65583* (2013.01); *C07D 487/04* (2013.01); *A61K 31/404* (2013.01); *C07D 413/04* (2013.01); *C07F 9/65586* (2013.01); *A61K 31/675* (2013.01); *A61K 31/416* (2013.01); *A61K 31/454* (2013.01); *A61K 31/497* (2013.01); *C07D 417/04* (2013.01)

USPC ..................................... 514/254.02; 544/367

(58) Field of Classification Search

CPC .................................................. A61K 31/496

USPC ..................................... 514/254.02; 544/367

See application file for complete search history.

(56) References Cited

U.S. PATENT DOCUMENTS

| | | | |
|---|---|---|---|
| 7,652,133 | B2 | 1/2010 | Yasuma |
| 2009/0247746 | A1 | 10/2009 | Yasuma et al. |

FOREIGN PATENT DOCUMENTS

| | | | |
|---|---|---|---|
| EP | 0676967 | A1 | 9/1995 |
| WO | WO 95/07276 | A1 | 3/1995 |
| WO | WO 2004/018428 | A1 | 3/2004 |
| WO | WO 2006/112549 | A1 | 10/2006 |

OTHER PUBLICATIONS

KIPO International Preliminary Report on Patentability for Appl. No. PCT/KR2008/004783 dated Nov. 5, 2009.

KIPO International Search Report for Appl. No. PCT/KR2008/004783 dated Jan. 22, 2009.

Kubinyi, "3D QSAR in Drug Design: Ligand Protein Interactions and Molecular Similarity," Springer, 1998, vol. 2-3, 800 pages, TOC and pp. 243-44 provided.

Kuramochi et al., "Synthesis and structure-activity relationships of 6-{4-[(3-fluorobenzyl)oxy]phenoxy}nicotinamide derivatives as a novel class of NCX inhibitors: a QSAR study," Bioorganic & Medicinal Chemistry, 2005, vol. 13, pp. 717-724.

Narayana et al., "Synthesis of Some New Biologically Active 1,3,4-oxadiazolylNitroindoles and a Modified Fischer Indole Synthesis of Ethyl Nitro Indole-2-Carboxylates", Bioorganic & Medicinal Chemistry, pp. 4638-4644, vol. 13, No. 15, 2005.

Park et al., "Toxicogenetics in Drug Development," Toxicology Letters, 2001, vol. 120, pp. 281-291.

Wermuth, "The Practice of Medicinal Chemistry", 2d ed., 2003, 768 pages, Chapters 9-10 provided.

Yasuma et al. (CAPLUS Abstract of WO 2006/112549).

*Primary Examiner* — Robert Havlin

(74) *Attorney, Agent, or Firm* — Birch, Stewart, Kolasch & Birch, LLP

(57) ABSTRACT

The present invention relates to new indole compounds, pharmaceutically acceptable salts or isomers thereof which are useful for the prevention or treatment of cellular necrosis and necrosis-associated diseases. The present invention also relates to a method and a composition for the prevention or treatment of cellular necrosis and necrosis-associated diseases, comprising said indole compounds as an active ingredient.

8 Claims, No Drawings

INDOLE COMPOUNDS AS AN INHIBITOR OF CELLULAR NECROSIS

CROSS-REFERENCE TO RELATED APPLICATIONS

This application is a Continuation of U.S. application Ser. No. 13/493,045 filed on Jun. 11, 2012, which is a Divisional of U.S. application Ser. No. 12/671,180 filed Jan. 28, 2010, which issued as U.S. Pat. No. 8,222,414 on Jul. 17, 2012, which is the National phase of PCT International Application No. PCT/KR2008/004783 filed on Aug. 18, 2008. This application also claims priority to Patent Application No. 10-2007-0082687 filed in the Republic of Korea on Aug. 17, 2007. All of the above applications are hereby expressly incorporated by reference into the present application.

TECHNICAL FIELD

The present invention relates to indole compounds of formula (I), pharmaceutically acceptable salts or isomers thereof, and method and composition for the prevention or treatment of cellular necrosis and necrosis-associated diseases comprising the same as an active ingredient.

BACKGROUND ART

Most researches associated with cell death have been concentrated on apoptosis of cells, also known as programmed cell death (PCD). With the discovery of the enzyme caspase, a number of pharmaceutical companies have promoted the development of drugs utilizing caspase inhibitors during the past 10 years. However, the current status is that there have hardly been any of these drugs approved by FDA. This is because the apoptosis of cells is a cell death which occurs under physiological circumstances and such a cell death may be probably due to the defense mechanism for maintaining homeostasis in the body. In contrast, necrosis is a cell death which mainly occurs under morbid circumstances, and in most cases it is characterized by accompanying the inflammatory response. Necrosis has been known as an uncontrolled cell death for a long time, but a recent research (Proskurykakov S Y et al. 2002, Biochemistry) reported the necrosis as an active/controlled cell death. Typical diseases caused by necrosis include ischemic (e.g. myocardial infarction, stroke, renal infarction), neurodegenerative, and inflammatory diseases. Since it is believed that necrosis is an uncontrolled, accidental cell death under morbid circumstances, researches on the functional mechanism, molecular targets, signal transduction systems, etc. thereof have rarely been conducted. Thus, there arises a compelling need to discover and develop the necrosis-inhibiting substances for the treatment of ischemic, neurodegenerative, and inflammatory diseases which are caused by necrosis, and to elucidate the biological, pathological causes of necrosis.

The indole derivatives according to the present invention have very useful structures from a medical viewpoint and many publications have reported the research results with reference to these structures. Among the research results, the following are the most representative of all: the patent WO2006/112549 reported some indole derivatives having the activity for the glucokinase, the patent WO95/07276 reported those useful as anti-tumor agents and as inhibitors against the production of cardiovascular system, and the patent WO2004/018428 reported those useful as antibiotics.

DETAILED DESCRIPTION OF THE INVENTION

Technical Subject to be Solved

Thus, the present inventors have extensively studied under the above mentioned technical background to develop new compounds that exhibit an effect of prevention or treatment and amelioration for cellular necrosis and necrosis-associated diseases, particularly useful for the prevention or treatment of hepatic diseases. As a result thereof, they confirmed that the indole derivatives of formula (I) as explained below show a superior effect for the prevention and treatment of cellular necrosis and necrosis-associated diseases, whereby completed the present invention.

Therefore, it is an object of the present invention to provide new indole derivatives of formula (I).

It is another object of the present invention to provide a composition for the prevention or treatment of cellular necrosis and necrosis-associated diseases, in particular, for hepatoprotection, hepatic functional improvement, and prevention or treatment of acute/chronic hepatic diseases, which comprises as an active ingredient the compounds of formula (I), pharmaceutically acceptable salts or isomers thereof together with a pharmaceutically acceptable carrier or diluent, and process for preparing the same.

It is still another object of the present invention to provide a method for the prevention or treatment of cellular necrosis and necrosis-associated diseases, in particular, for hepatoprotection, hepatic functional improvement, and prevention or treatment of acute/chronic hepatic diseases using said composition.

Means for Solving the Technical Subject

To accomplish the above objects, the present invention provides indole compounds of the following formula (I):

(1)

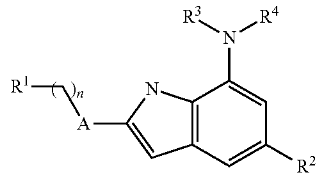

in which n denotes a number of 0 to 3,

A represents 5 membered heteroaryl or heterocycle each of which has 1 to 3 hetero atoms selected from N, O and S, $R^1$ represents $R^5$—X—B—X'—, B represents a direct bond, or represents 3~10 membered heterocycle or heteroaryl each of which has 1 to 4 hetero atoms selected from N, O and S, X and X' independently of one another represent a direct bond, or are selected from the group consisting of —$NR^6$—, —CO—, —$CONR^6$—, —$CO_2$—, —OC(O)—, —$S(O)_m$—, —O—$(CH_2)_m$—, —$(CH_2)_m$—O—, —$(CH_2)_m$—, —$NR^6$CO—, —$(R^6O)_2$P(O)— and —$NHCO_2$—, wherein m denotes a number of 0 to 3, and $R^6$ represents hydrogen, alkyl or cycloalkyl, $R^5$ represents hydrogen, nitrile, hydroxy, alkyl, alkoxy, cycloalkyl or aryl, or represents 3~10 membered monocyclic or fused cyclic heterocycle or heteroaryl each of which has 1 to 3 hetero atoms selected from N, O and S, and is optionally substituted by oxo or alkyl, or $R^5$ and $R^6$ may together form a 4~8 membered cycle, $R^2$ represents —$(CR^8R^9)_p$—Y—$R^7$, p denotes a number of 0 to 2, $R^8$ and $R^9$ independently of one another represent hydrogen or alkyl, or may together form a 4~8 membered cycle, Y represents a direct bond, or is selected from the group consisting of —O—, —S—, —$NR^6$—, —$NR^6C(O)$—, —$CO_2$—, —C(O)—, —$C(O)NR^6$—, —$S(O)_q$—, and —$S(O)_qNR^6$—, wherein q denotes a number of 0 to 2, $R^7$ represents hydrogen, halogen, cyano, hydroxy, nitro, alkyl, cycloalkyl or aryl, or represents 3~10 membered heterocycle or heteroaryl each of which has 1 to 3 hetero atoms selected from N, S and O and which optionally contains oxo, $R^3$ represents hydrogen, alkyl, —$(CH_2)_q$-cycloalkyl or —$(CH_2)_q$-heterocycle, $R^4$ represents —$(CH_2)_p$-D-$R^{10}$, D represents a direct bond, represents cycloalkyl optionally containing oxo, represents aryl, or represents 3~10 membered heterocycle or heteroaryl each of which has 1 to 3 hetero atoms selected from N, S and O, $R^{10}$ represents hydrogen, halogen, amino, cyano, nitro, hydroxy, alkyl, alkylcarbonyl, alkylsulfonyl or —$(CH_2)_p$—$NR^8R^9$, where alkyl, alkoxy, aryl, cycloalkyl, heterocycle and heteroaryl may be optionally substituted, and the substituents are one or more selected from the group consisting of hydroxy, halogen, nitrile, amino, alkylamino, dialkylamino, alkyl, haloalkyl, alkylsulfonyl, carboxyalkyl, alkylcarbonyloxy, alkylthio, alkyloxycarbonyl, alkylaminocarbonyl, arylalkoxy and oxo, and pharmaceutically acceptable salts or isomers thereof.

In the above definitions for the compounds of formula (I), the term 'alkyl' means an aliphatic hydrocarbon radical. Alkyl may be saturated alkyl that does not comprise alkenyl or alkynyl moiety, or unsaturated alkyl that comprises at least one alkenyl or alkynyl moiety. "Alkenyl" means a group containing at least one carbon-carbon double bond, and "alkynyl" means a group containing at least one carbon-carbon triple bond. Alkyl may be branched or straight-chain when used alone or in a composite form such as alkoxy.

Alkyl group may have 1 to 20 carbon atoms unless otherwise defined. Alkyl group may be a medium sized alkyl having 1 to 10 carbon atoms. Otherwise, alkyl group may be a lower alkyl having 1 to 6 carbon atoms. Typical examples thereof include, but not limited to, methyl, ethyl, propyl, isopropyl, n-butyl, isobutyl, t-butyl, pentyl, hexyl, ethenyl, propenyl, butenyl, etc. For example, $C_1$-$C_4$-alkyl has 1 to 4 carbon atoms in the alkyl chain, and is selected from the group consisting of methyl, ethyl, propyl, isopropyl, n-butyl, isobutyl, sec-butyl and t-butyl.

The term 'alkoxy' means an alkyloxy having 1 to 10 carbon atoms unless otherwise defined.

The term 'cycloalkyl' means a saturated aliphatic 3~10 membered cycle unless otherwise defined. Typical examples thereof include, but not limited to, cyclopropyl, cyclobutyl, cyclopentyl, cyclohexyl, etc.

The term 'aryl' include at least one ring having covalent it electron system, for example, monocyclic or fused polycyclic (i.e., cycles that share the adjacent carbon atom pairs) groups. In the present specification, aryl means an aromatic 4~10 membered, preferably 6~10 membered, monocyclic or multicyclic ring including phenyl, naphthyl, etc., unless otherwise defined.

The term 'heteroaryl' means an aromatic 3~10 membered, preferably 4~8 membered, more preferably 5~6 membered cycle that has 1 to 4 hetero atoms selected from N, O and S, and may be fused with benzo or $C_3$-$C_8$ cycloalkyl, unless otherwise defined. The monocyclic heteroaryl includes, but not limited to, thiazole, oxazole, thiophene, furan, pyrrole, imidazole, isoxazole, isothiazole, pyrazole, triazole, triazine, thiadiazole, tetrazole, oxadiazole, pyridine, pyridazine, pyrimidine, pyrazine and the like. The bicyclic heteroaryl includes, but not limited to, indole, indoline, benzothiophene, benzofuran, benzimidazole, benzoxazole, benzisoxazole, benzthiazole, benzthiadiazole, benztriazole, quinoline, isoquinoline, purine, puropyridine and the like.

The term 'heterocycle' means a 3~10 membered, preferably 4~8 membered, more preferably 5~6 membered cycle that has 1 to 4 hetero atoms selected from N, O and S, may be fused with benzo or $C_3$-$C_8$ cycloalkyl, and is saturated or contains 1 or 2 double bonds, unless otherwise defined. The heterocycle includes, but not limited to, pyrroline, pyrrolidine, imidazoline, imidazolidine, pyrazoline, pyrazolidine, pyran, piperidine, morpholine, thiomorpholine, piperazine, hydrofuran and the like.

Other terms and abbreviations in the present specification may be understood to have the meaning conventionally used in this field by a skilled artisan, unless otherwise defined.

Preferred compounds among the compounds of formula (I) above are those wherein n denotes a number of 0 to 3, A represents 5 membered heteroaryl or heterocycle each of which has 1 to 3 hetero atoms selected from N, O and S, $R^1$ represents $R^5$—X—B—X'—, B represents a direct bond, or represents 3~10 membered heterocycle or heteroaryl each of which has 1 to 4 hetero atoms selected from N, O and S, X and X' independently of one another represent a direct bond, or are selected from the group consisting of —$NR^6$—, —CO—, —$CONR^6$—, —$CO_2$—, —OC(O)—, —$S(O)_2$—, —O—$(CH_2)_m$—, —$(CH_2)_m$—O—, —$(CH_2)_m$—, —$NR^6CO$—, —$(R^6O)_2P(O)$— and —$NHCO_2$—, wherein m denotes a number of 0 to 3, and $R^6$ represents hydrogen, $C_1$-$C_6$-alkyl or $C_3$-$C_6$-cycloalkyl, $R^5$ represents hydrogen, nitrile, hydroxy, $C_1$-$C_6$-alkyl, halogeno-$C_1$-$C_6$-alkyl, hydroxy-$C_1$-$C_6$-alkyl, $C_4$-$C_6$-cycloalkyl, phenyl or halophenyl, or represents 5~10 membered monocyclic or fused cyclic heterocycle or heteroaryl each of which has 1 to 3 hetero atoms selected from N, O and S, and is optionally substituted by oxo or halogeno-$C_1$-$C_6$-alkyl, or $R^5$ and $R^6$ may together form a 4~8 membered cycle, $R^2$ represents —$(CR^8R^9)_p$—Y—$R^7$, p denotes a number of 0 to 2, $R^8$ and $R^9$ independently of one another represent hydrogen or $C_1$-$C_6$-alkyl, or may together form a 5~6 membered cycle, Y represents a direct bond, or is selected from the group consisting of —O—, —$NR^6$—, —$NR^6C(O)$—, —C(O)—, —$CO_2$—, —$C(O)NR^6$—, and —$S(O)_q$—, wherein q denotes a number of 0 to 2, $R^7$ represents hydrogen, halogen, cyano, hydroxy, $C_1$-$C_6$-alkyl, hydroxy-$C_1$-$C_6$-alkyl or halogeno-$C_1$-$C_6$-alkyl, represents phenyl optionally substituted by $C_1$-$C_6$-alkylsulfonyl, or represents 5~6 membered heterocycle or heteroaryl each of which has 1 to 3 hetero atoms selected from N and O, $R^3$ represents hydrogen, $C_1$-$C_6$-alkyl, —$(CH_2)$—$C_3$-$C_6$-cycloalkyl or —$(CH_2)$— heterocycle wherein the heterocycle is a 5~6 membered cycle having 1 to 2 hetero atoms selected from N, O and S, $R^4$ represents —$(CH_2)_p$-D-$R^{10}$, D represents a direct bond, represents $C_3$-$C_6$-cycloalkyl optionally containing oxo, or represents 5~6 membered heterocycle or heteroaryl each of which has 1 to 2 hetero atoms selected from N, O and S, $R^{10}$ represents hydrogen, halogen, amino, $C_1$-$C_6$-alkyl, $C_1$-$C_6$-alkylcarbonyl, halogeno-$C_1$-$C_6$-alkylcarbonyl, $C_1$-$C_6$-alkylsulfonyl or $-(CH_2)_p-NR^8R^9$.

In the compounds of formula (I) according to the present invention, A more preferably represents a cycle that can be represented by one of the following formulae (i) to (viii), wherein R represents hydrogen, or represents $C_1$-$C_4$-alkyl optionally substituted by hydroxy or amino.

(i)

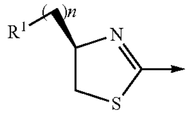

(ii)

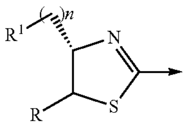

(iii)

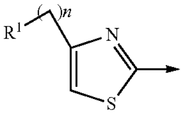

(iv)

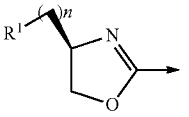

(v)

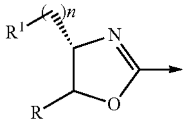

(vi)

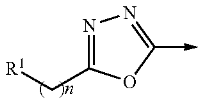

(vii)

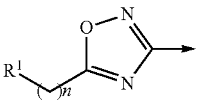

(viii)

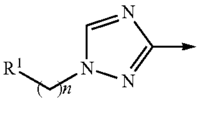

A is most preferably selected from the group consisting of 4,5-dihydro-thiazole, thiazole, oxazoline, oxadiazole and isoxadiazole.

In the formula $R^5-X-B-X'-$ of $R^1$, B more preferably represents a direct bond, represents imidazole or oxadiazole, or represents a 5~6 membered heterocycle having 1 to 2 hetero atoms selected from N and O, and most preferably represents a structure that can be represented by one of the following formulae (ix) to (xii).

(ix)

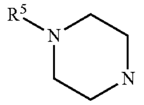

(x)

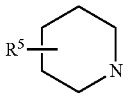

(xi)

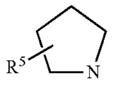

(xii)

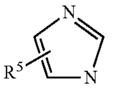

X more preferably represents a direct bond, or is selected from the group consisting of $-CO-$, $-CONR^6-$, $-CO_2-$, $-SO_2-$, $-(CH_2)_m-$, and $-O-(CH_2)_m-$, wherein m denotes a number of 0 to 2, and $R^6$ represents hydrogen, $C_1$-$C_6$-alkyl or $C_3$-$C_6$-cycloalkyl. Most preferably, X is selected from the group consisting of $-CO-$, $-CONH-$, $-CO_2-$, $-SO_2-$, $-(CH_2)_2-$, $-O-$ and $-O-CH_2-$.

X' more preferably represents a direct bond, or is selected from the group consisting of $-(CH_2)_2-$, $-NH-$, $-CO-$, $-CO_2-$, $-CONH-$, $-S(O)_2-$, $-(R^6O)_2P(O)-$, $-NHC(O)-$ and $-NHCO_2-$.

$R^5$ more preferably represents hydrogen, nitrile, hydroxy, $C_1$-$C_6$-alkyl, halogeno-$C_1$-$C_6$-alkyl, hydroxy-$C_1$-$C_6$-alkyl, $C_4$-$C_6$-cycloalkyl, phenyl or halophenyl, or represents mono-cyclic or fused cyclic 5~9 membered heterocycle or 5~6 membered heteroaryl each of which has 1 to 3 hetero atoms selected from N, O and S, and is optionally substituted by oxo or trifluoromethyl. Most preferably, $R^5$ is selected from the group consisting of hydrogen, nitrile, hydroxy, methyl, ethyl, isopropyl, isobutyl, hydroxymethyl, trifluoromethyl, cyclobutyl, cyclopentyl, cyclohexyl, pyrrolidine, piperidine, 2-oxopiperazine, 2-oxopyrrolidine, tetrahydrofuran, tetrahydropyran, tetrahydrothiopyran, morpholine, furan, pyridine, 1,3-pyrazine, 1,1-dioxo-thiomorpholine, tetrazole, imidazole, pyrazole and 3-trifluoromethyl-5,6,7,8-tetrahydro-2H-[1,2,4]triazolo[4,3-a]pyrazine.

In the formula $-(CR^8R^9)_p-Y-R^7$ of $R^2$, $R^8$ and $R^9$ each more preferably represent hydrogen.

Y is more preferably selected from the group consisting of $-O-$, $-NR^6-$, $-NR^6C(O)-$, $-C(O)-$, $-C(O)NR^6-$, and $-S(O)_2-$, wherein $R^6$ is as defined in the above preferable scope. Most preferably, Y is selected from group consisting of $-O-$, $-NH-$, $-NHC(O)-$, $-SO_2-$, and $-C(O)-$.

$R^7$ more preferably represents hydrogen, halogen, hydroxy, $C_1$-$C_6$-alkyl, hydroxymethyl or halogeno-$C_1$-$C_6$-alkyl, represents phenyl optionally substituted by $C_1$-$C_6$-alkylsulfonyl, or represents 5~6 membered heterocycle or heteroaryl each of which has 1 to 2 hetero atoms selected from N and O. Most preferably, $R^7$ is selected from the group consisting of hydrogen, bromo, fluoro, chloro, methyl, ethyl, propyl, hydroxymethyl, trifluoromethyl, phenyl, 4-methylsulfonyl-phenyl, piperidine, pyrrolidine, furan, pyrrole, pyrazole and pyridine.

$R^3$ more preferably represents hydrogen, methyl or isobutyl.

$R^4$ more preferably represents —$R^{10}$, -D-$R^{10}$ or —$CH_2$-D-$R^{10}$, wherein D represents $C_3$-$C_6$-cycloalkyl optionally containing oxo, represents 5~6 membered heterocycle having 1 to 2 hetero atoms selected from N, O and S, or represents 5~6 membered heteroaryl having 1 to 2 hetero atoms selected from N and S, and $R^{10}$ represents hydrogen, halogen, amino, $C_1$-$C_6$-alkyl, $C_1$-$C_3$-alkylcarbonyl, halogeno-$C_1$-$C_3$-alkylcarbonyl, $C_1$-$C_3$-alkylsulfonyl or —$(CH_2)_p$—$NR^8R^9$, wherein p, $R^8$ and $R^9$ are as defined in the above preferable scope. Most preferably, $R^4$ is selected from the group consisting of hydrogen, isopropyl, isobutyl, cyclopropylmethyl, cyclopentylmethyl, cyclobutyl, cyclopentyl, cyclohexyl, 4-methyl-cyclohexyl, 4,4-difluorocyclohexyl, 4-oxo-cyclohexyl, tetrahydropyran-4-yl, (tetrahydropyran-4-yl)methyl, (tetrahydropyran-2-yl)methyl, tetrahydrofuran-3-yl, piperidin-4-yl, methanesulfonyl, 1-acetyl-piperidin-4-yl, 1-methanesulfonyl-piperidin-4-yl, 1-trifluoroacetyl-piperidin-4-yl, 1-acetyl-pyrrolidin-3-yl, tetrahydrothiopyran-4-yl, thiophen-3-yl and 5-amino-pyridin-2-yl.

The compounds of formula (I) according to the present invention can also form a pharmaceutically acceptable salt. Such a "pharmaceutically acceptable salt" includes non-toxic acid addition salt containing pharmaceutically acceptable anion, for example, a salt with inorganic acids such as sulfuric acid, hydrochloric acid, nitric acid, phosphoric acid, hydrobromic acid, hydriodic acid, etc.; a salt with organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; or a salt with sulfonic acids such as methanesulfonic acid, ethanesulfonic acid, benzenesulfonic acid, p-toluenesulfonic acid, naphthalenesulfonic acid, etc. The compounds of formula (I) can also form a pharmaceutically acceptable base addition salt, for example, a salt with alkali metals or alkaline earth metals such as lithium, sodium, potassium, calcium, magnesium, etc.; a salt with amino acids such as lysine, arginine, guanidine, etc.; or an organic salt with dicyclohexylamine, N-methyl-D-glucamine, tris(hydroxymethyl)methylamine, diethanolamine, choline, triethylamine, etc. The compounds of formula (I) of the present invention may be converted to their salts according to any of the conventional methods, and the salt formation can be easily carried out by a skilled artisan based on the structure of formula (I) without additional explanations thereon.

The term 'isomer' in the present specification means those having the same chemical or molecular formula as, but optically or sterically different from, the compounds of formula (I), or salts thereof. The compounds of formula (I) of the present invention may have an asymmetric carbon center(s) in the structure, and so may exist in the form of optical isomer (R or S isomer), racemate, mixture of diastereomers, or individual diastereomer, etc. When the compounds have a double bond, they may exist in the form of geometric isomer (trans or cis isomer). All the isomers and their mixtures are also covered by the present invention.

Hereinafter, the compounds of formula (I) include pharmaceutically acceptable salts and isomers thereof, unless otherwise explained. The salts and isomers should be construed to be covered by the present invention. For the sake of convenience, the present specification briefly expresses them as the compounds of formula (I).

Typical compounds among the compounds of formula (I) are those selected from the following:

Cyclopentyl-[2-(4,5-dihydro-1,3-thiazol-2-yl)-1H-indol-7-yl]-amine;

[(R)-2-(7-cyclopentylamino-1H-indol-2-yl)-4,5-dihydro-1,3-thiazol-4-yl]-methanol;

[(R)-2-(5-chloro-7-cyclopentylamino-1H-indol-2-yl)-4,5-dihydro-thiazol-4-yl]-acetic acid methyl ester;

[(R)-2-(5-chloro-7-cyclopentylamino-1H-indol-2-yl)-4,5-dihydro-thiazol-4-yl]-acetic acid;

2-[(R)-2-(5-chloro-7-cyclopentylamino-1H-indol-2-yl)-4,5-dihydro-thiazol-4-yl]-ethanol;

(R)-2-[7-cyclopentylamino-5-(hydroxymethyl)-1H-indol-2-yl]-4,5-dihydro-thiazol-4-yl-methanol;

[2-(4,5-Dihydro-thiazol-2-yl)-1H-indol-7-yl]-piperidin-4-yl-amine;

[(R)-2-(5-methyl-7-(tetrahydropyran-4-yl)methylamino-1H-indol-2-yl)-4,5-dihydro-thiazol-4-yl]-acetic acid;

[(S)-2-(5-methyl-7-(1-trifluoroacetylpiperidin-4-yl)amino-1H-indol-2-yl)-4,5-dihydro-thiazol-4-yl]-acetic acid;

2-[(S)-2-(7-(tetrahydropyran-2-yl)methylamino-1H-indol-2-yl)-4,5-dihydro-thiazol-4-yl]-acetic acid;

[(S)-2-(7-(tetrahydropyran-4-yl)amino-1H-indol-2-yl)-4,5-dihydro-thiazol-4-yl]-acetic acid;

[(S)-2-(7-(tetrahydropyran-4-yl)methylamino-1H-indol-2-yl)-4,5-dihydro-thiazol-4-yl]-acetic acid;

[(S)-2-(5-methyl-7-(1-acetylpyrrolidin-3-yl)amino-1H-indol-2-yl)-4,5-dihydro-thiazol-4-yl]-acetic acid;

[(S)-2-(7-cyclopentylamino-1H-indol-2-yl)-4,5-dihydro-thiazol-4-yl]-acetic acid;

[(R)-2-(5-phenoxy-7-(tetrahydropyran-4-yl)methylamino-1H-indol-2-yl)-4,5-dihydro-thiazol-4-yl]-acetic acid;

[(S)-2-(5-phenoxy-7-(tetrahydropyran-4-yl)amino-1H-indol-2-yl)-4,5-dihydro-thiazol-4-yl]-acetic acid;

[(S)-2-(5-methyl-7-(4,4-difluorocyclohexan-4-yl)amino-1H-indol-2-yl)-4,5-dihydro-thiazol-4-yl]-acetic acid;

[(S)-2-(5-chloro-7-(tetrahydropyran-4-yl)methylamino-1H-indol-2-yl)-4,5-dihydro-thiazol-4-yl]-acetic acid;

[(S)-2-(5-methyl-7-cyclobutylamino-1H-indol-2-yl)-4,5-dihydro-thiazol-4-yl]-acetic acid;

[(S)-2-(5-methyl-7-(tetrahydrofuran-3-yl)-amino-1H-indol-2-yl)-4,5-dihydro-thiazol-4-yl]-acetic acid;

[(S)-2-(5-methyl-7-cyclopropylmethylamino-1H-indol-2-yl)-4,5-dihydro-thiazol-4-yl]-acetic acid;

[(S)-2-(5-methyl-7-(tetrahydropyran-4-yl)methylamino-1H-indol-2-yl)-4,5-dihydro-thiazol-4-yl]-acetic acid;

[(S)-2-(5-methyl-7-cyclopentylmethylamino-1H-indol-2-yl)-4,5-dihydro-thiazol-4-yl]-acetic acid;

[(S)-2-(5-methyl-7-(tetrahydropyran-4-yl)amino-1H-indol-2-yl)-4,5-dihydro-thiazol-4-yl]-ethanol;

[(S)-2-(5-methyl-7-(tetrahydropyran-4-yl)amino-1H-indol-2-yl)-4,5-dihydro-thiazol-4-yl]-acetic acid;

[(S)-2-(5-methyl-7-cyclopentylamino-1H-indol-2-yl)-4,5-dihydro-thiazol-4-yl]-acetic acid;

(Thiophen-3-yl)methyl-[2-(4,5-dihydro-1,3-thiazol-2-yl)-1H-indol-7-yl]-amine;

(3-Tetrahydrofuran)-[2-(4,5-dihydro-1,3-thiazol-2-yl)-1H-indol-7-yl]-amine;

[(R)-2-(7-cyclopentylamino-1H-indol-2-yl)-4,5-dihydro-1,3-thiazol-4-yl]-methanol;

3-[(R)-2-(7-(tetrahydropyran-4-yl)amino-1H-indol-2-yl)-4,5-dihydro-thiazol-4-yl]-propionic acid;

[(R)-2-(5-chloro-7-isopropylamino-1H-indol-2-yl)-4,5-dihydro-1,3-thiazol-4-yl]-methanol;

(Tetrahydropyran-4-yl)-[2-(4,5-dihydro-4-methyl-thiazol-2-yl)-1H-indol-7-yl]-amine;

[(R)-2-(5-(morpholin-4-yl)methyl-7-(tetrahydropyran-4-yl)amino-1H-indol-2-yl)-4,5-dihydro-thiazol-4-yl]-methanol;

[(R)-2-(5-(dimethylamino)methyl-7-cyclopentylamino-1H-indol-2-yl)-4,5-dihydro-thiazol-4-yl]-methanol;

[(R)-2-(5-(pyrrol-3-yl)methyl-7-cyclopentylamino-1H-indol-2-yl)-4,5-dihydro-thiazol-4-yl]-methanol;

[(R)-2-(5-(1,3-imidazol-1-yl)methyl-7-cyclopentylamino-1H-indol-2-yl)-4,5-dihydro-thiazol-4-yl]-methanol;

[(R)-2-(5-(pyrazol-1-yl)methyl-7-cyclopentylamino-1H-indol-2-yl)-4,5-dihydro-thiazol-4-yl]-methanol;

[(R)-2-(5-acetylamino-7-cyclopentylamino-1H-indol-2-yl)-4,5-dihydro-thiazol-4-yl]-methanol;

[(R)-2-(5-phenoxymethyl-7-cyclopentylamino-1H-indol-2-yl)-4,5-dihydro-thiazol-4-yl]-acetic acid;

[(R)-2-(5-(pyrrolidin-1-yl)methyl-7-cyclopentylamino-1H-indol-2-yl)-4,5-dihydro-thiazol-4-yl]-acetic acid methyl ester;

Cyclopentyl-[5-chloro-2-((R)-4-isobutyl-4,5-dihydro-thiazol-2-yl)-1H-indol-7-yl)-amine;

[(R)-2-(7-cyclopentylamino-1H-indol-2-yl)-4,5-dihydro-thiazol-4-yl]-propionic acid ethyl ester;

{(R)-2-[7-((3R)-1-acetylpyrrolidin-3-yl)amino-1H-indol-2-yl]-4,5-dihydro-1,3-thiazol-4-yl}-methanol;

Cyclopentyl-[5-fluoro-2-((R)-4-ethyl-4,5-dihydro-thiazol-2-yl)-1H-indol-7-yl]-amine;

{(R)-2-[7-(methyl-cyclopentyl)amino-5-fluoro-1H-indol-2-yl]-4,5-dihydro-1,3-thiazol-4-yl}-methanol;

[(S)-2-(5-ethoxy-7-cyclopentylamino-1H-indol-2-yl)-4,5-dihydro-thiazol-4-yl]acetic acid methyl ester;

[(S)-2-(5-ethoxy-7-cyclopentylamino-1H-indol-2-yl)-4,5-dihydro-thiazol-4-yl]-acetic acid;

[(S)-2-(5-ethoxy-7-cyclopentylamino-1H-indol-2-yl)-4,5-dihydro-thiazol-4-yl]-ethanol;

[(R)-2-(5-methyl-7-cyclopentylamino-1H-indol-2-yl)-4,5-dihydro-thiazol-4-yl]-carboxylic acid ethyl ester;

[(S)-2-(5-phenoxy-7-cyclopentylamino-1H-indol-2-yl)-4,5-dihydro-thiazol-4-yl]-acetic acid;

[(R)-2-(7-(tetrahydropyran-4-yl)amino-1H-indol-2-yl)-4,5-dihydro-thiazol-4-yl]-methanol;

[(R)-2-(7-(tetrahydrofuran-3-yl)amino-1H-indol-2-yl)-4,5-dihydro-thiazol-4-yl]-methanol;

[(R)-2-(7-(1-(methanesulfonyl)pyrrolidin-3-yl)-amino-1H-indol-2-yl)-4,5-dihydro-thiazol-4-yl]-methanol;

[(R)-2-(5-fluoro-7-cyclopentylamino-1H-indol-2-yl)-4,5-dihydro-thiazol-4-yl]-methanol;

[(R)-2-(5-fluoro-7-(tetrahydropyran-4-yl)amino-1H-indol-2-yl)-4,5-dihydro-thiazol-4-yl]-methanol;

[(R)-2-(5-chloro-7-cyclopentylamino-1H-indol-2-yl)-4,5-dihydro-thiazol-4-yl]-ethanol;

[(R)-2-(5-chloro-7-(tetrahydrothiopyran-4-yl)amino-1H-indol-2-yl)-4,5-dihydro-thiazol-4-yl]-methanol;

[(R)-2-(5-bromo-7-cyclopentylamino-1H-indol-2-yl)-4,5-dihydro-thiazol-4-yl]-methanol;

[(R)-2-(5-bromo-7-(tetrahydropyran-4-yl)-1H-indol-2-yl)-4,5-dihydro-thiazol-4-yl]-methanol;

[(R)-2-(5-methoxy-7-cyclopentylamino-1H-indol-2-yl)-4,5-dihydro-thiazol-4-yl]-methanol;

[(R)-2-(5-(pyridin-3-yl)oxy-7-cyclopentylamino-1H-indol-2-yl)-4,5-dihydro-thiazol-4-yl]-methanol;

[(R)-2-(5-(pyridin-3-yl)oxy-7-(tetrahydropyran-4-yl)amino-1H-indol-2-yl)-4,5-dihydro-thiazol-4-yl]-methanol;

[(R)-2-(5-methanesulfonylmethyl-7-cyclopentylamino-1H-indol-2-yl)-4,5-dihydro-thiazol-4-yl]-methanol;

[(R)-2-(5-(isoindol-1,3-dion-2-yl)methyl-7-cyclopentylamino-1H-indol-2-yl)-4,5-dihydro-thiazol-4-yl]-methanol;

[(R)-2-(5-chloro-7-(tetrahydropyran-4-yl)amino-1H-indol-2-yl)-4,5-dihydro-thiazol-4-yl]-acetic acid methyl ester;

[(R)-2-(5-chloro-7-(tetrahydropyran-4-yl)amino-1H-indol-2-yl)-4,5-dihydro-thiazol-4-yl]-acetic acid;

[(R)-2-(5-chloro-7-(tetrahydropyran-4-yl)amino-1H-indol-2-yl)-4,5-dihydro-thiazol-4-yl]-ethanol;

[(R)-2-(5-bromo-7-cyclopentylamino-1H-indol-2-yl)-4,5-dihydro-thiazol-4-yl]-acetic acid;

[(R)-2-(5-bromo-7-(tetrahydropyran-4-yl)amino-1H-indol-2-yl)-4,5-dihydro-thiazol-4-yl]-ethanol;

[(R)-2-(5-bromo-7-(tetrahydropyran-4-yl)amino-1H-indol-2-yl)-4,5-dihydro-thiazol-4-yl]-acetic acid;

[(R)-2-(5-fluoro-7-cyclopentylamino-1H-indol-2-yl)-4,5-dihydro-thiazol-4-yl]-acetic acid;

[(R)-2-(5-fluoro-7-cyclopentylamino-1H-indol-2-yl)-4,5-dihydro-thiazol-4-yl]-acetic acid ethyl ester;

[(R)-2-(5-fluoro-7-cyclopentylamino-1H-indol-2-yl)-4,5-dihydro-thiazol-4-yl]-ethanol;

[(R)-2-(5-fluoro-7-(tetrahydropyran-4-yl)amino-1H-indol-2-yl)-4,5-dihydro-thiazol-4-yl]-acetic acid;

[(R)-2-(7-cyclopentylamino-1H-indol-2-yl)-4,5-dihydro-thiazol-4-yl]-acetic acid;

[(R)-2-(7-cyclopentylamino-1H-indol-2-yl)-4,5-dihydro-thiazol-4-yl]-acetic acid ethyl ester;

[(R)-2-(7-cyclopentylamino-1H-indol-2-yl)-4,5-dihydro-thiazol-4-yl]-ethanol;

[(R)-2-(7-(tetrahydropyran-4-yl)amino-1H-indol-2-yl)-4,5-dihydro-thiazol-4-yl]-carboxylic acid;

[(R)-2-(7-(tetrahydropyran-4-yl)amino-1H-indol-2-yl)-4,5-dihydro-thiazol-4-yl]-ethanol;

[(R)-2-(5-methoxy-7-cyclopentylamino-1H-indol-2-yl)-4,5-dihydro-thiazol-4-yl]-acetic acid methyl ester;

[(R)-2-(5-methoxy-7-cyclopentylamino-1H-indol-2-yl)-4,5-dihydro-thiazol-4-yl]-acetic acid;

[(R)-2-(5-methoxy-7-(tetrahydropyran-4-yl)amino-1H-indol-2-yl)-4,5-dihydro-thiazol-4-yl]-acetic acid;

[(R)-2-(5-ethoxy-7-cyclopentylamino-1H-indol-2-yl)-4,5-dihydro-thiazol-4-yl]-acetic acid;

[(R)-2-(5-propyloxy-7-cyclopentylamino-1H-indol-2-yl)-4,5-dihydro-thiazol-4-yl]-acetic acid;

[(R)-2-(5-phenoxy-7-cyclopentylamino-1H-indol-2-yl)-4,5-dihydro-thiazol-4-yl]-acetic acid;

[(R)-2-(5-phenoxy-7-(tetrahydropyran-4-yl)amino-1H-indol-2-yl)-4,5-dihydro-thiazol-4-yl]acetic acid;

[(R)-2-(5-(pyridin-3-yl)oxy-7-cyclopentylamino-1H-indol-2-yl)-4,5-dihydro-thiazol-4-yl]-acetic acid methyl ester;

[(R)-2-(5-(pyridin-3-yl)oxy-7-cyclopentylamino-1H-indol-2-yl)-4,5-dihydro-thiazol-4-yl]-acetic acid;

[(R)-2-(5-(pyridin-3-yl)oxy-7-(tetrahydropyran-4-yl)amino-1H-indol-2-yl)-4,5-dihydro-thiazol-4-yl]-acetic acid methyl ester;

[(R)-2-(5-(pyridin-3-yl)oxy-7-(tetrahydropyran-4-yl)amino-1H-indol-2-yl)-4,5-dihydro-thiazol-4-yl]-acetic acid;

[(R)-2-(5-methyl-7-cyclopentylamino-1H-indol-2-yl)-4,5-dihydro-thiazol-4-yl]-acetic acid methyl ester;

[(R)-2-(5-methyl-7-cyclopentylamino-1H-indol-2-yl)-4,5-dihydro-thiazol-4-yl]-acetic acid;

[(R)-2-(5-methyl-7-(tetrahydropyran-4-yl)amino-1H-indol-2-yl)-4,5-dihydro-thiazol-4-yl]-acetic acid;

[(R)-2-(5-(4-(methanesulfonyl)phenoxy)-7-cyclopentylamino-1H-indol-2-yl)-4,5-dihydro-thiazol-4-yl]-acetic acid;

[(R)-2-(5-phenoxymethyl-7-cyclopentylamino-1H-indol-2-yl)-4,5-dihydro-thiazol-4-yl]-acetic acid methyl ester;

[(R)-2-(5-phenylaminomethyl-7-cyclopentylamino-1H-indol-2-yl)-4,5-dihydro-thiazol-4-yl]-acetic acid methyl ester;

[(R)-2-(5-methanesulfonylmethyl-7-cyclopentylamino-1H-indol-2-yl)-4,5-dihydro-thiazol-4-yl]-acetic acid methyl ester;

[(R)-2-(5-methanesulfonylmethyl-7-cyclopentylamino-1H-indol-2-yl)-4,5-dihydro-thiazol-4-yl]-acetic acid;

[(R)-2-(5-methanesulfonylmethyl-7-cyclopentylamino-1H-indol-2-yl)-4,5-dihydro-thiazol-4-yl]-ethanol;

[(R)-2-(7-cyclopentylamino-1H-indol-2-yl)-4,5-dihydro-thiazol-4-yl]-ethyl acetamide;

3-[(R)-2-(5-chloro-7-cyclopentylamino-1H-indol-2-yl)-4,5-dihydro-thiazol-4-yl]-propionic acid;

[(R)-2-(5-chloro-7-cyclopentylamino-1H-indol-2-yl)-4,5-dihydro-thiazol-4-yl]-propanol;

3-[(R)-2-(5-chloro-7-(tetrahydropyran-4-yl)amino-1H-indol-2-yl)-4,5-dihydro-thiazol-4-yl]-propionic acid;

3-[(R)-2-(5-chloro-7-(tetrahydropyran-4-yDamino-1H-indol-2-yl)-4,5-dihydro-thiazol-4-yl]-propanol;

3-[(R)-2-(5-methyl-7-cyclopentylamino-1H-indol-2-yl)-4,5-dihydro-thiazol-4-yl]-propionic acid ethyl ester;

3-[(R)-2-(5-methyl-7-cyclopentylamino-1H-indol-2-yl)-4,5-dihydro-thiazol-4-yl]-propionic acid;

3-[(R)-2-(5-phenoxy-7-cyclopentylamino-1H-indol-2-yl)-4,5-dihydro-thiazol-4-yl]-propionic acid;

3-[(R)-2-(5-fluoro-7-cyclopentylamino-1H-indol-2-yl)-4,5-dihydro-thiazol-4-yl]-propionic acid ethyl ester;

3-[(R)-2-(5-fluoro-7-cyclopentylamino-1H-indol-2-yl)-4,5-dihydro-thiazol-4-yl]-propionic acid;

3-[(R)-2-(5-bromo-7-cyclopentylamino-1H-indol-2-yl)-4,5-dihydro-thiazol-4-yl]-propionic acid ethyl ester;

3-[(R)-2-(5-bromo-7-cyclopentylamino-1H-indol-2-yl)-4,5-dihydro-thiazol-4-yl]-propionic acid;

3-[(R)-2-(7-cyclopentylamino-1H-indol-2-yl)-4,5-dihydro-thiazol-4-yl]-propionic acid;

3-[(R)-2-(5-methoxy-7-cyclopentylamino-1H-indol-2-yl)-4,5-dihydro-thiazol-4-yl]-propionic acid;

3-[(R)-2-(5-ethoxy-7-cyclopentylamino-1H-indol-2-yl)-4,5-dihydro-thiazol-4-yl]-propionic acid ethyl ester;

3-[(R)-2-(5-ethoxy-7-cyclopentylamino-1H-indol-2-yl)-4,5-dihydro-thiazol-4-yl]-propionic acid;

3-[(R)-2-(5-trifluoromethoxy-7-cyclopentylamino-1H-indol-2-yl)-4,5-dihydro-thiazol-4-yl]-propionic acid ethyl ester;

3-[(R)-2-(5-trifluoromethoxy-7-cyclopentylamino-1H-indol-2-yl)-4,5-dihydro-thiazol-4-yl]-propionic acid;

[(R)-2-(5-methyl-7-(tetrahydropyran-4-yl)amino-1H-indol-2-yl)-4,5-dihydro-oxazol-4-yl]-ethanol;

[(S)-2-(5-methyl-7-cyclopentylamino-1H-indol-2-yl)-4,5-dihydro-oxazol-4-yl]-acetic acid;

[(S)-2-(5-methyl-7-(tetrahydropyran-4-yl)amino-1H-indol-2-yl)-4,5-dihydro-oxazol-4-yl]-acetic acid;

[(S)-2-(5-chloro-7-cyclopentylamino-1H-indol-2-yl)-4,5-dihydro-oxazol-4-yl]-acetic acid;

[(S)-2-(5-chloro-7-(tetrahydropyran-4-yl)methylamino-1H-indol-2-yl)-4,5-dihydro-oxazol-4-yl]acetic acid;

[2-((4S,5R)-5-aminomethyl-4-benzyl-dihydro-oxazol-2-yl)-5-chloro-1H-indol-7-yl]-cyclopentyl-amine;

{2-[(R)-5-((S)-1-amino-2-phenyl-ethyl)-4,5-dihydro-oxazol-2-yl]-5-chloro-1H-indol-7-yl}-cyclopentyl-amine;

(Tetrahydropyran-4-yl)-[2-(4,5-dihydro-oxazol-2-yl)-1H-indol-7-yl]-amine;

[2-(7-(Tetrahydropyran-4-yl)methylamino-1H-indol-2-yl)-4,5-dihydro-isoxadiazol-4-yl]-acetic acid;

[2-(7-(Tetrahydropyran-4-yl)methylamino-1H-indol-2-yl)-4,5-dihydro-isoxadiazol-4-yl]-ethanol;

Cyclopentyl-[2-(4,5-dihydro-oxadiazol-2-yl)-1H-indol-7-yl]-amine;

[2-(5-Methyl-7-cyclopentylamino-1H-indol-2-yl)-thiazol-4-yl]-methanol;

[2-(5-Methyl-7-cyclopentylamino-1H-indol-2-yl)-thiazol-5-yl]-methanol;

[2-(5-Methyl-7-cyclopentylamino-1H-indol-2-yl)-thiazol-4-yl]-carboxylic acid ethyl ester;

[2-(5-Methyl-7-cyclopentylamino-1H-indol-2-yl)-thiazol-4-yl]-carboxylic acid;

[2-(7-Cyclopentylamino-1H-indol-2-yl)-thiazol-4-yl]-methanol;

[2-(7-Cyclopentylamino-1H-indol-2-yl)-thiazol-4-yl]-carboxylic acid methyl ester;

{(R)-2-[5-methyl-7-(4-oxo-cyclohexylamino)-1H-indol-2-yl]-4,5-dihydro-thiazol-4-yl}acetic acid;

2-[(R)-2-(5-chloro-7-cyclopentylamino-1H-indol-2-yl)-4,5-dihydro-thiazol-4-yl]-1-morpholin-4-yl-ethanone;

2-[(R)-2-(5-chloro-7-cyclopentylamino-1H-indol-2-yl)-4,5-dihydro-thiazol-4-yl]-1-(morpholin-4-yl)ethylamino-ethanone;

2-[(R)-2-(5-chloro-7-cyclopentylamino-1H-indol-2-yl)-4,5-dihydro-thiazol-4-yl]-1-(morpholin-4-yl)propylamino-ethanone;

2-[(R)-2-(5-chloro-7-cyclopentylamino-1H-indol-2-yl)-4,5-dihydro-thiazol-4-yl]-1-methylamino-ethanone;

2-[(R)-2-(5-chloro-7-cyclopentylamino-1H-indol-2-yl)-4,5-dihydro-thiazol-4-yl]-1-dimethylamino-ethanone;

2-[(R)-2-(5-chloro-7-cyclopentylamino-1H-indol-2-yl)-4,5-dihydro-thiazol-4-yl]-1-[4-(methyl)piperazin-1-yl]-ethanone;

2-[(R)-2-(5-chloro-7-cyclopentylamino-1H-indol-2-yl)-4,5-dihydro-thiazol-4-yl]-1-(3-dimethylaminopyrrolidin-1-yl)-ethanone;

2-[(R)-2-(5-chloro-7-cyclopentylamino-1H-indol-2-yl)-4,5-dihydro-thiazol-4-yl]-1-(piperidin-4-yl)-ethanone;

2-[(R)-2-(5-chloro-7-(tetrahydropyran-4-yl)methylamino-1H-indol-2-yl)-4,5-dihydro-thiazol-4-yl]-1-methylamino-ethanone;

2-[(R)-2-(5-chloro-7-(tetrahydropyran-4-yl)methylamino-1H-indol-2-yl)-4,5-dihydro-thiazol-4-yl]-1-(morpholin-4-yl)-ethanone;

2-[(R)-2-(5-fluoro-7-cyclopentylamino-1H-indol-2-yl)-4,5-dihydro-thiazol-4-yl]-1-(4-(methyl)piperazin-1-yl)-ethanone;

2-[(R)-2-(5-fluoro-7-cyclopentylamino-1H-indol-2-yl)-4,5-dihydro-thiazol-4-yl]-1-(morpholin-4-yl)ethylamino-ethanone;

2-[(R)-2-(5-methoxy-7-cyclopentylamino-1H-indol-2-yl)-4,5-dihydro-thiazol-4-yl]-1-(methylamino)-4-yl-ethanone;

2-[(R)-2-(5-methoxy-7-cyclopentylamino-1H-indol-2-yl)-4,5-dihydro-thiazol-4-yl]-1-(morpholin-4-yl)-ethanone;

2-[(R)-2-(7-cyclopentylamino-1H-indol-2-yl)-4,5-dihydro-thiazol-4-yl]-1-methylamino-ethanone;

2-[(R)-2-(7-cyclopentylamino-1H-indol-2-yl)-4,5-dihydro-thiazol-4-yl]-1-(morpholin-4-yl)-ethanone;

2-[(R)-2-(7-(tetrahydropyran-4-yl)methylamino-1H-indol-2-yl)-4,5-dihydro-thiazol-4-yl]-1-methylamino-ethanone;

2-[(R)-2-(7-(tetrahydropyran-4-yl)methylamino-1H-indol-2-yl)-4,5-dihydro-thiazol-4-yl]-1-(morpholin-4-yl)-ethanone;

2-[(R)-2-(5-chloro-7-cyclopentylamino-1H-indol-2-yl)-4,5-dihydro-thiazol-4-yl]-1-(morpholin-4-yl)ethylamino-ethanone;

2-[(R)-2-(5-chloro-7-cyclopentylamino-1H-indol-2-yl)-4,5-dihydro-thiazol-4-yl]-1-(4-(methyl)piperazin-1-yl)-ethanone;

Cyclopentyl-{5-methanesulfonylmethyl-2-[(R)-4-(2-morpholin-4-yl-ethyl)-4,5-dihydro-thiazol-2-yl]-1H-indol-7-yl}-amine;

1-(4-{2-[(R)-2-(7-cyclopentylamino-5-methanesulfonylmethyl-1H-indol-2-yl)-4,5-dihydro-thiazol-4-yl]-ethyl}-piperazin-1-yl)-ethanone;

Cyclopentyl-[2-((R)-4-pyrrolidin-1-ylmethyl-4,5-dihydro-thiazol-2-yl)-1H-indol-7-yl]-amine;

{5-Chloro-2-[(R)-4-(2-dimethylamino-ethyl)-4,5-dihydro-thiazol-2-yl]-1H-indol-7-yl}-cyclopentyl-amine;

{5-Chloro-2-[(R)-4-(2-piperazin-1-yl-ethyl)-4,5-dihydro-thiazol-2-yl]-1H-indol-7-yl}-cyclopentyl-amine;

(5-Chloro-2-{(R)-4-[2-(4-ethanesulfonyl-piperazin-1-yl)-ethyl]-4,5-dihydro-thiazol-2-yl}-1H-indol-7-yl)-cyclopentyl-amine;

1-(4-{2-[(R)-2-(5-chloro-7-cyclopentylamino-1H-indol-2-yl)-4,5-dihydro-thiazol-4-yl]-ethyl}-piperazin-1-yl)-2-hydroxy-ethanone;

{5-Chloro-2-[(R)-4-(2-pyrazol-1-yl-ethyl)-4,5-dihydro-thiazol-2-yl]-1H-indol-7-yl}-cyclopentyl-amine;

(S)-1-{2-[(R)-2-(5-chloro-7-cyclopentylamino-1H-indol-2-yl)-4,5-dihydro-thiazol-4-yl]ethyl}-pyrrolidine-2-carboxylic acid;

{5-Chloro-2-[(R)-4-(2-methanesulfonyl-ethyl)-4,5-dihydro-thiazol-2-yl]-1H-indol-7-yl}-cyclopentyl-amine;

3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid ethyl ester;

3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid;

1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid;

[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-carbamic acid t-butyl ester;

(2-{(R)-4-[2-((S)-3-amino-pyrrolidin-1-yl)-ethyl]-4,5-dihydro-thiazol-2-yl}-5-chloro-1H-indol-7-yl)-(tetrahydro-pyran-4-yl)-amine;

N—[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-acetamide;

Cyclopentyl-{2-[(R)-4-(2-methoxy-ethyl)-4,5-dihydro-thiazol-2-yl]-1H-indol-7-yl}-amine;

[2-((R)-4-aminomethyl-4,5-dihydro-thiazol-2-yl)-1H-indol-7-yl]-cyclopentyl-amine;

{2-[(R)-4-((R)-3-amino-pyrrolidin-1-ylethyl)-4,5-dihydro-thiazol-2-yl]-5-chloro-1H-indol-7-yl}-cyclopentyl-amine;

4-[(R)-2-(7-cyclopentylamino-5-ethoxy-1H-indol-2-yl)-4,5-dihydro-thiazol-4-ylethyl]-piperazin-2-one;

{2-[(R)-4-(S)-3-amino-pyrrolidin-1-ylethyl)-4,5-dihydro-thiazol-2-yl]-5-chloro-1H-indol-7-yl}-cyclopentyl-amine;

(5-Chloro-2-{(S)-4-[2-(3-dimethylamino-phenyl)-ethyl]-4,5-dihydro-thiazol-2-yl}-1H-indol-7-yl)-cyclopentyl-amine;

1-(4-{2-[(S)-2-(7-cyclopentylamino-5-chloro-1H-indol-2-yl)-4,5-dihydro-thiazol-4-yl]-ethyl}-piperazin-1-yl)-ethanone;

1-(4-{2-[(S)-2-(7-cyclopentylamino-1H-indol-2-yl)-4,5-dihydro-thiazol-4-yl]-ethyl}-piperazin-1-yl)-ethanone;

(5-Methoxy-2-{(R)-4-[2-(pyrrolidin-1-yl)-ethyl]-4,5-dihydro-thiazol-2-yl}-1H-indol-7-yl)-cyclopentyl-amine;

(2-{(R)-4-[(pyrrolidin-1-yl)-ethyl]-4,5-dihydro-thiazol-2-yl}-1H-indol-7-yl)-(tetrahydro-pyran-4-yl)-amine;

(2-{(S)-4-[(2-oxopiperazin-4-yl)-ethyl]-4,5-dihydro-thiazol-2-yl}-1H-indol-7-yl)-(tetrahydro-pyran-4-yl)-amine;

(5-Methanesulfonylmethyl-2-{(S)-4-[(2-oxopiperazin-4-yl)-ethyl]-4,5-dihydro-thiazol-2-yl}-1H-indol-7-yl)-cyclopentyl-amine;

(5-Methyl-2-{(S)-4-[(morpholin-4-yl)-ethyl]-4,5-dihydro-thiazol-2-yl}-1H-indol-7-yl)-(tetrahydro-pyran-4-yl)-amine;

1-(4-{2-[(R)-2-(7-cyclopentylamino-5-chloro-1H-indol-2-yl)-4,5-dihydro-thiazol-4-yl]-ethyl}-piperazin-1-yl)-ethanone;

(5-Chloro-2-{(R)-4-[4-methyl-piperazin-1-yl)-ethyl]-4,5-dihydro-thiazol-2-yl}-1H-indol-7-yl)-cyclopentyl-amine;

(5-Chloro-2-{(R)-4-[4-(hydroxy)piperidin-1-yl)-ethyl]-4,5-dihydro-thiazol-2-yl}-1H-indol-7-yl)-cyclopentyl-amine;

(5-Chloro-2-{(R)-4-[2-oxopiperazin-4-yl)-ethyl]-4,5-dihydro-thiazol-2-yl}-1H-indol-7-yl)-cyclopentyl-amine;

(5-Chloro-2-{(R)-4-[(piperidin-1-yl)-ethyl]-4,5-dihydro-thiazol-2-yl}-1H-indol-7-yl)-cyclopentyl-amine;

(5-Chloro-2-{(R)-4-[(1,1-dioxo-thiomorpholin-4-yl)-ethyl]-4,5-dihydro-thiazol-2-yl}-1H-indol-7-yl)-cyclopentyl-amine;

(5-Chloro-2-{(R)-4-[(2-oxopyrrolidin-1-yl)-ethyl]-4,5-dihydro-thiazol-2-yl}-1H-indol-7-yl)-cyclopentyl-amine;

(5-Chloro-2-{(R)-4-[((3S)-3-(dimethylaminocarboxy)piperidin-1-yl)-ethyl]-4,5-dihydro-thiazol-2-yl}-1H-indol-7-yl)-(tetrahydro-pyran-4-yl)-amine;

(5-Chloro-2-{(R)-4-[(piperazin-1-yl)-ethyl]-4,5-dihydro-thiazol-2-yl}-1H-indol-7-yl)-(tetrahydro-pyran-4-yl)-amine;

1-(4-{2-[(R)-2-(5-chloro-7-(tetrahydro-pyran-4-ylamino)-1H-indol-2-yl)-4,5-dihydro-thiazol-4-yl]-ethyl}-piperazin-1-yl)-2-hydroxy-ethanone;

(5-Chloro-2-{(R)-4-[(1-(trifluoroacetyl)piperazin-4-yl)-ethyl]-4,5-dihydro-thiazol-2-yl}-1H-indol-7-yl)-(tetrahydro-pyran-4-yl)-amine;

(5-Chloro-2-{(R)-4-[(1-[(furan-2-yl)carbonyl]piperazin-4-yl)-ethyl]-4,5-dihydro-thiazol-2-yl}-1H-indol-7-yl)-(tetrahydro-pyran-4-yl)-amine;

(5-Chloro-2-{(R)-4-[(1,4-pyrazin-2-yl)piperazin-4-yl-ethyl]-4,5-dihydro-thiazol-2-yl}-1H-indol-7-yl)-(tetrahydro-pyran-4-yl)-amine;

(5-Chloro-2-{(R)-4-[(1,3-pyrazin-2-yl)piperazin-4-yl-ethyl]-4,5-dihydro-thiazol-2-yl}-1H-indol-7-yl)-(tetrahydro-pyran-4-yl)-amine;

(5-Fluoro-2-{(R)-4-(2-aminoethyl)-4,5-dihydro-thiazol-2-yl}-1H-indol-7-yl)-cyclopentyl-amine;

1-(4-{2-[(R)-2-(5-fluoro-7-cyclopentylamino)-1H-indol-2-yl)-4,5-dihydro-thiazol-4-yl]-ethyl}-piperazin-1-yl)-2-hydroxy-ethanone;

(5-Fluoro-2-{(R)-4-[(morpholin-4-yl)-ethyl]-4,5-dihydro-thiazol-2-yl}-1H-indol-7-yl)-cyclopentyl-amine;

(5-Fluoro-2-{(R)-4-(2-dimethylamino-ethyl)-4,5-dihydro-thiazol-2-yl}-1H-1-indol-7-yl)-cyclopentyl-amine;

(5-Fluoro-2-{(R)-4-[(pyrrolidin-1-yl)-ethyl]-4,5-dihydro-thiazol-2-yl}-1H-indol-7-yl)-cyclopentyl-amine;

(5-Fluoro-2-{(R)-4-[(1,1-dioxo-thiomorpholin-4-yl)-ethyl]-4,5-dihydro-thiazol-2-yl}-1H-indol-7-yl)-cyclopentyl-amine;

(5-Fluoro-2-{(R)-4-[(2-oxopyrrolidin-1-yl)-ethyl]-4,5-dihydro-thiazol-2-yl}-1H-indol-7-yl)-cyclopentyl-amine;

1-(4-{2-[(5-Fluoro-7-cyclopentylamino-1H-indol-2-yl)-4,5-dihydro-thiazol-4-yl]ethyl}-piperazin-1-yl)-2-hydroxy-ethanone;

(5-Fluoro-2-{(R)-4-[methanesulfonyl-ethyl]-4,5-dihydro-thiazol-2-yl}-1H-indol-7-yl)-cyclopentyl-amine;

(5-Fluoro-2-{(R)-4-(2-dimethylamino-ethyl)-4,5-dihydro-thiazol-2-yl}-1H-indol-7-yl)-(tetrahydro-pyran-4-yl)-amine;

(5-Fluoro-2-{(R)-4-[(pyrrolidin-1-yl)-ethyl]-4,5-dihydro-thiazol-2-yl}-1H-indol-7-yl)-(tetrahydro-pyran-4-yl)-amine;

(5-Fluoro-2-{(R)-4-[(morpholin-4-yl)-ethyl]-4,5-dihydro-thiazol-2-yl}-1H-indol-7-yl)-(tetrahydro-pyran-4-yl)-amine;

1-(4-{2-[(R)-2-(7-(tetrahydro-pyran-4-ylamino)-5-fluoro-1H-indol-2-yl)-4,5-dihydro-thiazol-4-yl]-ethyl}-piperazin-1-yl)-ethanone;

(5-Fluoro-2-{(R)-4-[(1,1-dioxo-thiomorpholin-4-yl)-ethyl]-4,5-dihydro-thiazol-2-yl}-1H-indol-7-yl)-(tetrahydro-pyran-4-yl)-amine;

(5-Fluoro-2-{(R)-4-[2-methanesulfonyl-ethyl]-4,5-dihydro-thiazol-2-yl}-1H-indol-7-yl)-(tetrahydro-pyran-4-yl)-amine;

(5-Fluoro-2-{(R)-4-[2-oxopiperazin-4-yl)-ethyl]-4,5-dihydro-thiazol-2-yl}-1H-indol-7-yl)-(tetrahydro-pyran-4-yl)-amine;

1-(4-{2-[(R)-2-(5-fluoro-7-(tetrahydro-pyran-4-ylamino)-1H-indol-2-yl)-4,5-dihydro-thiazol-4-yl]ethyl}-piperazin-1-yl)-2-hydroxy-ethanone;

(2-{(R)-4-[2-dimethylamino-ethyl]-4,5-dihydro-thiazol-2-yl}-1H-indol-7-yl)-cyclopentyl-amine;

(2-{(R)-4-[(piperidin-1-yl)-ethyl]-4,5-dihydro-thiazol-2-yl}-1H-indol-7-yl)-cyclopentyl-amine;

2-{(R)-4-[2-methanesulfonyl-ethyl]-4,5-dihydro-thiazol-2-yl}-1H-indol-7-yl)-(tetrahydro-pyran-4-yl)-amine;

1-(4-{2-[(R)-2-(5-methoxy-7-cyclopentylamino-1H-indol-2-yl)-4,5-dihydro-thiazol-4-yl]-ethyl}-piperazin-1-yl)-2-hydroxy-ethanone;

1-(4-{2-[(R)-2-(7-cyclopentylamino)-5-chloro-1H-indol-2-yl)-4,5-dihydro-thiazol-4-yl]-propyl}-piperazin-1-yl)-ethanone;

2-{(R)-4-[(morpholin-4-yl)-methyl]-4,5-dihydro-thiazol-2-yl}-1H-indol-7-yl)-cyclopentyl-amine;

(5-Chloro-2-{(R)-4-[(morpholin-4-yl)-propyl]-4,5-dihydro-thiazol-2-yl}-1H-indol-7-yl)-cyclopentyl-amine;

(2-{(R)-4-[2-dimethylamino-methyl]-4,5-dihydro-thiazol-2-yl}-1H-indol-7-yl)-cyclopentyl-amine;

(5-Chloro-2-{(S)-4-[(morpholin-4-yl)-ethyl]-4,5-dihydro-thiazol-2-yl}-1H-indol-7-yl)-cyclopentyl-amine;

{5-Methyl-2-[(R)-4-(2-morpholin-4-yl-ethyl)-4,5-dihydro-oxazol-2-yl]-1H-indol-7-yl}-(tetrahydropyran-4-yl)-amine;

{5-Methyl-2-[(S)-4-(2-morpholin-4-yl-ethyl)-4,5-dihydro-thiazol-2-yl]-1H-indol-7-yl}-(tetrahydro-pyran-4-ylmethyl)-amine;

1-(4-{2-[(S)-2-(5-phenoxy-7,7-diisobutylamino)-1H-indol-2-yl)-4,5-dihydro-thiazol-4-yl]-ethyl}-piperazin-1-yl)-ethanone;

(5-Phenoxy-2-{(S)-4-[(pyrrolidin-1-yl)-ethyl]-4,5-dihydro-thiazol-2-yl}-1H-indol-7-yl)-diisobutyl-amine;

1-(4-{2-[(S)-2-(5-phenoxy-7-cyclopentylamino)-1H-indol-2-yl)-4,5-dihydro-thiazol-4-yl]-ethyl}-piperazin-1-yl)-2-hydroxy-ethanone;

(5-Phenoxy-2-{(S)-4-[(piperazin-1-yl)-ethyl]-4,5-dihydro-thiazol-2-yl}-1H-indol-7-yl)-cyclopentyl-amine;

t-Butyl-(4-{2-[(S)-2-(5-phenoxy-7-cyclopentylamino)-1H-indol-2-yl)-4,5-dihydro-thiazol-4-yl]-ethyl}-piperazine-1-carboxylate;

Cyclopentyl-(5-phenoxy-2-{(S)-4-[2-(3-fluoromethyl-5,6-dihydro-8H-[1,2,4]triazolo[4,3-a]pyrazin-7-yl)-ethyl]-4,5-dihydro-thiazol-2-yl}-1H-indol-7-yl)-amine;

(5-Phenoxy-2-{(S)-4-[2-oxopiperazin-4-yl)-ethyl]-4,5-dihydro-thiazol-2-yl}-1H-indol-7-yl)-cyclopentyl-amine;

(4-{2-[(S)-2-(5-phenoxy-7-cyclopentylamino)-1H-indol-2-yl)-4,5-dihydro-thiazol-4-yl]-ethyl}-piperazin-1-yl)-oxoran-2-yl-methanone;

(5-Phenoxy-2-{(S)-4-[(pyridin-2-yl)piperazine-ethyl]-4,5-dihydro-thiazol-2-yl}-1H-indol-7-yl)-cyclopentyl-amine;

(5-Phenoxy-2-{(S)-4-[(2-fluorophenyl)piperazine-ethyl]-4,5-dihydro-thiazol-2-yl}-1H-indol-7-yl)-cyclopentyl-amine;

(5-Chloro-2-{(S)-4[2-oxopiperazin-4-yl)-ethyl]-4,5-dihydro-thiazol-2-yl}-1H-indol-7-yl)-cyclopentyl-amine;

(5-Phenoxy-2-{(S)-4-[(3S)-3-(amino)pyrrolidin-1-yl-ethyl]-4,5-dihydro-thiazol-2-yl}-1H-indol-7-yl)-cyclopentyl-amine;

1-(4-{2-[(S)-2-(5-phenoxy-7-cyclopentylamino)-1H-indol-2-yl)-4,5-dihydro-thiazol-4-yl]-ethyl}-piperazin-1-yl)-ethanone;

(5-Methyl-2-{(S)-4[2-(aminocarbonyl)pyrrolidin-1-yl-ethyl]-4,5-dihydro-thiazol-2-yl}-1H-indol-7-yl)-(tetrahydropyran-4-yl)methyl-amine;

(5-Methyl-[(S)-2-(7-(tetrahydropyran-4-yl)methylamino-1H-indol-2-yl)-4,5-dihydro-thiazol-4-yl])-pyrrolidin-2-yl-methanol;

(5-Chloro-[(S)-2-(7-cyclopentylamino-1H-indol-2-yl)-4,5-dihydro-thiazol-4-yl])-pyrrolidin-3-yl-acetamide;

(5-Phenoxy-2-{(S)-4-[4-(benzyl)piperazin-1-yl-ethyl]-4,5-dihydro-thiazol-2-yl}-1H-indol-7-yl)-cyclopentyl-amine;

(5-Methyl-2-{(S)-4-[2-diethoxyphosphoryl-ethyl]-4,5-dihydro-thiazol-2-yl}-1H-indol-7-yl)-(tetrahydropyran-4-yl) methyl-amine;

(5-Methyl-2-{(S)-4-[morpholin-4-yl-ethyl]-4,5-dihydro-thiazol-2-yl}-1H-indol-7-yl)-(tetrahydropyran-4-yl)methyl-amine;

(5-Phenoxy-2-{(R)-4-[pyrrolidin-1-yl-ethyl]-4,5-dihydro-thiazol-2-yl}-1H-indol-7-yl)-cyclopentyl-amine;

(5-Phenoxy-2-{(S)-4-[morpholin-4-yl-ethyl]-4,5-dihydro-thiazol-2-yl}-1H-indol-7-yl)-(tetrahydropyran-4-yl)methyl-amine;

(5-Phenoxy-2-{(S)-4-[2-oxopiperazin-4-yl-ethyl]-4,5-dihydro-thiazol-2-yl}-1H-indol-7-yl)-(tetrahydropyran-4-yl) methyl-amine;

(5-Phenoxy-2-{(S)-4-[pyrrolidin-1-yl-ethyl]-4,5-dihydro-thiazol-2-yl}-1H-indol-7-yl)-cyclopentyl-amine;

(5-Methyl-2-{(S)-4-[2-oxopiperazin-4-yl-ethyl]-4,5-dihydro-thiazol-2-yl}-1H-indol-7-yl)-4,4-difluorocyclohexyl-amine;

(5-Methyl-2-{(S)-4-[morpholin-4-yl-ethyl]-4,5-dihydro-thiazol-2-yl}-1H-indol-7-yl)-4,4-difluorocyclohexyl-amine;

(Tetrahydropyran-4-yl)-(5-methyl-2-{(S)-4-[2-(3-fluoromethyl-5,6-dihydro-8H-[1,2,4]triazolo[4,3-a]pyrazin-7-yl)-ethyl]-4,5-dihydro-thiazol-2-yl}-1H-indol-7-yl)-amine;

(5-Methyl-2-{(S)-4-[2-oxopiperazin-4-yl-ethyl]-4,5-dihydro-thiazol-2-yl}-1H-indol-7-yl)-(tetrahydropyran-4-yl) methyl-amine;

(5-Chloro-2-{(S)-4-[1-(pyridin-2-yl)piperazin-4-yl-ethyl]-4,5-dihydro-thiazol-2-yl}-1H-indol-7-yl)-(tetrahydropyran-4-yl)-amine;

(4-{2-[(S)-2-(5-chloro-7-(tetrahydropyran-4-yl)-amino)-1H-indol-2-yl)-4,5-dihydro-thiazol-4-yl]-ethyl}-piperazin-1-yl)-oxoran-2-yl-methanone;

(5-Methoxy-2-{(R)-4-[2-oxopiperazin-4-yl-ethyl]-4,5-dihydro-thiazol-2-yl}-1H-indol-7-yl)-(tetrahydropyran-4-yl)-amine;

1-(4-{2-[(R)-2-(5-methoxy-7-cyclopentylamino-1H-indol-2-yl)-4,5-dihydro-thiazol-4-yl]-ethyl}-piperazin-1-yl)-2-hydroxy-ethanone;

[(R)-2-(5-aminomethyl-7-cyclopentylamino-1H-indol-2-yl)-4,5-dihydro-thiazol-4-yl]-methanol;

Furan-2-carboxylic acid [7-cyclopentylamino-2-((R)-4-hydroxymethyl-4,5-dihydro-thiazol-2-yl)-1H-indol-5-ylmethyl]-amide;

[(R)-2-(7-cyclopentylamino-1H-indol-2-yl)-4,5-dihydro-thiazol-4-ylmethoxy]-acetic acid methyl ester;

[(R)-2-(7-cyclopentylamino-1H-indol-2-yl)-4,5-dihydro-thiazol-4-ylmethoxy]-acetic acid;

Cyclopentyl-{2-[(R)-4-(3-cyclopentyl-[1,2,4]oxadiazol-5-ylmethyl)-4,5-dihydro-thiazol-2-yl]-1H-indol-7-yl}-amine; and Cyclopentyl-{2-[(R)-4-(3-piperidin-1-yl-[1,2,4]oxadiazol-5-ylmethyl)-4,5-dihydro-thiazol-2-yl]-1H-indol-7-yl}-amine.

The present invention also provides processes for preparing the compounds of formula (I). Hereinafter, the processes for preparing the compounds of formula (I) are illustrated by exemplary reaction schemes for the purpose of better understanding. However, a skilled artisan in the field to which the present invention pertains may prepare the compounds of formula (I) via various routes according to their structures, and such processes should be construed to fall under the scope of the present invention. In other words, the compounds of formula (I) may be prepared by optionally combining various synthetic methods which are described in the present specification or disclosed in the prior arts. The processes for preparing the compounds of formula (I) cover even such processes, and are not limited to those explained below.

First, the compounds of formula (1) can be prepared through amide coupling reaction or alkylation reaction from the compounds (2) and (3) according to the following Reaction Scheme (1).

Reaction Scheme 1

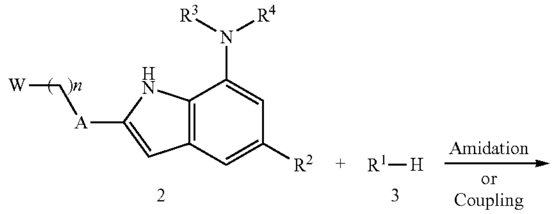

2 3

-continued

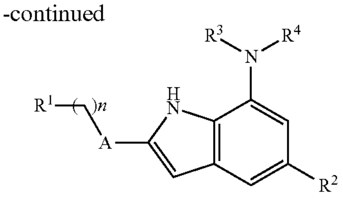

1 in the above Reaction Scheme (1),

A, $R^2$, $R^3$, $R^4$ and n are as defined above, and

W represents carboxylic acid used in the amide coupling reaction, or halogen, alkylsulfonate, etc. used in the coupling reaction.

In particular, $R^1$ in the above Reaction Scheme (1) preferably represents a group containing amine or carbon nucleophile.

The amidation reaction may be conducted using a coupling agent, such as for example, dicyclohexylcarbodiimide (DCC), EDC, N-[dimethylamino-1H-1,2,3-triazole[4, 5-b]-pyridin-1-ylmethylene]-N-methylmethanaminium (HATU), etc. together with HOBT. The reaction is carried out in DMF or DCM, in the presence of a base of $Et_3N$, DIPEA, etc., for 4 to 12 h, and at room temperature. In the case of a nucleophile containing a nitrogen atom, the alkylation reaction may be conducted using various bases such as $Et_3N$, $K_2CO_3$, NMPA, DBU, etc., in the solvent such as acetonitrile, THF, or DMF, at 25 to 80° C., and for 4 to 24 h. Most of the compound (3) are commercially available.

In the following Reaction Scheme (2), the compounds (2-1) and (2-2) whose A is 4,5-dihydro-thiazole can be prepared through a hydrolysis of (4,5-dihydro-thiazol-4-yl)-esters of compound (4), or prepared by synthesizing alcohols first through a reduction, and by introducing halide or sulfonyl group as a leaving group.

Reaction Scheme 2

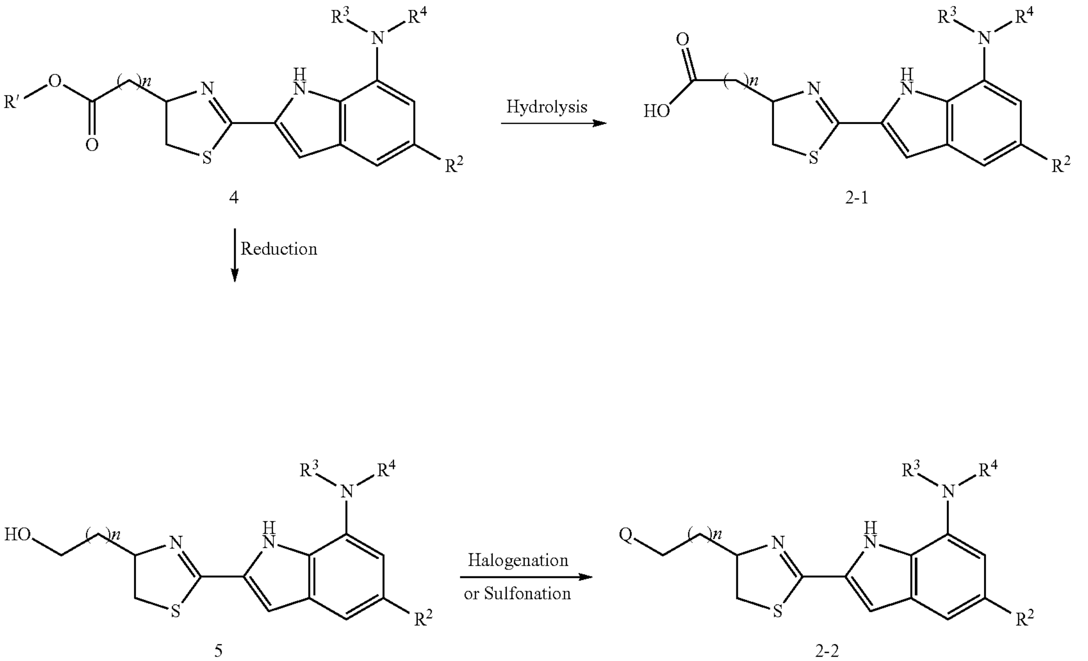

4 2-1 5 2-2 in the above Reaction Scheme (2), n, $R^2$, $R^3$ and $R^4$ are as defined above, Q represents a leaving group, preferably halogen or alkylsulfonate, and R' represents alkyl, preferably methyl, ethyl, isopropyl, etc.

Specifically, the carboxylic acid compound (2-1) can be obtained by hydrolyzing the ester compound (4), where 2 to 10 eq. of NaOH, LiOH, KOH, etc. is used as a base, and one or more solvents selected from water, methanol, THF and dioxane are used. This hydrolysis reaction is carried out for 30 min to 12 h at room temperature to 100° C.

The alcohol compound (5) can also be obtained by a reduction of the ester compound (4), where $NaBH_4$, $LiBH_4$, LAH, etc. is used as a reducing agent, and an alcohol such as methanol, THF, dioxane, etc. is used as a solvent. This reduction reaction is carried out for 30 min to 24 h at room temperature to 100° C. The reducing agent is conventionally used in an amount of 3 to 5 eq., but may be used in an excess amount of about 10 eq., if needed.

The halogenation reaction of the alcohol compound (5) may be carried out using an agent selected from iodine, bromine, N-iodosuccimide (NIS), N-bromosuccimide (NBS), carbon tetrachloride ($CCl_4$), carbon tetrabromide ($CBr_4$), etc., under the presence of a base such as imidazole, dimethylaminopyridine (DMAP), etc. and a phosphine such as triphenylphosphine ($Ph_3P$), tributylphosphine ($Bu_3P$), etc. Each of the halogenating agent, base and phosphine is conventionally used in an amount of 1 to 10 eq. with respect to the compound (5). The reaction may proceed in a solvent selected from ethers such as tetrahydrofuran, diethylether, etc., dichloromethane, chloroform, etc., at 0 to 50° C., and for 10 min to 12 h.

The sulfonylation reaction of the alcohol compound (5) may be carried out using an agent selected from methanesulfonylchloride, p-toluenesulfonylchloride, etc. in an amount of 1 to 10 eq. under the presence of an organic base such as pyridine, triethylamine, etc. This reaction may proceed in a solvent selected from dichloromethane, dichloroethane, etc., at 0 to 50° C., and for 10 min to 12 h.

The indole-4,5-dihydro-thiazole compound (4') may be obtained as depicted in the following Reaction Scheme (3), i.e., by introducing 4,5-dihydro-thiazole to the starting compound of 7-nitro-indole ester, reducing the nitro group, and carrying out a reductive amination reaction to introduce $R^3$ and $R^4$.

Reaction Scheme 3

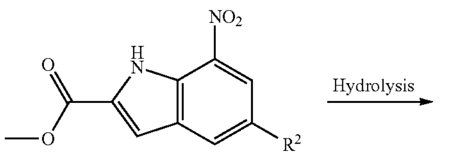

6

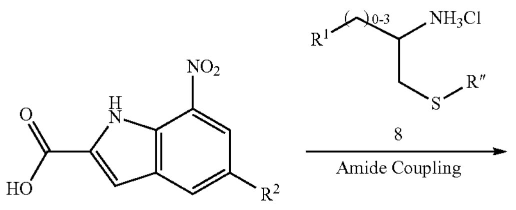

7

-continued

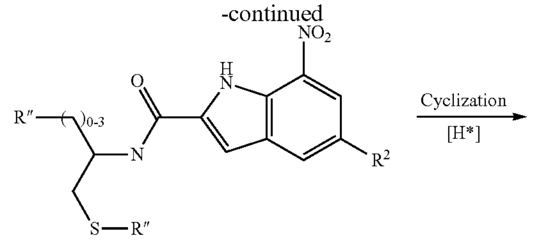

9

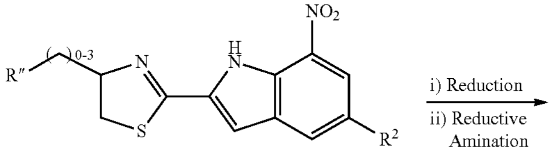

10

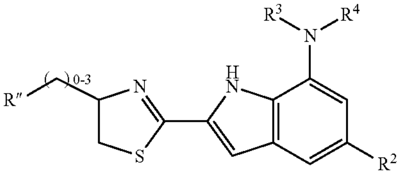

4' in the above Reaction Scheme (3), $R^2$ is as defined above,

R" represents p-methoxybenzyl (p-MeOBn) or triphenylmethyl ($Ph_3C$), and

R''' represents $R^1$ or protected $R^1$, and typically represents alkyloxycarbonyl (alkyl-OC(O)—) or alkyl carboxylate (alkyl-$CO_2$—).

The hydrolysis reaction in Reaction Scheme (3) is carried out in the same manner as explained for Reaction Scheme (2), and the amide coupling reaction is carried out as explained for Reaction Scheme (1). The cyclization reaction may be carried out using phosphorus pentachloride ($PCl_5$) in the solvent dichloromethane when R" is p-methoxybenzyl, or using trifluoromethanesulfonic anhydride ($Tf_2O$) and triphenylphosphineoxide ($Ph_3PO$) in the solvent dichloromethane when R" is triphenylmethyl.

The reduction of nitro group in the 7-nitroindole compound (10) may be carried out using an acid catalyst and a metal, or using a metallic catalyst under hydrogen gas. In the acid catalyst reaction, iron, zinc, lithium, sodium, or tin (typically, tin chloride) may be used as the metal, and inorganic acids such as hydrochloric acid, sulfuric acid, nitric acid, phosphoric acid, etc.; organic carboxylic acids such as acetic acid, trifluoroacetic acid, etc.; amine acid salts such as ammonium chloride, etc., preferably hydrochloric acid, acetic acid or ammonium chloride, may be used as the acid catalyst. Also, in the reduction using a metallic catalyst under hydrogen gas, palladium, nickel, platinum, ruthenium, rhodium, etc., preferably palladium or nickel, can be mentioned as the metallic catalyst that can be used.

The reductive amination reaction is carried out using a compound containing carbonyl group (ketone or aldehyde). As the reducing agent that can be used, sodium borohydride, sodium cyanoborohydride, sodium triacetoxyborohydride, etc. can be mentioned. The reaction may be facilitated using an acid as the catalyst. As the acid catalyst that can be used, inorganic acids such as hydrochloric acid, sulfuric acid, nitric acid, phosphoric acid, etc.; organic carboxylic acids such as acetic acid, trifluoroacetic acid, etc.; amine acid salts such as ammonium chloride, etc., more preferably hydrochloric acid or acetic acid, can be mentioned.

In the following Reaction Scheme (4), the compound (11) and the indole compound (7) are coupled to give the compound (9-1), which is then cyclized under an acid condition and hydrolyzed to give the compound (2-3) wherein R''' is alcohol. Also, the compound (2-4) which is obtained by substituting the alcohol group of the compound (2-3) with a leaving group may be reacted with the amine compound (14) to give the amine compound (2-5).

Reaction Scheme 4

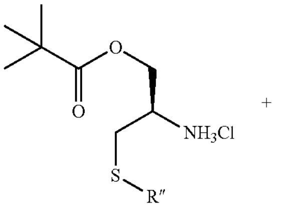

11

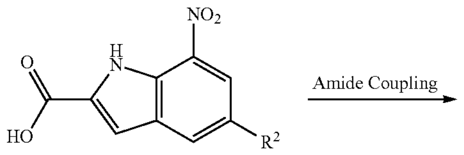

7

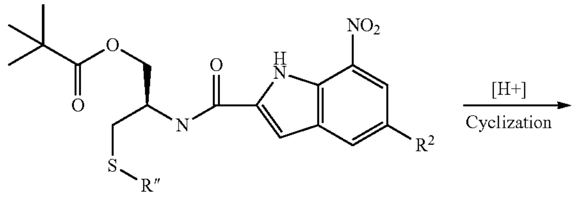

9-1

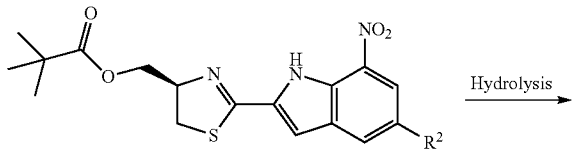

12

-continued

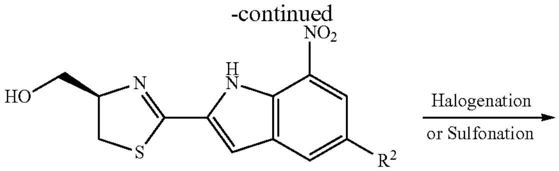

2-3

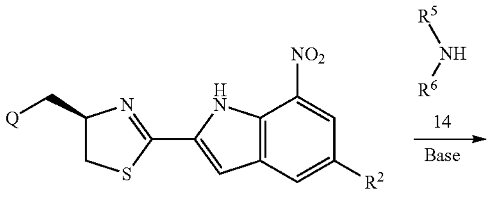

2-4

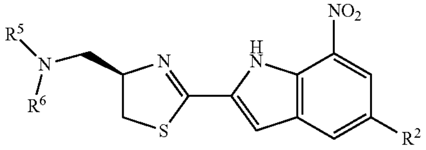

2-5 in the above Reaction Scheme (4),

Q, $R^2$, $R^5$, $R^6$ and R'' are as defined above.

The amide coupling and cyclization reactions may be carried out under the same conditions as explained for Reaction Schemes (1) and (3).

The hydrolysis reaction for obtaining the compound (2-3) is carried out in a solvent mixture of water and an organic solvent and in the presence of a base, where THF, methanol, dioxane, etc. may be used as the organic solvent, and LiOH, KOH, NaOH, etc. may be used as the base.

The reaction for introducing the leaving group Q may be carried out under the same conditions as explained for Reaction Scheme (2). The synthesis of the compound (2-5) due to the introduction of an amine group is done by reacting the amine compound (14) with the compound (2-4) in the presence of a base, at 25 to 80° C., and for 20 min to 24 h. As the base, $Et_3N$, DIPEA, DMAP, etc. may be mentioned, but the reaction may also be carried out in the absence of a base, if needed.

The 7-nitroindole compound (6) is commercially available, or may be prepared according to the following Reaction Scheme (5).

Reaction Scheme 5

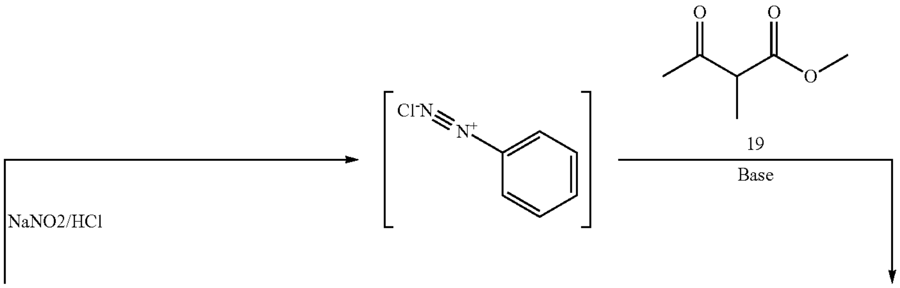

-continued

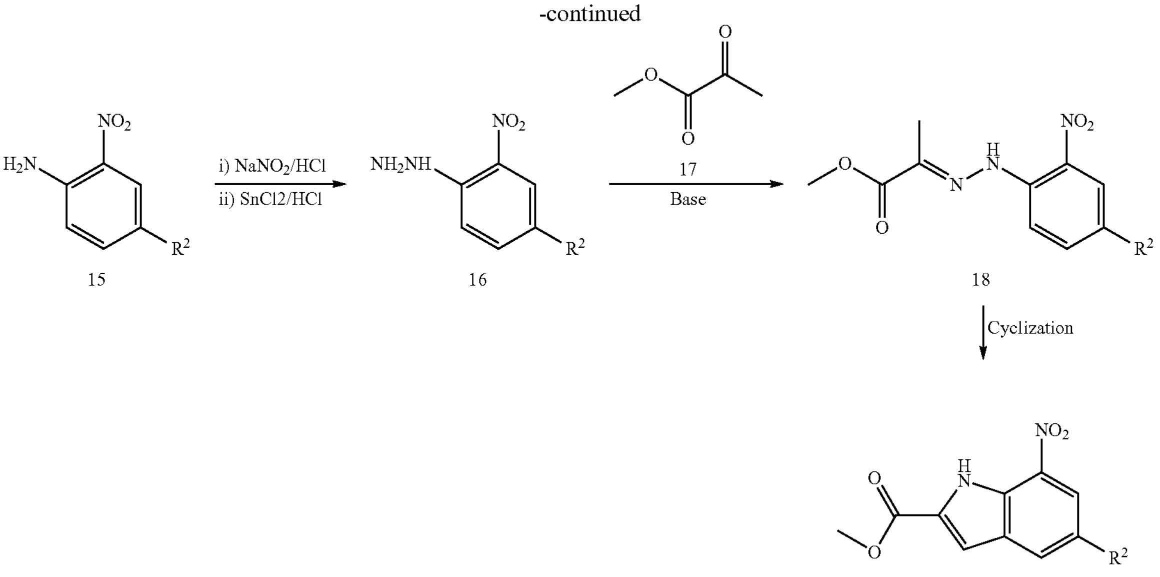

15 16 18 6 in the above Reaction Scheme (5), $R^2$ is as defined above.

The nitro-phenylamine compound (15) is commercially available, or may be prepared according to a process known in Heterocycles, 68(11), 228~599, 2006, or Bioorganic & Medicinal Chemistry Letters, 14(19), 4903~4906, 2004.

The hydrazine compound (16) is also commercially available, or may be prepared by modifying amine group of the compound (15) to hydrazine group according to a process known in Journal of the America Chemical Society, 198(48), 15374~75, 2006.

The hydrazone compound (18) may be obtained by combining the ketone compound (17) with the hydrazine compound (16). A base is not used when the hydrazine compound (16) is a neutral form, but should be used when the compound is an acidic salt form to make it to a neutral form. As the base, metal hydroxides such as sodium hydroxide, lithium hydroxide, etc., matal carbonates such as sodium bicarbonate, potassium carbonate, etc., metal acetates such as sodium acetate, etc., organic bases such as triethylamine, pyridine, etc., preferably sodium acetate, sodium bicarbonate, etc., may be mentioned.

The hydrazone compound (18) may be prepared by reacting diazonium salt with the ketone compound (19) in the presence of a base according to Japp-Klingemann rearrangement method known in Organic Process Research & Development, 2, 1988, 214~220.

The cyclization reaction of the compound (18) may be carried out according to a process known in Journal of Organic Chemistry, 68(24), 2003, 9506~9509, Tetrahedron, 55(34), 1999, 10271~10282, etc. The acid that can be used in this reaction is polyphosphoric acid, hydrochloric acid, p-toluenesulfonic acid, sulfuric acid, acetic acid, etc. In the case of polyphosphoric acid, it may be used alone, or together with an aromatic hydrocarbon selected from benzene, toluene, etc.

The compound that is modified at 5-position of the indole ring may be obtained from the compound (6') as depicted in the following Reaction Scheme (6).

Reaction Scheme 6

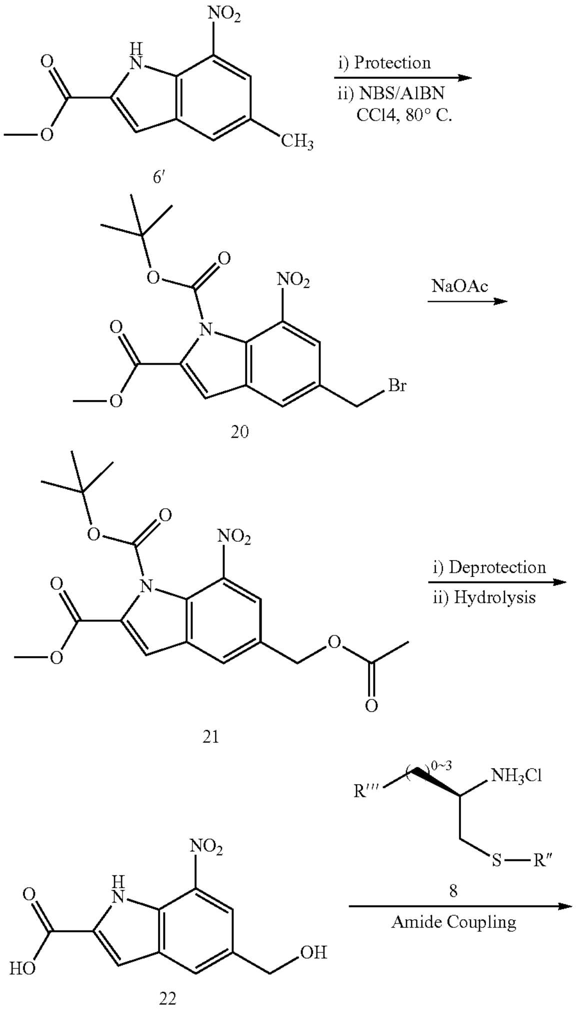

6' 20 21 8 22

-continued

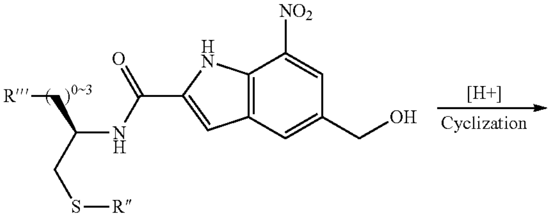

9-2

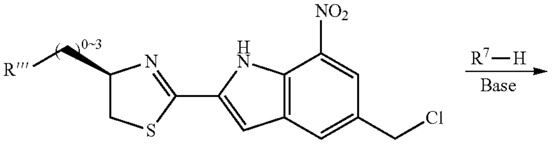

2-6

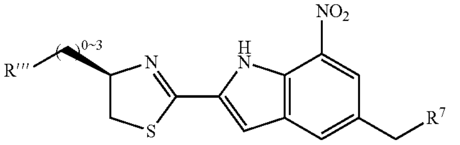

2-7 in the above Reaction Scheme (6),

R", R'" and $R^7$ are as defined above.

The compound (20) may be obtained by protecting the amine group of the (5-methyl-7-nitro-1H-indol-2-yl)carboxylic acid methylester compound (6') using $Boc_2O$ in the presence of a base, and by converting the methyl group at 5-position to bromomethyl group using a brominating agent.

The subsequent acetylation on the compound (20) using sodium acetate, deprotection of BOC group and hydrolysis reaction may give the alcohol compound (22).

A cyclization reaction may be carried out using phosphorus pentachloride on the compound (9-2), which is obtained from the amide coupling reaction between the compounds (22) and (8), as explained for Reaction Scheme (3), to give the compound (2-6) wherein alcohol is replaced with chloride, and the compound (2-6) may be converted to the compound (2-7) by introducing the group $R^7$.

The compound (1-2) having an amine group at 5-position of the indole ring may be obtained by preparing the compound (24) from the phthalimide compound (23) and by acylating the amine group of the compound (1-1), that is obtained from the compound (24), as depicted in the following Reaction Scheme (7).

Reaction Scheme 7

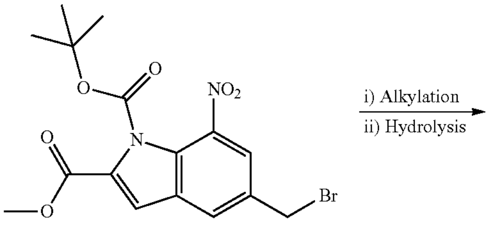

20

-continued

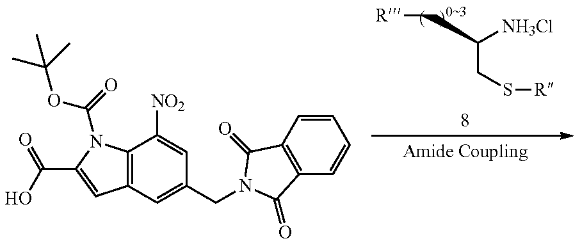

23

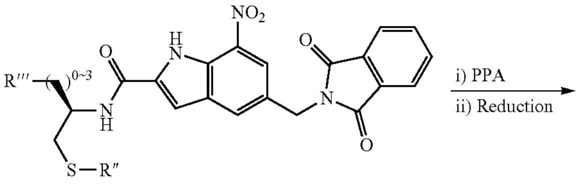

9-3

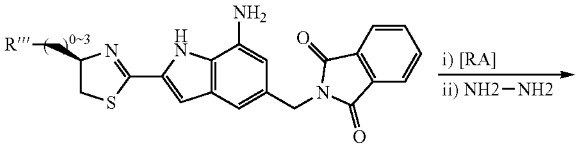

24

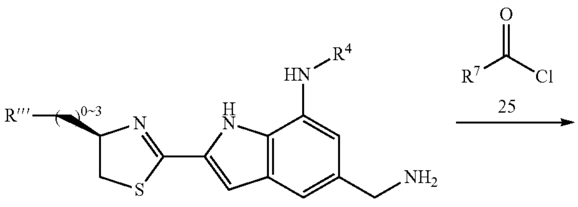

1-1

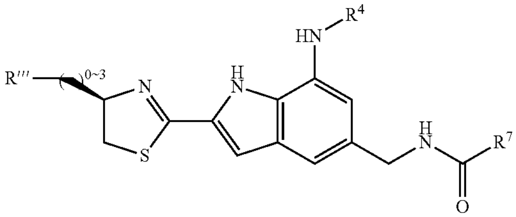

1-2 in the above Reaction Scheme (7), $R^4$, R", R'" and $R^{10}$ are as defined above.

Potassium phthalimide used in the alkylation reaction for introducing phthalimide group is commercially available, and this reaction may be carried out in the presence of tetrahydrofuran, N,N-dimethylformamide, N-methylpyrrolidinone, etc. The hydrolysis reaction may be carried out in the same manner as the process for preparing the compound (2-3) in Reaction Scheme (4). The amide coupling of the compound (23), cyclization and reduction, and the reductive amination of the compound (24) may also be carried out in the same manner as explained above. The reaction for removing phthalimide group of the compound (24) may be carried out using hydrazine. The compound (1-2) may be obtained by acylating the amine compound (1-1) using the acid chloride compound (25), where a base selected from $Et_3N$, DIPEA, DMAP, pyridine, etc. is used typically in an amount of 2 eq. or more with respect to the amine compound.

In the following Reaction Scheme (8), the compounds (8-1) and (8-2) are prepared by protecting thiol group of amino acids such as cysteine, or by introducing thiol group to amino acid derivatives from glutamic acid, aspartic acid, etc.

Reaction Scheme 8

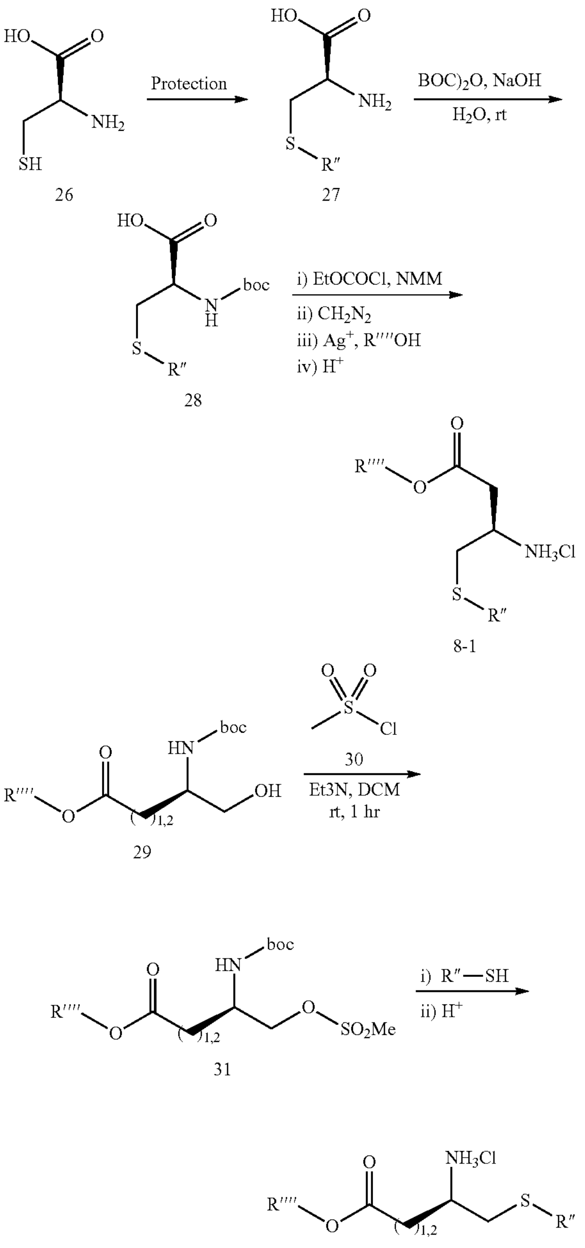

26 27 28 8-1 29 31 8-2 in the above Reaction Scheme (8),

R" is as defined above, and

R""' represents alkyl, preferably methyl, ethyl, isopropyl or cyclohexyl.

The compound (8-1) may be prepared by reacting the amine-protected amino acid compound (28) with diazomethane to give the azo compound, elongating one carbon number using a silver ion such as silver benzoate, esterifying the acid group, and removing the amine protecting group. Specifically, one carbon elongation reaction may be carried out by reacting the compound (28) with ethylchloroformate (EtOCOCl) or isobutylchloroformate ($^{i}$BuOCOCl) in the presence of a base [for example, N-methylmorpholine (NMM), triethylamine, etc.] in tetrahydrofuran solvent at room temperature according to a method known in Helvetica Chimica Acta, 87, 2004, 3131~3159 to give an anhydride, reacting the resulting anhydride with aqueous diazomethane potassium hydroxide solution in diethylether solvent at 0° C. and then with an Ag ion [for example, silver trifluoroacetate ($CF_3CO_2Ag$), silver benzoate, etc.] and an alkyl alcohol (for example, methanol, ethanol, etc.) under the dark condition to give an alkyl ester compound.

In the above reaction, diazomethane may be obtained by reacting Diazald, N-methyl-N-nitrosoguanidine or N-methyl-N-nitrosourea in the presence of KOH base according to the art-known conventional method. The ester compound having one more carbon atom may be obtained from the diazo compound by reacting it with silver benzoate in an alcohol solvent, where the suitable reaction temperature is about −15° C. In order to complete the reaction, the reaction mixture is warmed to room temperature after adding silver benzoate. As the solvent, methanol or ethanol may be used. The BOC group may be removed using trifluoroacetic acid or 4 N hydrochloric acid/ether or hydrochloric acid/dioxane solution.

The amino acid compound (28) whose amine group is protected by BOC may be obtained by protecting the thiol group of cysteine under a base condition, and by protecting the amine group by BOC. Specifically, the protection of thiol group may be carried out using p-methoxybenzylchloride (PMBCl) or triphenylmethylchloride (TrCl) in the presence of a base selected from NaOH, NaH, etc. The BOC protection of amine group may be carried out using $(BOC)_2O$ under a base condition, where the base may include NaOH, $Et_3N$, $NaHCO_3$, etc., and a solvent selected from DCM, dioxane, water, etc. may be used.

The compound (8-2) may be obtained by introducing thiol group to the compound (31), and by removing BOC group therefrom. Specifically, the addition of thiol group may be carried out using PMB-SH (p-methoxybenzylthiol) in the presence of a base selected from NaH, $CeCO_3$, $K_2CO_3$, etc. On the other hand, the compound (31) may be obtained by protecting the alcohol compound (29) using methanesulfonylchloride in the presence of a base $Et_3N$ or DIPEA.

The compound (29) may be synthesized from the starting compound glutamic acid or aspartic acid according to a method known in Synlett, 15, 2005, 2397~2399 or Journal of Organic Chemistry, 66(5), 2001, 1919·1923, etc.

In the following Reaction Scheme (9), the carboxylic acid moiety of the cysteine derivative (28) is modified to give the compound (11).

Reaction Scheme 9

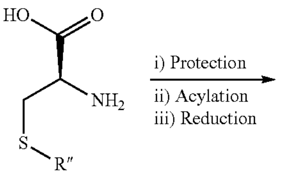

28

-continued

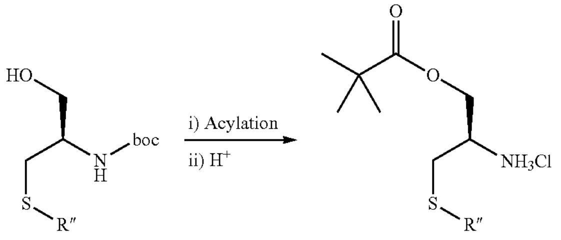

32

11 in the above Reaction Scheme (9), R" is as defined above.

The protection of amine group of the compound (28) may be conducted using $(BOC)_2O$, the acylation may be carried out using isobutyric acid chloride, t-butyric acid chloride, etc. in the presence of a base, and the reduction may be carried out using $NaBH_4$.

The acylation of the compound (32) is carried out using pivaloyl chloride in the presence of a base, and the removal of BOC is carried out as explained above.

The compounds whose preparation methods are not specifically explained in the present specification are known per se, or those that can be prepared from a known compound according to a known process or a similar process thereto.

In the processes according to the present invention, mixtures are conventionally separated by column chromatography. In the case of a final product, it can be separated after completion of reaction by recrystallization or normal or reverse-phased HPLC (Waters, Delta Pack, 300×50 mmI.D., C18 5 μm, 100 A). When the product is purified by recrystallization or HPLC, the compound may be obtained in the form of a salt with trifluoroacetic acid. When a salt with hydrochloric acid is desirable, ion exchange resin can be used.

As explained above, the compounds according to the present invention, starting materials, intermediates, etc. for the preparation thereof may be obtained by various processes, and such processes for preparing the compounds of formula (I) should be construed to fall under the scope of the present invention.

Effect

The present invention further provides a composition for the prevention or treatment of necrosis and associated diseases, which comprises therapeutically effective amount of the compounds of formula (I), pharmaceutically acceptable salts or isomers thereof as an active ingredient together with pharmaceutically acceptable carriers or diluents.

The present invention further provides a method for the prevention or treatment of necrosis and associated diseases using the above described composition.

Necrosis and associated diseases which can be treated and/or prevented according to the present invention include acute/chronic hepatic disease (e.g. hepatitis, hepatic fibrosis, hepatocirrhosis), neurodegenerative disease (e.g. dementia, Parkinson's disease, Huntington's disease), ischemic cardiac disease, reperfusion injury, ischemic stroke or ischemic injury, pancreatitis, bacterial/viral sepsis, diabetes mellitus or diabetic complications, diabetic vascular disease [in particular, these diabetes are caused by pancreatic cell destroying substances, and mediated by virus, hyperglycemia, fatty acid, diet, toxin, streptozotocin and the like], necrotizing procolitis, cystic fibrosis, rheumatoid arthritis, degenerative arthritis, nephropathy, bacterial infection, viral infection (e.g. HIV), multiple sclerosis, leukemia, lymphoma, neonatal respiratory distress syndrome, asphyxia, tuberculosis, endometriosis, angiasthenia, psoriasis, chilblain, steroid treatment complications, gangrene, pressure sores, hemoglobinuria, burns, hyperthermia, Crohn's disease, celiac disease, compartment syndrome, spiral cord injury, glomerulonephritis, muscular dystrophy, metabolic inherited disease, mycoplasmal disease, anthrax, Andersen's disease, congenital mitochondrial disease, phenylketonuria, placental infarction, syphilis, aseptic necrosis etc. In addition, necrosis and associated diseases caused by drugs and toxic substances are selected from the group consisting of the necrosis associated with alcoholism, the exposure to, and/or administration and/or self-administration of, cocaine, drugs (e.g., paracetamol), antibiotics, anti-cancer agent, adriamycin, puromycin, bleomycin, NSAID, cyclosporine, chemical toxins (e.g., carbon tetrachloride, cyanide, methanol, ethylene glycol), poison gas, agrochemicals, heavy metals (e.g., lead, mercury, cadmium), or injury due to the exposure to radioactivity/UV and associated necrosis thereof.

In particular, the composition according to the present invention exhibits not only the effects for hepatoprotection and hepatic functional improvement, but also shows the prophylactic and therapeutic effects on the chronic hepatic disease such as fatty liver, hepatic fibrosis, hepatocirrhosis, etc. and acute/chronic hepatic disease such as hepatitis, etc. caused by virus or drugs. Consequently, complications of hepatic disease including, but not limited to, portal hypertension also may be prevented or treated. More particularly, the medical composition according to the present invention is also effective for the treatment or prevention of the hepatic disease selected from liver transplantation, alcoholic or non-alcoholic fatty liver, hepatic fibrosis, hepatocirrhoisis and hepatitis caused by virus or drugs, and is effective for alcoholic acute/chronic hepatic disease.

Further, the composition according to the present invention is effective for the treatment or prevention of fatty acid-induced fatty liver or acute/chronic hepatic disease derived from fatty liver.

As used herein, "treatment" means the interrupting or delaying the progress of the disease when applied to the subject showing the onset of disease symptoms, and "prevention" means the interrupting or delaying the sign of the onset of disease when applied to the subject that does not show, but is at risk of, the onset of disease symptoms.

The above-mentioned "pharmaceutical composition" may comprise pharmaceutically acceptable carriers, diluents, excipients, or their combinations, if needed, together with the compounds of the present invention. Pharmaceutical composition facilitates the administration of the compound into a living organism. There exist a number of techniques to administer the compound, and they include, but not limited to, oral, injectable, aerosol, parenteral and topical administration.

As used herein, "carrier" means a substance which facilitates the incorporation of the compound into the cells or tissues. For example, dimethylsulfoxide (DMSO) is a typical carrier which is used to facilitate the introduction of various organic compounds into the cells or tissues of living organisms.

As used herein, "diluent" is defined as a substance that is diluted in water which dissolves the compound, as well as stabilizes the biologically active form of the subject compound. The salts dissolved in buffer solution are utilized as diluents in the art. Typically used buffer solution is phosphate buffered saline which mimics the salt form of human solution.

Buffer diluents rarely alter the biological activities of the compound, as the buffer salts can control the pH of solution at low concentration.

As used herein, “pharmaceutically acceptable” means the property that does not impair the biological activities and physical properties of the compound.

The compounds of the present invention can be formulated as various pharmaceutical dosage forms according to the desired purpose. For the preparation of the pharmaceutical composition of the present invention, active ingredient, specifically, the compounds of formula (I), pharmaceutically acceptable salts or isomers thereof are mixed together with various pharmaceutically acceptable carriers which can be selected according to the formulation to be prepared. For example, the pharmaceutical composition of the present invention can be formulated as injectable preparation, oral preparation, etc., according to the desired purpose.

The compounds of the present invention can be formulated by the methods known in the art, which utilize pharmaceutical carriers and excipients known in the art, and be incorporated into the containers of unit dose form or mult-dose form. The form of the preparation can be solutions, suspensions or emulsions in oily or aqueous media, and contain typical dispersing agents, suspending agents or stabilizers. Further, for example, it can be a form of dry powder which is intended to be reconstructed by dissolving in sterile, pyrogen-free water prior to use. The compounds of the present invention also can be formulated into suppository forms utilizing typical suppository base such as cocoa butter or other glycerides. As solid dosage forms for oral administration, capsules, tablets, pills, powder and granule can be prepared, and capsules and tablets are especially useful. Preferably, tablets and pills are prepared as enteric coated forms. Solid dosage forms can be prepared by mixing the compounds of the present invention together with carriers such as one or more inert diluents such as sucrose, lactose, starch, etc., lubricants such as magnesium stearate, disintegrants, binders, etc.

If needed, the compounds of the present invention or the pharmaceutical compositions containing the same can also be administered in combination with other active agents including cytoprotective agents with various action mechanisms of different types, especially the existing agents utilized for hepatoprotection, hepatic functional improvement, and prevention or treatment of hepatic disease—hepatocyte regeneration promoters, hepatic functional adjuvants, anti-viral agents, immunosuppressants, fibrosis inhibitors, etc.

The compounds of the present invention or the pharmaceutical compositions containing the same can be co-administered with prophylactic or therapeutic agents for any drug-derived necrosis and associated diseases. These drugs include the drugs for any disease group, such as antibiotics, anti-cancer agents, anti-viral agents, anti-infectives, anti-inflammatory agents, anti-coagulants, lipid-improving agents, cell death inhibitors, anti-hypertensive agents, anti-diabetic/anti-obesity agents, therapeutic agents for cardiovascular disease, therapeutic agents for neurodegenerative disease, anti-aging agents, therapeutic agents for metabolic disease, etc.

The compounds of the present invention or the pharmaceutical compositions containing the same can be used for the prevention of the cell injury and subsequent necrosis and associated diseases derived by various causes such as toxins, and these causes include reactive oxygen species (ROS), heavy metals, alcohol, food, supplement, radiation, diet, etc.

The dosage of the compounds of formula (I) depends on the prescription of a physician, taking into account such factors as body weight, sex, age, condition of health, and diet of the patient, specific nature of the disease, administration time of the agent, administration method, mixing ratio of agents, and severity of the disease, etc. However, dosage needed for the treatment of an adult is typically from about 1.0 mg to 2,000 mg per day, depending on the intensity and frequency of the administration. When administered to an adult via intramuscular or intravenous routes, total dosage typically from about 1.0 mg to 300 mg per day will be sufficient when separately administered in a single dosage, but for some patients a higher daily dosage may be desirable.

The present invention further provides a method of preparing the composition for the prevention or treatment of necrosis and associated diseases, which comprises the step of mixing the compounds of formula (I), pharmaceutically acceptable salts or isomers thereof as an active ingredient together with pharmaceutically acceptable carriers or diluents.

BEST MODE FOR CARRYING OUT THE INVENTION

The present invention will be more specifically explained by the following preparations and examples. However, it should be understand that they are intended to illustrate the present invention but not in any manner to limit the scope of the present invention. In the following preparations and examples, M means molar concentration, and N means normal concentration.

The following Preparations explain more in detail preparations of intermediates that are required for syntheses of Example compounds. The abbreviations used in the following Preparations and Examples are as follows.

Ac: acetyl
AIBN: 2,2'-azobis(2-methylpropionitrile)
BOC: t-butoxycarbonyl
Bu: butyl
Bn: benzyl
c-Pen: cyclopentyl
c-Hex: cyclohexyl
CBZ(Cbz): benzyloxycarbonyl
DME: dimethoxyethane
DCM: dichloromethane
DIPEA: diisopropylethylamine
DMAP: 4-dimethylaminopyridine
DMF: N,N-dimethylformamide
EDC: 1-(3-dimethylaminopropyl)-3-ethylcarbodiimide, hydrochloride
Et: ethyl
EtOAC: ethyl acetate
Hex: n-hexane
HOBT: hydroxybenzotriazole
HBTU: 2-(1H-benzotriazol-1-yl)-1,1,3,3-tetramethyluronium hexafluoro-phosphate
i-Pr: isopropyl
i-Pen: isopentyl
Me: methyl
Ph: phenyl
Pid: piperidine
Piz: piperazine
Pyd: pyrrolidine
PMB: paramethoxybenzyl
TEA: triethylamine
TFA: trifluoroacetic acid
THF: tetrahydrofuran
THP: tetrahydropyran
t-Bu: t-butyl Preparation 1: 4-(Pyridin-3-yloxy)phenylamine Step A: 4-(Pyridin-3-yl)oxy-1-nitrobenzene 1-Chloro-4-nitrobenzene (40 g, 0.25 mol) and 3-hydroxypyridine (36 g, 0.38 mol) were dissolved in N,N-dimethylformamide (100 mL). Potassium carbonate (52.6 g, 0.38 mol) was added thereto, and the mixture was stirred for 20 h at 100° C. After completion of the reaction, water was added. The reaction mixture was extracted with ethyl acetate, washed with saturated sodium chloride solution, and dried over anhydrous magnesium sulfate to give the title compound.

Step B: 4-(Pyridin-3-yloxy)phenylamine 4-(Pyridin-3-yl)oxy-1-nitrobenzene prepared in Step A was dissolved in the mixture of water (100 mL), tetrahydrofuran (100 mL) and methanol (100 mL). Iron powder (103 g, 1.84 mol) and ammonium chloride (99 g, 1.84 mol) were added thereto, and the mixture was stirred for 3 h at 80° C. using a mechanical stirrer. After completion of the reaction, the reaction mixture was filtered through a cellite, washed with methanol, and concentrated under reduced pressure. The solid thus obtained was filtered, washed with ether, and dried to give the title compound (17 g, Yield 36%).

Mass [M+H]: 186 (M+1)

Preparation 2: 4-(4-Methanesulfonyl-phenoxy)phenylamine

Step A: 1-(4-Methylsulfanylphenoxy)-4-nitrobenzene

1-Chloro-4-nitrobenzene (15 g, 95 mmol) and 4-(methylmercapto)phenol (13.3 g, 95 mmol) were dissolved in dimethylsulfoxide (100 mL). Potassium carbonate (15.8 g, 134 mmol) was added thereto, and the mixture was stirred for 12 h at 100° C. After completion of the reaction, excess water was added to precipitate a solid, which was then filtered and dried to give the title compound.

Step B: 4-(4-Methanesulfonyl-phenoxy)nitrobenzene 1-(4-Methylsulfanylphenoxy)-4-nitrobenzene (86 g, 330 mmol) prepared in Step A was dissolved in dichloromethane (500 mL). mCPBA (3-chloroperbenzoic acid) (83 g, 330 mmol) was added thereto, and the mixture was stirred for 2 h at 0° C. to room temperature. After completion of the reaction, excess 6N aqueous sodium hydroxide solution was added. The reaction mixture was extracted with ethyl acetate and dichloromethane, washed with saturated sodium chloride solution, and dried over anhydrous magnesium sulfate to give the title compound (28 g, Yield 100%).

Step C: 4-(4-Methanesulfonyl-phenoxy)phenylamine 4-(4-Methanesulfonyl-phenoxy)nitrobenzene (28 g, 95 mmol) prepared in Step B was dissolved in methanol (500 mL) and ethyl acetate (500 mL). 10% Pd/C (1.0 g) was added thereto, and the mixture was stirred under hydrogen gas of atmospheric pressure for 3 h. After completion of the reaction, the reaction mixture was filtered through a cellite, washed with methanol, concentrated under reduced pressure, and dried over anhydrous magnesium sulfate to give the title compound (25 g, Yield 100%).

Mass[M+H]: 263 (M+1)

Preparation 3: 4-Ethoxy-2-nitro-phenylamine

Step A: 4-Ethoxy-1-acetylaminobenzene

4-Ethoxyaniline (40 g, 0.29 mol) and triethylamine (61 mL, 0.44 mol) were dissolved in dichloromethane (200 mL). Acetic anhydride (30 mL, 0.32 mol) was added in drops thereto, and the mixture was stirred for 1 h at 0° C. to room temperature. 1N hydrochloric acid solution was added, and the reaction mixture was extracted with ethyl acetate, washed with sodium chloride solution, and dried over anhydrous magnesium sulfate to give the title compound.

Step B: 4-Ethoxy-2-nitro-1-phenylamine

4-Ethoxy-1-acetylaminobenzene (51 g, 0.29 mol) prepared in Step A was dissolved in dichloromethane (200 mL). Fuming nitric acid (13 mL, 0.29 mol) was added in drops thereto at 0° C., and the mixture was stirred for 1 h at 0° C. to room temperature. Saturated aqueous sodium hydrogen carbonate solution was added to the reaction mixture, which was then extracted with ethyl acetate, washed with saturated sodium chloride solution, and dried over anhydrous magnesium sulfate. The resulting nitro compound was dissolved in methanol (100 mL) and tetrahydrofuran (100 mL). 6N sodium hydride was added in drops thereto, and the mixture was stirred for 6 h at room temperature. After completion of the reaction, the reaction mixture was neutralized to about pH 7 using 6N hydrochloric acid solution, extracted with ethyl acetate, washed with saturated sodium chloride solution, and dried over anhydrous magnesium sulfate to give the title compound (44 g, Yield 83%).

Mass [M+H]: 182 (M+1)

Preparations 4 to 13

The phenylamine compounds prepared in Preparations 1 and 2 and the commercially available anilines were reacted according to the same procedure as Preparation 3 to synthesize the Preparation Compounds in the following table.

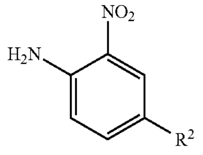

| Preparation | $R^2$ | Mass [M + H] |
|---|---|---|
| 4 | —O—(pyridin-3-yl) | 231 |
| 5 | —O—(4-methanesulfonylphenyl) | 308 |
| 6 | methoxy | 168 |
| 7 | phenoxy | 231 |
| 8 | fluoro | 156 |
| 9 | bromo | 217 |
| 10 | NAc | 195 |
| 11 | —O—(n-Pr) | 196 |
| 12 | —O—CF3 | 222 |
| 13 | chloro | 172 |

Preparation 14: 5-Chloro-7-nitro-1H-indole-2-carboxylic acid methyl ester

<Method A>

Step A: (4-Chloro-2-nitro-phenyl)hydrazine hydrochloride

4-Chloro-2-nitroaniline (40 g, 0.23 mol) prepared in Preparation 13 was dissolved in 12N hydrochloric acid (100 mL). Sodium nitrite (16 g, 0.23 mol) dissolved in water (50 mL) was slowly added in drops thereto at 0° C., and the mixture was stirred for 30 min at 0° C. to room temperature. The reaction mixture was cooled to 0° C., tin (II) chloride (132 g, 0.70 mol) dissolved in 12N hydrochloric acid (100 mL) was slowly added in drops thereto, and the mixture was stirred for 3 h at 0° C. to room temperature. The resulting yellow solid was filtered, washed with a small amount of 6N HCl, and dried to give the title compound (30 g, Yield 63%).

$^1$H-NMR (400 HMz, DMSO-$d_6$); δ 9.21(s, 1H), 7.98(d, J=2.4 Hz, 1H), 7.66(d, J=9.6 Hz, 1H), 7.55(dd, J=2.4, 9.6 Hz, 1H), 4.74(br s, 2H)

Step B: 2-[(4-Chloro-2-nitro-phenyl)hydrazono]propionic acid methyl ester (4-Chloro-2-nitro-phenyl)hydrazine hydrochloride (30 g, 0.14 mol) prepared in Step A and methyl pyruvate (14.4 mL, 0.16 mol) were dissolved in methanol (300 mL), and sodium acetate (14.2 g, 0.17 mol) was added thereto. The reaction solution was stirred for 8 h at room temperature, and the resulting yellow solid was filtered, washed with water and methanol, and dried to give the title compound (30 g, Yield 82%).

$^1$H-NMR (400 HMz, $CDCl_3$); δ 10.88(s, 1H), 8.21(d, J=2.4 Hz, 1H), 8.01(d, J=9.2 Hz, 1H), 7.56(dd, J=2.4, 9.2 Hz, 1H), 3.90(s, 3H), 2.23(s, 3H).

Step C: 5-Chloro-7-nitro-1H-indole-2-carboxylic acid methyl ester

To 2-[(4-chloro-2-nitro-phenyl)hydrazono]propionic acid methyl ester (13 g, 46 mmol) prepared in Step B was added polyphosphoric acid (100 mL), and the mixture was heated for 4 h at 100° C. After completion of the reaction, water was added to the reaction mixture at 0° C. The resulting mixture was stirred for 2 h, and filtered to collect the solid. The solid was washed with water, and dried to give the title compound (6.0 g, Yield 49%).

$^1$H-NMR (400 HMz, $CDCl_3$); δ 10.32(br s, 1H), 8.29(d, 1H), 8.03(d, J=2.4 Hz, 1H), 7.31(d, J=2.0 Hz, 1H), 4.01(s, 3H)

<Method B>

Step A: 2-[(4-Chloro-2-nitro-phenyl)-hydrazono]-propionic acid methyl ester

4-Chloro-2-nitro-phenylamine (11.0 g, 64.05 mmol) prepared in Preparation 13 was dissolved in conc. hydrochloric acid (32 mL) in flask A, and cooled to −10° C. Ice (90 g) was added, sodium nitrite (4.42 g, 64.05 mmol) dissolved in water (50 mL) was slowly added, and the mixture was stirred until it became transparent.

2-Methyl-3-oxo-butyric acid methyl ester (8.32 g, 64.05 mmol) was dissolved in ethanol (76 mL) in flask B, and cooled to −10° C. Potassium hydroxide (19.05 mL) dissolved in water (19 mL) was added thereto, to which was added the solution prepared in flask A at −10° C. The mixture was stirred for 1 h. The resulting red solid was filtered to give the title compound (7.54 g, Yield 46%).

Step B: 5-Chloro-7-nitro-1H-indole-2-carboxylic acid methyl ester

2-[(4-Chloro-2-nitro-phenyl)-hydrazono]-propionic acid methyl ester prepared in Step A was reacted according to the same procedure as Step C of <Method A> of Preparation 14 to give the title compound.

$^1$H-NMR (400 HMz, $CDCl_3$); δ 10.32(br s, 1H), 8.29(d, 1H), 8.03(d, J=2.4 Hz, 1H), 7.31(d, J=2.0 Hz, 1H), 4.01(s, 3H)

Preparations 15 to 26

The compounds of Preparations were reacted with methyl pyruvate, ethyl pyruvate, 2-methyl-3-oxo-butyric acid methyl ester or 2-methyl-3-oxo-butyric acid ethyl ester according to Method A or B of Preparation 14 to synthesize the Preparation Compounds in the following table.

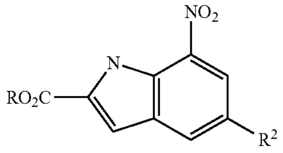

| Preparation | R | $R^2$ | $^1$H-NMR |
|---|---|---|---|
| 15 | methyl | methyl | (500 HMz, DMSO-$d_6$); δ 11.25 (br s, 1H), 8.08 (3, 1H), 7.96 (s, 1H), 7.32 (s, 1H), 3.87 (s, 3H), 2.44 (s, 3H) |
| 16 | methyl | methoxy | (400 HMz, DMSO-$d_6$); δ 11.26 (br s, 1H), 7.84 (s, 1H), 7.80 (s, 1H), 7.35 (s, 1H), 3.91 (s, 3H), 3.89 (s, 3H) |
| 17 | methyl | hydrogen | $^1$H-NMR (500 HMz, DMSO-$d_6$); δ 11.36 (br s, 1H), 8.23 (d, 1H), 8.17 (d, 1H), 7.42 (s, 1H), 7.32 (t, 1H), 3.88 (s, 3H) |
| 18 | ethyl | fluoro | (400 HMz, DMSO-$d_6$); δ 11.55 (br s, 1H), 8.16 (m, 1H), 8.10 (m, 1H), 7.42 (s, 1H), 4.40 (q, 2H), 1.36 (t, 3H) |

-continued

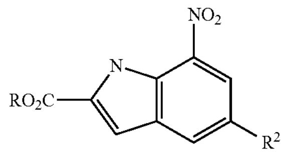

| Preparation | R | $R^2$ | $^1$H-NMR |
|---|---|---|---|
| 19 | ethyl | ethoxy | (400 HMz, DMSO-$d_6$); δ 10.20 (br s, 1H), 7.86 (s, 1H), 7.51 (s, 1H), 7.26 (s, 1H), 4.13 (m, 2H), 3.98 (s, 3H), 1.47 (m, 3H) |
| 20 | methyl | bromo | (400 HMz, $CDCl_3$); δ 10.33 (br s, 1H), 8.4 1(s, 1H), 8.18 (s, 1H), 7.30 (d, J = 4.0 Hz, 1H), 4.01 (s, 3H) |
| 21 | methyl | phenoxy | (400 HMz, $CDCl_3$); δ 10.26 (br s, 1H), 8.05 (s, 1H), 7.69 (s, 1H), 7.39 (m, 2H), 7.26 (s, 1H), 7.15 (m, 1H), 7.01 (m, 2H), 4.00 (s, 3H) |
| 22 | ethyl | —O—(4-methane-sulfonyl) | (400 HMz, DMSO-$d_6$); δ 8.099s, 1H), 10.20 (br s, 1H), 7.86 (s, 1H), 7.51 (s, 1H), 7.26 (s, 1H), 4.13 (m, 2H), 3.98 (s, 3H), 1.47 (m, 3H) |
| 23 | ethyl | —O—(pyridin-3-yl) | $^1$H-NMR (400 HMz, $CDCl_3$); δ 10.32 (br s, 1H), 8.51~8.47 (m, 2H), 8.05(d, J = 2.4 Hz, 1H), 7.73 (d, J = 2.0 Hz, 1H), 7.42~7.35 (m, 2H), 7.31 (d, J = 2.4 Hz, 1H), 4.48 (q, 2H), 1.47 (t, 3H) |
| 24 | ethyl | —O—(n-Pr) | (400 HMz, DMSO-$d_6$); δ 10.12 (brs, 1H), 7.92 (s, 1H), 7.51 (s, 1H), 7.24 (s, 1H), 4.44 (m, 2H), 4.01 (m, 2H), 1.91 (m, 2H), 1.44 (m, 3H), 1.08 (m, 3H) |
| 25 | ethyl | —O—$CF_3$ | (400 HMz, DMSO-$d_6$); δ 10.34 (br s, 1H), 7.91 (s, 1H), 7.80 (s, 1H), 7.45 (s, 1H), 4.34 (m, 2H), 1.45 (m, 3H) |
| 26 | ethyl | NAc | (400 HMz, DMSO-$d_6$); δ 11.26 (s, 1H), 10.31 (s, 1H), 8.55 (s, 1H), 8.44 (s, 1H), 7.45 (s, 1H), 4.40 (q, 2H), 2.11 (s, 3H), 1.36 (t, 3H) |

Preparation 27: (R)-3-amino-4-(4-methoxy-benzylsulfanyl)-butyric acid methyl ester hydrochloride

Step A: (R)-2-amino-3-(4-methoxy-benzylsulfanyl)-propionic acid

4-Methoxybenzyl alcohol (280 g, 1780 mmol) dissolved in diethylether (400 mL) was added in drops to a mixture of diethylether (400 mL) and conc. hydrochloric acid (400 mL) over 2 h, and the mixture was stirred for 1 h. The organic layer was separated, and added to a solution prepared by dissolving L-cysteine (197 g, 1625 mmol) and 2N aqueous sodium hydroxide solution (980 mL) to ethanol (1890 mL). The mixture was stirred for 2 h at room temperature. After completion of the reaction, the reaction mixture was cooled to 0° C., and neutralized to pH 7 using 3N aqueous hydrochloric acid solution. The resulting solid was filtered and dried to give the title compound (250 g, Yield 64%).

Step B: (R)-2-BOC-amino-3-(4-methoxy-benzylsulfanyl)-propionic acid (R)-2-amino-3-(4-methoxy-benzylsulfanyl)-propionic acid (30.7 g, 127.3 mmol) prepared in Step A was dissolved in tetrahydrofuran (150 mL) and water (150 mL). Potassium carbonate (26.4 g, 190 mmol) and $(BOC)_2O$ (27.7 g, 127.3 mmol) were added thereto, and the mixture was stirred for 2 h at room temperature. After completion of the reaction, the reaction mixture was distilled under reduced pressure to remove tetrahydrofuran. The residue was cooled to 0° C., and acidfied to pH 3 using 3N aqueous hydrochloric acid solution. The resulting solid was washed with water and dried to give the title compound (43 g, Yield 99%).

Step C: [(R)-3-diazo-1-(4-methoxy-benzylsulfanylmethyl)-2-oxo-propyl]-carbamic acid t-butyl ester (R)-2-BOC-amino-3-(4-methoxy-benzylsulfanyl)-propionic acid (43 g, 132 mmol) prepared in Step B, 1-methylmorpholine (14.5 mL, 132 mmol) and ethylchloroformate (14.1 mL, 132 mmol) were dissolved in tetrahydrofuran (500 mL), and the mixture was stirred for 1 h at −25° C. At the same time, potassium hydroxide (75 g, 1336 mmol) was dissolved in water (75 mL) and diethylether (750 mL), N-methyl-nitrosourea (26 g, 252 mmol) was added in drops thereto over 2 h at 0° C., and the mixture was stirred for 30 min. The two solutions thus obtained were mixed together, and stirred for 3 h at −25° C. to room temperature. After completion of the reaction, water was added to the reaction mixture, which was then washed with saturated aqueous sodium hydrogen carbonate solution and saturated aqueous ammonium chloride solution in the order. The organic layer was concentrated to give the title compound (46.0 g, Yield 95%).

$^1$H-NMR (400 HMz, $CDCl_3$); δ 7.25(d, J=8.8 Hzm 2H), 6.86(d, J=8.8 Hz, 2H), 5.48(br s 1H), 5.29(m, 1H), 4.31(m, 1H), 3.79(s, 3H), 3.69(s, 2H), 2.76(d, J=6.0 Hz, 2H), 1.45(s, 9H)

Step D: (R)-3-t-butoxycarbonylamino-4-(4-methoxy-benzylsulfanyl)-butyric acid methyl ester

[(R)-3-diazo-1-(4-methoxy-benzylsulfanylmethyl)-2-oxo-propyl]-carbamic acid t-butyl ester (40 g, 109 mmol)

prepared in Step C was dissolved in methanol (600 mL), and the mixture was cooled to −25° C. Silver trifluoroacetate was added thereto, and the mixture was slowly warmed. After completion of the reaction, the solid moiety was removed by a cellite filtration. Saturated aqueous $NH_4Cl$ solution was added, and the mixture was extracted with EtOAc, and dried over $MgSO_4$. The solvent was removed under reduced pressure, and the residue was purified by column chromatography (eluent: EtOAc/n-Hex=1/3) to give the title compound (30.6 g, Yield 76%).

$^1$H-NMR (500 HMz, $CDCl_3$); ═ 7.24(d, J=8.6 Hz, 2H), 6.83(d, J=8.6 Hz, 2H), 5.09(m, 1H), 4.08(m, 1H), 3.79(s, 3H), 3.68(s, 2H), 3.66(s, 3H), 2.70~2.52(m, 4H), 1.44(s, 9H)

Step E: (R)-3-amino-4-(4-methoxy-benzylsulfanyl)-butyric acid methyl ester (R)-3-t-butoxycarbonylamino-4-(4-methoxy-benzylsulfanyl)-butyric acid methyl ester (30 g, 81.3 mmol) prepared in Step D was dissolved in dichloromethane (70 mL). 4N hydrochloric acid/1,4-dioxane solution (71 mL) was added thereto, and the mixture was stirred for 2 h at room temperature. After completion of the reaction, the reaction solution was concentrated under reduced pressure. To the residue were added dichloromethane (30 mL) and diethylether (150 mL). The resulting solid was filtered and dried to give the title compound (19.2 g, Yield 87%).

$^1$H NMR (400 MHz, DMSO-$d_6$); δ 8.21(br s, 3H), 7.25(d, 2H), 6.83(d, 2H), 3.78(s, 3H), 3.68(s, 2H), 3.65(s, 3H), 3.29 (m, 1H), 2.51-2.48(m, 2H), 2.35-2.31(m, 2H)

Preparation 28: Ethyl (R)-3-amino-4-(4-methoxy-benzylsulfanyl)-butyrylate hydrochloride

[(R)-3-diazo-1-(4-methoxy-benzylsulfanylmethyl)-2-oxo-propyl]-carbamic acid t-butyl ester prepared in Step C of Preparation 27 and ethanol were reacted according to the same procedures as Steps D and E of Preparation 27 sequentially to give the title compound.

$^1$H NMR (400 MHz, $CDCl_3$); δ 8.37(br s, 3H), 7.28(d, J=8.0 Hz, 2H), 6.87(d, J=8.0 Hz, 2H), 4.11(m, 2H), 3.73(s, 3H), 3.70(s, 2H), 2.81~2.67(m, 4H), 1.18(t, 3H)

Preparation 29: (R)-4-amino-5-(4-methoxy-benzylsulfanyl)-pentanoic acid ethyl ester hydrochloride Step A: (R)-4-BOC-amino-5-hydroxy-pentanoic acid ethyl ester Commercially available (R)-2-BOC-amino-pentanoic acid-5-ethylester-1-methylester (57.8 g, 200 mmol) was dissolved in methanol (200 mL). $LiBH_4$ (1N THE solution, 400 mL) was added thereto, and the mixture was stirred for 2 h while maintaining the temperature at 10° C. or lower. After completion of the reaction, the reaction mixture was cooled to 0° C., and water was slowly added thereto to quench the reaction. Methanol was removed under reduced pressure, and the residue was diluted with saturated aqueous $NaHCO_3$ solution. The mixture was extracted with EtOAc, and dried over $MgSO_4$. The solvent was removed under reduced pressure, and the residue was purified by column chromatography to give the title compound (39 g, Yield 75%).

Step B: (R)-4-BOC-amino-5-methanesulfonyloxy-pentanoic acid ethyl ester (R)-4-BOC-amino-5-hydroxy-pentanoic acid ethyl ester (36 g, 137.8 mmol) prepared in Step A and triethylamine (38.4 mL, 275.5 mmol) were dissolved in dichloromethane (200 mL). Methanesulfonylchloride (11.7 mL, 151.5 mmol) was added in drops thereto, and the mixture was stirred for 1 h at 0° C. to room temperature. After completion of the reaction, 1N hydrochloric acid solution was added, which was then extracted with ethyl acetate, washed with saturated aqueous sodium chloride solution, and dried over anhydrous magnesium sulfate to give the title compound.

Step C: (R)-4-BOC-amino-5-(4-methoxy-benzylsulfanyl)-pentanoic acid ethyl ester

Sodium hydride (5.5 g, 137.8 mmol) and 4-methoxybenzylmercaptan (15.4 mL, 110.2 mmol) were dissolved in N,N-dimethylformamide (150 mL), and the mixture was stirred for 10 min at 0° C. To the resulting solution was added in drops (R)-4-BOC-amino-5-methanesulfonyloxy-pentanoic acid ethyl ester (46.7 g, 137.8 mmol) prepared in Step B, and the mixture was stirred for 4 h at 0° C. Water was added thereto to quench the reaction, and the reaction mixture was extracted with ethyl acetate, washed with saturated aqueous sodium chloride solution, and dried over anhydrous magnesium sulfate. The solvent was removed under reduced pressure, and the residue was purified by column chromatography to give the title compound.

$^1$H-NMR (400 HMz, $CDCl_3$); δ 7.25(d, J=8.8 Hz, 2H), 6.85(d, J=8.8 Hz, 2H), 4.56(m, 1H), 4.12(m, 2H), 3.79(s, 3H), 3.69(s, 2H), 2.53(m, 2H), 2.33(t, 2H), 1.93(m, 1H), 1.70(m, 1H), 1.44(s, 9H), 1.25(t, 3H)

Step D: (R)-4-amino-5-(4-methoxy-benzylsulfanyl)-pentanoic acid ethyl ester hydrochloride (R)-4-BOC-amino-5-(4-methoxy-benzylsulfanyl)-pentanoic acid ethyl ester (11 g, 62.7 mmol) prepared in Step C was dissolved in dichloromethane (200 mL). 4N hydrochloric acid/ethyl acetate solution (20 mL) was added thereto, and the mixture was stirred for 2 h at room temperature. After completion of the reaction, the solvent was thoroughly removed under reduced pressure. The residue was recrystallized from diethylether (150 mL), and dried to give the title compound (20 g, Yield 96%).

$^1$H NMR (400 MHz, DMSO-$d_6$); δ 8.69(br s, 3H), 7.29(d, J=8.0 Hz, 2H), 6.89(d, J=8.0 Hz, 2H), 4.08(m, 2H), 3.74(m, 5H), 3.26(m, 1H), 2.76~2.63(m, 2H), 2.49~2.40(m, 2H), 1.89 (m, 2H), 1.20(t, 3H)

Preparation 30: (S)-3-amino-4-(methoxy-benzylsulfanyl)-butyric acid isopropyl ester Step A: (S)-2-BOC-amino-succinic acid 4-isopropylester 1-methylester Commercially available (S)-2-BOC-amino-succinic acid 1-methyl ester (2.4 g, 10 mmol) was dissolved in DCM (30 mL), and triethylamine (2.8 mL, 20 mmol) was added thereto. To the mixture were added isopropanol (660 mg, 11 mmol), EDC (2.5 g, 26 mmol) and HOBt (2.3 g, 30 mmol), and the mixture was stirred for 4 h at room temperature. The reaction was quenched by saturated aqueous $NaHCO_3$ solution. The reaction mixture was extracted with EtOAc, washed with saturated aqueous sodium chloride solution, and dried over anhydrous magnesium sulfate. The solvent was removed under reduced pressure, and the residue was purified by column chromatography to give the title compound (2.5 g, Yield 87%).

Step B: (S)-3-amino-4-(methoxy-benzylsulfanyl)-butyric acid isopropyl ester (S)-2-BOC-amino-succinic acid 4-isopropylester 1-methylester prepared in Step A was reacted according to the same procedure as Preparation 29 to give the title compound.

Mass [M+H]=397

Preparation 31: 2,2-Dimethyl-propionic acid (R)-2-amino-3-(4-methoxy-benzylsulfanyl)-propyl ester Step A: (R)-2-amino-3-(4-methoxy-benzylsulfanyl)-propionic acid methyl ester (R)-2-BOC-amino-3-(4-methoxy-benzylsulfanyl)-propionic acid prepared in Step B of Preparation 27 and methanol were reacted according to the same procedure as Preparation 30 to give the title compound $^1$H NMR (400 MHz, DMSO-$d_6$, HCl salt); δ 8.81(br s, 3H), 7.29(d, J=8.4 Hz, 2H), 6.91(d, J=8.4 Hz, 2H), 4.28(m, 1H), 3.18(br s, 8H), 2.95(m, 2H)

Step B: (R)-2-BOC-amino-3-(4-methoxy-benzylsulfanyl)-propionic acid methyl ester (R)-2-amino-3-(4-methoxy-benzylsulfanyl)-propionic acid methyl ester (30.7 g, 127.3 mmol) prepared in Step A was dissolved in DCM. $Et_3N$ (26.4 g, 190 mmol) and $(BOC)_2O$ (27.7 g, 127.3 mmol) were added thereto, and the mixture was stirred for 2 h at room temperature. After completion of the reaction, the reaction mixture was distilled under reduced pressure to remove DCM, and was used in the next reaction without further purification.

Step C: [(R)-2-hydroxy-1-(4-methoxy-benzylsulfanylmethyl)-ethyl]-carbamic acid t-butyl ester (R)-2-BOC-amino-3-(4-methoxy-benzylsulfanyl)-propionic acid methyl ester prepared in Step B was reacted according to the same procedure as Step A of Preparation 29 to give the title compound.

$^1$H NMR (500 MHz, DMSO-$d_6$); δ 7.24(d, J=8.6 Hz, 2H), 6.84(d, J=8.6 Hz, 2H), 4.96(br s, 1H), 3.78(s, 3H), 3.76(br s, 1H), 3.70(s, 2H), 3.7~3.66(m, 3H), 2.58(m, 2H), 1.44(s, 9H)

Step D: 2,2-Dimethylpropionic acid (R)-2-t-butoxycarbonylamino-3-(4-methoxy-benzylsulfanyl)-propyl ester

[(R)-2-hydroxy-1-(4-methoxy-benzylsulfanylmethyl)-ethyl]-carbamic acid t-butyl ester (71.3 g, 227.9 mmol) prepared in Step C was dissolved in dichloromethane (300 mL). Triethylamine (58 mL, 414.4 mmol) and trimethylacetic acid chloride (28 mL, 227.9 mmol) were added thereto, and the mixture was stirred for 6 h at 0° C. Water was added to quench the reaction. The reaction mixture was extracted with ethyl acetate, washed with saturated aqueous sodium chloride solution, and dried over anhydrous magnesium sulfate. The solvent was removed under reduced pressure, and the residue was purified by column chromatography to give the title compound (81.0 g, Yield 95%).

$^1$H NMR (400 MHz, $CDCl_3$); δ 7.25(d, J=8.8 Hz, 2H), 6.85(d, J=8.8 Hz, 2H), 4.71(m, 1H), 4.11(m, 2H), 3.79(s, 3H), 3.70(s, 2H), 2.55(d, J=6.4 Hz, 2H), 1.52(s, (H, 1.27(s, 9H)

Step E: 2,2-Dimethyl-propionic acid (R)-2-amino-3-(4-methoxy-benzylsulfanyl)-propyl ester 2,2-Dimethyl-propionic acid (R)-2-t-butoxycarbonylamino-3-(4-methoxy-benzylsulfanyl)-propyl ester (81 g, 196 mmol) prepared in Step D was dissolved in dichloromethane (300 mL). 4N hydrochloric acid/1,4-dioxane solution (100 mL) was added thereto, and the mixture was stirred for 8 h at room temperature. After completion of the reaction, the solvent was thoroughly removed under reduced pressure. The residue was recrystallized from diethylether, and dried to give the title compound (68 g, Yield 95%).

$^1$H NMR (400 MHz, DMSO-$d_6$, free form); δ 7.24(d, J=12.0 Hz, 2H), 6.85(dd, J=4.0, 8.0 Hz, 2H), 4.04(m, 1H), 3.95(m, 1H), 3.80(s, 3H), 3.68(s, 2H), 3.10(m, 1H), 2.60(m, 1H), 2.36(m, 1H), 1.18(s, 9H)

Preparation 32: 2,2-Dimethyl-propionic acid (S)-2-amino-3-(4-methoxy-benzylsulfanyl)-propyl ester Step A: (S)-2-BOC-amino-3-methylsulfonyloxy-propionic acid methyl ester Commercially available (S)-2-BOC-amino-3-hydroxy-propionic acid methyl ester and methanesulfonylchloride were reacted according to the same procedure as Step B of Preparation 29 to give the title compound.

Step B: (S)-2-BOC-amino-3-(4-methoxy-benzylsulfanyl)propionic acid methyl ester (S)-2-BOC-amino-3-methylsulfonyloxy-propionic acid methyl ester prepared in Step A and 4-methoxy-benzyl-thiol were reacted according to the same procedure as Step C of Preparation 29 to give the title compound.

Step C: (S)-2-t-butoxycarbonylamino-3-(4-methoxy-benzylsulfanyl)-propanol (S)-2-BOC-amino-3-(4-methoxy-benzylsulfanyl)propionic acid methyl ester prepared in Step B and $LiBH_4$ were reacted according to the same procedure as Step A of Preparation 29 to give the title compound.

Step D: 2,2-Dimethyl-propionic acid (R)-2-amino-3-(4-methoxy-benzylsulfanyl)-propyl ester (S)-2-t-butoxycarbonylamino-3-(4-methoxy-benzylsulfanyl)-propanol prepared in Step C, trimethylacetylchloride and HCl (4 N dioxane solution) were reacted according to the same procedures as Steps D and E of Preparation 31 consecutively to give the title compound.

Mass [M+H]=397

Preparation 33: 2-Amino-3-(4-methoxy-benzylsulfanyl)-propionic acid methyl ester Commercially available BOC-Ser-OMe was reacted according to the same procedures as Steps B, C and D of Preparation 29 sequentially to give the title compound.

Mass [M+H]=255 (M+1)

Preparation 34: 2-[(4-Methoxy-benzylsulfanyl)ethylamine

Commercially available BOC-amino-ethanol was reacted according to the same procedures as Steps B and C of Preparation 29 and Step E of Preparation 31 sequentially to give the title compound.

Mass [M+H]=197 (M+1)

Preparation 35: (R)-1-[(4-methoxy-benzylsulfanyl)methyl]propylamine

Commercially available (R)-2-BOC-amino-1-butanol was reacted according to the same procedures as Steps B and C of Preparation 29 and Step E of Preparation 31 sequentially to give the title compound.

Mass [M+H]=225 (M+1)

Preparation 36: (R)-1-[(4-methoxy-benzylsulfanyl)methyl]-2-methyl-1-propylamine

Commercially available 2-BOC-amino-3-methyl-butyric acid methyl ester was reacted according to the same procedures as Steps A, B and C of Preparation 29 and Step E of Preparation 31 sequentially to give the title compound.

Mass [M+H]=239 (M+1)

Preparation 37: 5-Bromomethyl-7-nitro-indole-2-carboxylic acid methyl ester

Step A: 1-BOC-5-methyl-7-nitro-indole-2-carboxylic acid methyl ester

5-Methyl-7-nitro-1H-indole-2-carboxylic acid methyl ester (24.0 g, 100 mmol) prepared in Preparation 15 was dissolved in dichloromethane (500 mL), to which were added triethylamine (84 mL, 601 mmol) and 4-(dimethylamino)pyridine (600 mg, 5 mmol). $(BOC)_2O$ (43.7 g, 200 mmol) dissolved in dichloromethane (100 mL) was added in drops thereto, and the mixture was stirred for 8 h at room temperature. After completion of the reaction, water was added. The reaction mixture was extracted with ethyl acetate, washed with saturated aqueous sodium chloride solution, dried over anhydrous magnesium sulfate, and concentrated under reduced pressure to give the title compound (34.0 g, Yield 100%).

$^1$H-NMR (5001-IMz, $CDCl_3$); δ 7.80(s, 1H), 7.67(s, 1H), 7.15(s, 1H), 3.93(s, 3H), 2.51(s, 3H), 1.62(s, 9H)

Step B: 1-BOC-5-bromomethyl-7-nitro-indole-2-carboxylic acid methyl ester

1-BOC-5-methyl-7-nitro-indole-2-carboxylic acid methyl ester (34 g, 101.7 mmol) prepared in Step A was dissolved in carbon tetrachloride (100 mL). N-bromosuccinimide (27.2 g, 152.6 mmol) and AIBN (1.7 g, 10.2 mmol) were added thereto, and the mixture was stirred for 5 h at 80° C. After completion of the reaction, the reaction mixture was distilled under reduced pressure, and purified by column chromatography to give the title compound (48.0 g, Yield 100%).

$^1$H-NMR (500 HMz, $CDCl_3$); δ 8.01(s, 1H), 7.90(s, 1H), 7.21(s, 1H), 4.60(s, 2H), 3.93(s, 3H), 1.62(s, 9H)

Step C: 5-Bromomethyl-7-nitro-indole-2-carboxylic acid methyl ester

1-BOC-5-bromomethyl-7-nitro-indole-2-carboxylic acid methyl ester prepared in Step B was reacted according to the same procedure as Step E of Preparation 31 to give the title compound.

Mass [M+H]=313 (M+1)

Preparation 38: 5-Hydroxymethyl-7-nitro-1H-indole-2-carboxylic acid

Step A: 1-BOC-5-acetoxymethyl-7-nitro-indole-2-carboxylic acid methyl ester

1-BOC-5-bromomethyl-7-nitro-indole-2-carboxylic acid methyl ester (10.0 g, 24.2 mmol) prepared in Step B of Preparation 37 was dissolved in N,N-dimethylformamide (50 mL). Sodium acetate (2.4 g, 29.0 mmol) was added thereto, and the mixture was stirred for 4 h at room temperature. After completion of the reaction, the solvent was removed by distillation under reduced pressure. The residue was extracted with ethyl acetate, washed with saturated aqueous sodium chloride solution, and dried over anhydrous magnesium sulfate. The residue was purified by column chromatography to give the title compound (4.7 g, Yield 50%).

$^1$H-NMR (500 HMz, $CDCl_3$); δ 7.99(s, 1H), 7.90(s, 1H), 7.21(s, 1H), 5.22(s, 2H), 3.94(s, 3H), 2.12(s, 3H), 1.63(s, 9H)

Step B: 5-Acetoxymethyl-7-nitro-1H-indole-2-carboxylic acid methyl ester

1-BOC-5-acetoxymethyl-7-nitro-indole-2-carboxylic acid methyl ester (4.7 g, 12.0 mmol) prepared in Step A was dissolved in dichloromethane (50 mL). 2N hydrochloric acid solution (30 mL, 60 mmol) was added thereto, and the mixture was stirred for 12 h at room temperature. The reaction mixture was distilled under reduced pressure to give the solid title compound (3.5 g, Yield 100%).

$^1$H-NMR (500 HMz, $CDCl_3$); δ 10.33(br s, 1H), 8.32(s, 1H), 8.06(s, 1H), 7.34(s, 1H), 5.24(s, 2H), 3.99(s, 3H), 2.12(s, 3H)

Step C: 5-Hydroxymethyl-7-nitro-1H-indole-2-carboxylic acid

5-Acetoxymethyl-7-nitro-1H-indole-2-carboxylic acid methyl ester (3.5 g, 12.0 mmol) prepared in Step B was dissolved in a solvent mixture of tetrahydrofuran, methanol and water (1:1:1, 100 mL). Lithium hydroxide hydrate (1.5 g, 35.9 mmol) was added thereto, and the mixture was stirred for 3 h at room temperature. After completion of the reaction, methanol and tetrahydrofuran were removed by distillation under reduced pressure. 1N hydrochloric acid was added to the residue. The reaction mixture was extracted with ethyl acetate, dried over anhydrous magnesium sulfate, and distilled under reduced pressure to remove the solvent. The residue was purified by column chromatography to give the title compound (2.3 g, Yield 81%).

$^1$H-NMR (500 HMz, DMSO-$d_6$); δ 11.02(br s, 1H), 8.21(s, 1H), 8.10(s, 1H), 7.34(s, 1H), 5.43(br s, 1H), 4.64(s, 2H)

Preparation 39: 5-(1,3-Dioxo-1,3-dihydro-isoindol-2-ylmethyl)-7-nitro-1H-indole-2-carboxylic acid methyl ester Step A: 1-BOC-5-(1,3-dioxo-1,3-dihydro-isoindol-2-ylmethyl)-7-nitro-1H-indole-2-carboxylic acid methyl ester 1-BOC-5-bromomethyl-7-nitro-indole-2-carboxylic acid methyl ester (4.9 g, 11.4 mmol) prepared in Step B of Preparation 37 was dissolved in N,N-dimethylformamide (50 mL). Potassium phthalimide (2.7 g, 14.8 mmol) was added thereto, and the mixture was stirred for 4 h at room temperature. Water was added to quench the reaction. The reaction mixture was extracted with ethyl acetate, washed with saturated aqueous sodium chloride solution, and dried over anhydrous magnesium sulfate. The solvent was removed by distillation under reduced pressure, and the residue was purified by column chromatography to give the title compound (3.6 g, Yield 66%).

$^1$H-NMR (500 HMz, $CDCl_3$); δ 8.04(s, 1H), 7.98(s, 1H), 7.85(m, 2H), 7.71(m, 2H), 7.17(s, 1H), 4.96(s, 2H), 4.37(q, 2H), 1.59(s, 9H), 1.39(t, 3H)

Step B: 5-(1,3-Dioxo-1,3-dihydro-isoindol-2-ylmethyl)-7-nitro-1H-indole-2-carboxylic acid methyl ester 1-BOC-5-(1,3-dioxo-1,3-dihydro-isoindol-2-ylmethyl)-7-nitro-1H-indole-2-carboxylic acid methyl ester prepared in Step A was reacted according to the same procedure as Step B of Preparation 38 to give the title compound.

Mass [M+H]=379 (M+1)

Preparation 40: 2,2-Dimethyl-propionic acid (R)-2-(7-nitro-1H-indol-2-yl)-4,5-dihydro-thiazol-4-ylmethyl ester Step A: 7-Nitro-1H-indole-2-carboxylic acid 7-Nitro-1H-indole-2-carboxylic acid methyl ester (13 g, 59 mmol) prepared in Preparation 17 was dissolved in a solvent mixture of tetrahydrofuran and water (1:1, 300 mL), to which was added 1N aqueous sodium hydroxide solution (180 mL, 177 mmol). The mixture was stirred for 3 h at room temperature, and excess 6N hydrochloric acid solution was added thereto. The reaction mixture was extracted with ethyl acetate. The extract was washed with saturated aqueous sodium chloride solution, dried over anhydrous magnesium sulfate, and filtered. The solvent was removed by distillation under reduced pressure, and the residue was dried to give the title compound (12 g, Yield 99%).

Step B: 2,2-Dimethyl-propionic acid (R)-3-(4-methoxy-benzylsulfanyl)-2-[(7-nitro-1H-indole-2-carbonyl)-amino]-propyl ester 7-Nitro-1H-indole-2-carboxylic acid (8.2 g, 22.7 mmol) prepared in Step A and 2,2-dimethyl-propionic acid (R)-2-amino-3-(4-methoxy-benzylsulfanyl)-propyl ester (13.2 g, 27.2 mmol) prepared in Preparation 31 were dissolved in N,N-dimethylformamide (100 mL). EDC (6.6 g, 25.0 mmol) and HOBT (4.6 g, 25.0 mmol) were added thereto, and the mixture was stirred for 8 h at room temperature. Saturated aqueous sodium bicarbonate solution was added to the mixture to quench the reaction. The reaction mixture was extracted with ethyl acetate, dried over anhydrous magnesium sulfate, filtered, and distilled under reduced pressure. The residue was purified by column chromatography to give the title compound (8.1 g, Yield 71%).

$^1$H-NMR (400 HMz, $CDCl_3$); δ 10.47(br s, 1H), 8.27(d, J=8.0 Hz, 1H), 8.01(d, J=8.0 Hz, 1H), 7.26(m, 2H), 6.93(d, J=4.0 Hz, 1H), 6.83(m, 2H), 6.74(d, J=8.0 Hz, 1H), 4.56(m, 1H), 4.44(m, 1H), 4.24(m, 1H), 3.74(m, 5H), 2.77(m, 1H), 2.62(m, 1H), 1.18(s, 9H)

Step C: 2,2-Dimethyl-propionic acid [(R)-2-(7-nitro-1H-indol-2-yl)-4,5-dihydro-thiazol-4-yl]-methyl ester 2,2-Dimethyl-propionic acid (R)-3-(4-methoxy-benzylsulfanyl)-2-[(7-nitro-1H-indole-2-carbonyl)-amino]-propyl ester (1.6 g, 3.2 mmol) prepared in Step B was dissolved in dichloromethane (50 mL). Phosphorus pentachloride (1.3 g, 6.4 mmol) was added thereto, and the mixture was stirred for 5 h at room temperature. Saturated aqueous sodium bicarbonate solution was added to the mixture to quench the reaction. The reaction mixture was extracted with ethyl acetate, dried over anhydrous magnesium sulfate, filtered, and distilled under reduced pressure. The residue was purified by column chromatography to give the title compound (0.8 g, Yield 69%).

$^1$H-NMR (400 HMz, $CDCl_3$); δ 10.53(br s, 1H), 8.26(d, J=8.0 Hz, 1H), 7.99(d, J=8.0 Hz, 1H), 7.04(d, J=2.0 Hz, 1H), 6.90(d, J=7.6 Hz, 1H), 4.78(m, 1H), 4.46(m, 1H), 4.30(m, 1H), 3.59(m, 1H), 3.36(m, 1H), 1.20(s, 9H)

Preparation 41: 2,2-Dimethyl-propionic acid (R)-2-[(5-chloromethyl-7-nitro-1H-indol-2-yl)-(4,5-dihydro-thiazol-4-yl)methyl ester Step A: 2,2-Dimethyl-propionic acid (R)-2-[(5-hydroxymethyl-7-nitro-1H-indole-2-carbonyl)-amino]-3-(4-methoxy-benzylsulfanyl)-propyl ester 5-Hydroxymethyl-7-nitro-1H-indole-2-carboxylic acid prepared in Preparation 38 and 2,2-dimethyl-propionic acid (R)-2-amino-3-(4-methoxy-benzylsulfanyl)-propyl ester prepared in Preparation 31 were reacted according to the same procedure as Step B of Preparation 40 to give the title compound.

Step B: 2,2-Dimethyl-propionic acid (R)-2-(5-chloromethyl-7-nitro-1H-indol-2-yl)-(4,5-dihydro-thiazol-4-yl)methyl ester 2,2-Dimethyl-propionic acid (R)-2-[(5-hydroxymethyl-7-nitro-1H-indole-2-carbonyl)-amino]-3-(4-methoxy-benzylsulfanyl)-propyl ester prepared in Step A was reacted according to the same procedure as Step C of Preparation 40 to give the title compound.

Mass [M+H]=395 (M+1)

Preparation 42: (R)-2-[(5-chloromethyl-7-nitro-1H-indol-2-yl)-4,5-dihydro-thiazol-4-yl]acetic acid methylester 5-Hydroxymethyl-7-nitro-1H-indole-2-carboxylic acid prepared in Preparation and (R)-3-amino-4-(4-methoxy-benzylsulfanyl)-butyric acid methyl ester hydrochloride prepared in Preparation 27 were reacted according to the same procedures as Steps B and C of Preparation 40 to give the title compound.

Mass [M+H]=353 (M+1)

Preparation 43: 2,2-Dimethyl-propionic acid (R)-2-[5-(2,2-dimethyl-propionyloxymethyl)-7-nitro-1H-indol-2-yl]-4,5-dihydro-thiazol-4-yl-methyl ester

Step A: 2,2-Dimethyl-propionic acid (R)-2-{5-(2,2-dimethyl-propionyloxymethyl)-7-nitro-1H-indole-2-carbonyl}-amino-3-(4-methoxy-benzylsulfanyl)-propyl ester 2,2-Dimethyl-propionic acid (R)-2-[(5-hydroxymethyl-7-nitro-1H-indole-2-carbonyl)-amino]-3-(4-methoxy-benzylsulfanyl)-propyl ester (3.1 g, 6.01 mmol) prepared in Step A of Preparation 41 was dissolved in DCM, to which was added $Et_3N$ (1.68 mL, 12.02 mmol). Pivaloyl chloride (0.92 mL, 6.61 mmol) was added thereto, and the mixture was stirred for 12 h at room temperature. After completion of the reaction, the solvent was removed under reduced pressure, and the residue was purified by column chromatography (eluent: EtOAc/n-Hex=1/1) to give the title compound.

Step B: 2,2-Dimethyl-propionic acid (R)-2-{[5-(2,2-dimethyl-propionyloxymethyl)-7-nitro-1H-indol-2-yl]-4,5-dihydro-thiazol-4-yl-methyl ester 2,2-Dimethyl-propionic acid (R)-2-{[5-(2,2-dimethyl-propionyloxymethyl)-7-nitro-1H-indole-2-carbonyl]-amino}-3-(4-methoxy-benzylsulfanyl)-propylester prepared in Step A was reacted according to the same procedure as Step C of Preparation 40 to give the title compound.

Mass [M+H]=475 (M+1)

Preparation 44: 2,2-Dimethyl-propionic acid (R)-2-{[5-methanesulfonylmethyl-7-nitro-1H-indol-2-yl]-4,5-dihydro-thiazol-4-yl-methyl ester

Step A: (5-Methanesulfonylmethyl-7-nitro-1H-indol-2-yl)-carboxylic acid methyl ester 5-Bromomethyl-7-nitro-indole-2-carboxylic acid methyl ester (251 mg, 0.805 mmol) prepared in Preparation 37 was added to DMF (8 mL). $NaSO_2Me$ (290 mg, 2.415 mmol) was added thereto, and the mixture was stirred for 2 h at room temperature. The reaction was quenched by saturated aqueous $NaHCO_3$ solution. The reaction mixture was extracted with EtOAc, and dried over anhydrous magnesium sulfate. The solvent was removed under reduced pressure, and the residue was used in the next reaction without further purification.

Step B: 2,2-Dimethyl-propionic acid (R)-2-{[5-methanesulfonylmethyl-7-nitro-1H-indol-2-yl]-4,5-dihydro-thiazol-4-yl-methyl ester (5-Methanesulfonylmethyl-7-nitro-1H-indol-2-yl)-carboxylic acid methylester prepared in Step A and 2,2-dimethyl-propionic acid (R)-2-amino-3-(4-methoxy-benzylsulfanyl)-propyl ester prepared in Preparation 31 were reacted according to the same procedure as Preparation 40 to give the title compound.

Mass [M+H]=453 (M+1)

Preparation 45: (R)-2-[5-methanesulfonylmethyl-7-nitro-1H-indol-2-yl]-4,5-dihydro-thiazol-4-yl-acetic acid methyl ester (5-Methanesulfonylmethyl-7-nitro-1H-indol-2-yl)-carboxylic acid methylester prepared in Step A of Preparation 44 and (R)-3-amino-4-(4-methoxy-benzylsulfanyl)-butyric acid methyl ester hydrochloride prepared in Preparation 27 were reacted according to the same procedure as Preparation 40 to give the title compound.

Mass [M+H]=411 (M+1)

Preparations 46 to 91

The compounds of Preparations 14 to 26, 38 and 39 and the compounds of Preparations 27 to 36 were selectively used to synthesize the Preparation Compounds in the following table according to a method selected from Preparations 40 to 45.

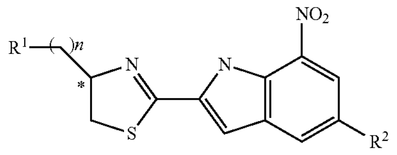

| Preparation | $R^1$ | * | n | $R^2$ | Mass [M + H] |
|---|---|---|---|---|---|
| 46 | $MeO_2C$— | R | 1 | (pyridin-3-yl)oxy | 412 |
| 47 | (t-Bu)C(O)O | R | 1 | (pyridin-3-yl)oxy | 454 |
| 48 | $MeO_2C$— | R | 1 | 4-(methanesulfonyl)phenoxy | 489 |
| 49 | $MeO_2C$ — | R | 1 | methoxy | 347 |
| 50 | $MeO_2C$— | R | 2 | methoxy | 361 |
| 51 | $MeO_2C$— | R | 1 | methoxy | 347 |
| 52 | $(i-Pr)O_2C$— | S | 1 | methyl | 361 |
| 53 | (t-Bu)C(O)O | R | 1 | methyl | 375 |
| 54 | $EtO_2C$— | R | 1 | methyl | 347 |
| 55 | $EtO_2C$— | S | 2 | methyl | 361 |
| 56 | $EtO_2C$— | R | 2 | methyl | 361 |
| 57 | $EtO_2C$— | R | 2 | bromo | 412 |
| 58 | $MeO_2C$— | R | 1 | bromo | 386 |
| 59 | (t-Bu)C(O)O | R | 1 | bromo | 440 |
| 60 | (t-Bu)C(O)O | R | 1 | acetylamino | 418 |
| 61 | $MeO_2C$— | S | 1 | ethoxy | 363 |
| 62 | $EtO_2C$— | R | 2 | ethoxy | 391 |
| 63 | $MeO_2C$— | R | 1 | ethoxy | 363 |
| 64 | $EtO_2C$— | R | 1 | chloro | 367 |
| 65 | (t-Bu)C(O)O | R | 1 | chloro | 395 |
| 66 | $(i-Pr)O_2C$— | S | 1 | chloro | 381 |
| 67 | $MeO_2C$— | R | 1 | chloro | 353 |
| 68 | $MeO_2C$— | R | 2 | chloro | 367 |
| 69 | isobutyl | R | 0 | chloro | 323 |
| 70 | $MeO_2C$— | R | 1 | phenoxy | 411 |
| 71 | $(i-Pr)O_2C$— | S | 1 | phenoxy | 439 |
| 72 | $MeO_2C$— | R | 2 | phenoxy | 425 |
| 73 | $MeO_2C$— | R | 1 | phenylaminomethyl | 424 |
| 74 | ethyl | R | 0 | fluoro | 293 |
| 75 | $EtO_2C$— | R | 1 | fluoro | 351 |
| 76 | $EtO_2C$— | R | 2 | fluoro | 365 |
| 77 | (t-Bu)C(O)O | R | 1 | fluoro | 379 |
| 78 | (t-Bu)C(O)O | R | 1 | $CH_2$-(isoindol-1,3-dion-1-yl) | 520 |
| 79 | $MeO_2C$— | R | 1 | $CH_2$-(isoindol-1,3-dion-1-yl) | 478 |
| 80 | $(t-Bu)C(O)OCH_2$ | R | 1 | H | 361 |
| 81 | $MeO_2C$— | R | 1 | H | 319 |
| 82 | $(i-Pr)O_2C$— | S | 1 | H | 347 |
| 83 | $EtO_2C$— | R | 2 | H | 347 |
| 84 | $(t-Bu)C(O)OCH_2$ | S | 1 | H | 361 |
| 85 | methyl | R | 0 | H | 261 |
| 86 | ethyl | R | 0 | H | 275 |
| 87 | $MeO_2C$— | R | 0 | H | 305 |
| 88 | (t-Bu)C(O)O | R | 2 | H | 375 |
| 89 | $MeO_2C$— | R | 1 | O(n-Pr) | 363 |
| 90 | $EtO_2C$— | R | 2 | $OCF_3$ | 417 |
| 91 | t-BuC(O)O | R | 2 | $OCH_3$ | 391 |

Preparation 92: 2,2-Dimethyl-propionic acid [(R)-2-(5-dimethylaminomethyl-7-nitro-1H-indol-2-yl)-4,5-dihydro-thiazol-4-yl]methyl ester 2,2-Dimethyl-propionic acid [(R)-2-(5-chloromethyl-7-nitro-1H-indol-2-yl)-4,5-dihydro-thiazol-4-yl]methyl ester (1.0 g, 2.4 mmol) prepared in Preparation 41 was dissolved in dimethylsulfoxide (15 mL). Diisopropylethylamine (0.6 g, 4.9 mmol) and dimethylamine (0.2 g, 4.9 mmol) were added thereto, and the mixture was stirred for 6 h at room temperature. After completion of the reaction, water was added. The reaction mixture was extracted with ethyl acetate, dried over anhydrous magnesium sulfate, and filtered. The filtrate was distilled under reduced pressure, and purified by column chromatography to give the title compound (0.7 g, Yield 71%).

Mass [M+H]=418 (M+1)

Preparation 93: 2,2-Dimethyl-propionic acid {(R)-2-[5-(morpholin-4-yl)methyl-7-nitro-1H-indol-2-yl]-4,5-dihydro-thiazol-4-yl}methyl ester 2,2-Dimethyl-propionic acid [(R)-2-(5-chloromethyl-7-nitro-1H-indol-2-yl)-4,5-dihydro-thiazol-4-yl]methyl ester prepared in Preparation 41 and morpholine were reacted according to the same procedure as Preparation 92 except that DMF was used as the solvent instead of DMSO to give the title compound.

Mass [M+H]=460 (M+1)

Preparation 94: 2,2-Dimethyl-propionic acid {(R)-2 [5-(pyrazol-1-yl)methyl-7-nitro-1H-indol-2-yl]-4,5-dihydro-thiazol-4-yl} methyl ester 2,2-Dimethyl-propionic acid [(R)-2-(5-chloromethyl-7-nitro-1H-indol-2-yl)-4,5-dihydro-thiazol-4-yl]methyl ester prepared in Preparation 41 and pyrazole were reacted according to the same procedure as Preparation 92 except that DMF was used as the solvent instead of DMSO to give the title compound.

Mass [M+H]=441 (M+1)

Preparation 95: 2,2-Dimethyl-propionic acid {(R)-2-[5-(1,3-imidazol-1-yl)methyl-7-nitro-1H-indol-2-yl]-4,5-dihydro-thiazol-4-yl} methyl ester 2,2-Dimethyl-propionic acid [(R)-2-(5-chloromethyl-7-nitro-1H-indol-2-yl)-4,5-dihydro-thiazol-4-yl]methyl ester prepared in Preparation 41 and 1,3-imidazole were reacted according to the same procedure as Preparation 92 except that DMF was used as the solvent instead of DMSO to give the title compound.

Mass [M+H]=441 (M+1)

Preparation 96: 2,2-Dimethyl-propionic acid {(R)-2-[5-(1,2,4-triazol-1-yl)methyl-7-nitro-1H-indol-2-yl]-4,5-dihydro-thiazol-4-yl} methyl ester 2,2-Dimethyl-propionic acid [(R)-2-(5-chloromethyl-7-nitro-1H-indol-2-yl)-4,5-dihydro-thiazol-4-yl]methyl ester prepared in Preparation 41 and 1,2,4-triazole were reacted according to the same procedure as Preparation 92 except that DMF was used as the solvent instead of DMSO to give the title compound.

Mass [M+H]=442 (M+1)

Preparation 97: 2,2-Dimethyl-propionic acid {(R)-2-[5-(pyrrol-1-yl)methyl-7-nitro-1H-indol-2-yl]-4,5-dihydro-thiazol-4-yl} methyl ester 2,2-Dimethyl-propionic acid [(R)-2-(5-chloromethyl-7-nitro-1H-indol-2-yl)-4,5-dihydro-thiazol-4-yl]methyl ester prepared in Preparation 41 and pyrrole were reacted according to the same procedure as Preparation 92 except that DMF was used as the solvent instead of DMSO to give the title compound.

Mass [M+H]=440 (M+1)

Preparation 98: [(R)-2-(7-nitro-5-phenoxymethyl-1H-indol-2-yl)-4,5-dihydro-thiazol-4-yl]-acetic acid methyl ester Phenol (192 mg, 2.04 mmol) was dissolved in DMF. NaH (60% mineral oil, 82 mg, 2.04 mmol) was added, and the reaction solution was cooled to 0° C. (R)-2-(5-chloromethyl-7-nitro-1H-indol-2-yl)-4,5-dihydro-thiazol-4-yl-acetic acid methyl ester (500 mg, 1.36 mmol) prepared in Preparation 42, which was dissolved in DMF, was slowly added thereto. The reaction solution was warmed to room temperature, and stirred for 4 h. After saturated aqueous $NH_4Cl$ solution was added to quench the reaction, the reaction mixture was extracted with EtOAc, dried over $MgSO_4$, and filtered. The solvent was removed under reduced pressure, and the residue was purified by column chromatography (eluent: EtOAc/n-Hex=1/2) to give the title compound.

Mass [M+H]=425 (M+1)

Preparation 99: 2,2-Dimethyl-propionic acid {(R)-2-[7-nitro-5-(phenylamino)methyl-1H-indol-2-yl]-4,5-dihydro-thiazol-4-yl}methyl ester (R)-2-(5-chloromethyl-7-nitro-1H-indol-2-yl)-4,5-dihydro-thiazol-4-yl-acetic acid methyl ester prepared in Preparation 42 and phenylamine were reacted according to the same procedure as Preparation 98 to give the title compound.

Mass [M+H]=466 (M+1)

Preparation 100: 2,2-Dimethyl-propionic acid {(R)-2-[7-nitro-5-(pyrrolidin-1-yl)methyl-1,4-indol-2-yl]-4,5-dihydro-thiazol-4-yl}methyl ester 2,2-Dimethyl-propionic acid (R)-2-[(5-chloromethyl-7-nitro-1H-indol-2-yl)-(4,5-dihydro-thiazol-4-yl)methyl ester prepared in Preparation 41 and pyrrolidine were reacted according to the same procedure as Preparation 92 except that DMF was used as the solvent instead of DMSO to give the title compound.

Mass [M+H]=444 (M+1)

Preparation 101: 2-(4,5-Dihydro-thiazol-2-yl)-7-nitro-1H-indole

Step A: 7-Nitro-1H-indole-2-carboxylic acid

Commercially available ethyl 7-nitroindole-2-carboxylate (500 mg, 2.14 mmol) was dissolved in a solvent mixture of tetrahydrofuran and water (1:1, 20 mL). Lithium hydroxide hydrate (448 mg, 10.7 mmol) was added thereto, and the mixture was stirred for 8 h at room temperature. 1N-hydrochloric acid solution was added, and the reaction mixture was extracted with ethyl acetate. The extract was dried over anhydrous magnesium sulfate, and filtered. The filtrate was distilled under reduced pressure to give the title compound.

Step B: 7-Nitro-1H-indole-2-carboxylic acid (2-chloro-ethyl)-amide

7-Nitro-1H-indole-2-carboxylic acid (371 mg, 3.2 mmol) prepared in Step A was dissolved in N,N-dimethylformamide (10 mL). Triethylamine (0.6 mL, 4.3 mmol), EDC (614 mg, 3.2 mmol) and HOBT (433 mg, 3.2 mmol) were added, 2-chloroethylamine (252.8 mg, 3.2 mmol) was added, and the mixture was stirred for 8 h at room temperature. 1N-hydrochloric acid solution was added, and the reaction mixture was extracted with ethyl acetate, washed with saturated sodium bicarbonate solution, dried over anhydrous magnesium sulfate, and filtered. The filtrate was distilled under reduced pressure to give the title compound.

$^1$H NMR (400 MHz, $CDCl_3$); δ 10.51(br s, 1H), 8.28(d, J=6.4 Hz, 1H), 8.02(d, J=6.4 Hz, 1H), 7.27(t, 1H), 7.03(s, 1H), 6.62(br s, 1H), 3.86(m, 2H), 3.77(m, 2H)

Step C: 2-(4,5-Dihydro-thiazol-2-yl)-7-nitro-1H-indole

7-Nitro-1H-indole-2-carboxylic acid (2-chloro-ethyl)-amide (267 mg, 1 mmol) prepared in Step B was dissolved in dichloroethane (10 mL) and toluene (10 mL), and Lawesson's Reagent (1.29 g, 3.2 mmol) was added thereto. The mixture was refluxed for 4 h, and distilled under reduced pressure. Water was added thereto, and the reaction mixture was extracted with ethyl acetate, dried over anhydrous magnesium sulfate, and filtered. The filtrate was distilled under reduced pressure, and the concentrate was purified by column chromatography to give the title compound as a product of the cyclization reaction (148 mg, Yield 60%).

$^1$H-NMR (400 HMz, $CDCl_3$); δ 10.49(br s, 1H), 8.24(d, J=8.0 Hzm 1H), 7.98(d, J=7.6 Hz, 1H), 7.23(t, 1H), 7.02(s, 1H), 4.47(t, 2H), 3.51(t, 2H)

Preparation 102: [(S)-2-(5-chloro-7-nitro-1H-indol-2-yl)-4,5-dihydrooxazol-4-yl]-carboxylic acid isopropyl ester Step A: (S)-3-amino-4-hydroxy-butyric acid isopropyl ester (S)-2-BOC-amino-succinic acid 4-isopropyl ester 1-methylester prepared in Step A of Preparation 30 was reacted according to the same procedures as Steps A to D of Preparation 29 sequentially to give the title compound.

Step B: [(S)-3-(5-chloro-7-nitro-1H-indole-2-carbonyl)-amino]-4-hydroxy-butyric acid isopropyl ester 5-Chloro-7-nitro-1H-indole-2-carboxylic acid obtained by the hydrolysis of 5-chloro-7-nitro-1H-indole-2-carboxylic acid methyl ester prepared in Preparation 14 according to Step A of Preparation 40 and (S)-3-amino-4-hydroxy-butyric acid isopropyl ester prepared in Step A were reacted according to the same procedure as Step B of Preparation 40 to give the title compound.

Step C: [(S)-3-(5-chloro-7-nitro-1H-indole-2-carbonyl)-amino]-4-methanesulfonyloxy-butyric acid isopropyl ester

[(S)-3-(5-chloro-7-nitro-1H-indole-2-carbonyl)-amino]-4-hydroxy-butyric acid isopropyl ester prepared in Step B was reacted according to the same procedure as Step B of Preparation 29 to give the title compound.

Step D: [(S)-2-(5-chloro-7-nitro-1H-indol-2-yl)-4,5-dihydrooxazol-4-yl]-carboxylic acid isopropyl ester

[(S)-3-(5-chloro-7-nitro-1H-indole-2-carbonyl)-amino]-4-methanesulfonyloxy-butyric acid isopropyl ester (930 mg, 2 mmol) prepared in Step C was added to THF (10 mL). $K_2CO_3$ (330 mg, 10 mmol) was added thereto, and the mixture was stirred for 2 h at 80° C. Water was added to quench the reaction. The reaction mixture was extracted with EtOAc, and dried over $MgSO_4$. The solvent was removed under reduced pressure, and the residue was purified by column chromatography (eluent: EtOAc/n-Hex/DMC=1/4/1) to give the title compound (445 mg, Yield 61%).

Mass [M+H]=365(M+1)

Preparation 103: (1S,2R)-(3-amino-1-benzyl-2-hydroxy-propyl)-carbamic acid t-butyl ester Step A: (1S,2R)-(3-azido-1-benzyl-2-hydroxy-propyl)-carbamic acid t-butyl ester Commercially available (1-oxirane-2-phenyl-ethyl)-carbamic acid t-butyl ester (2.6 g, 10 mmol) was dissolved in DMF (30 mL). Sodium azide (655 mg, 10 mmol) was added thereto, and the mixture was stirred for 12 h at 80° C. Water was added to quench the reaction. The reaction mixture was extracted with EtOAc and dried over $MgSO_4$. The solvent was removed under reduced pressure, and the residue was purified by column chromatography to give the title compound (2.75 g, Yield 90%).

Step B: (1S,2R)-(3-amino-1-benzyl-2-hydroxy-propyl)-carbamic acid t-butyl ester (1S,2R)-(3-azido-1-benzyl-2-hydroxy-propyl)-carbamic acid t-butyl ester (2.5 g, 8.17 mmol) prepared in Step A was dissolved in methanol (15 mL), to which was added Pd/C (100 mg). The mixture was reacted for 12 h in a hydrogen reactor (50 psi), and filtered through a cellite. The solvent was removed under reduced pressure, and the residue was used in the next reaction without further purification.

Mass [M+H]=280 (M+1)

Preparation 104: [(1S,2R)-1-benzyl-3-(1,3-dioxo-1,3-dihydro-isoindol-2-yl)-2-hydroxy-propyl]carbamic acid t-butyl ester (1R,2S)-(3-amino-1-benzyl-2-hydroxy-propyl)-carbamic acid t-butyl ester (1.4 g, 5 mmol) prepared in Preparation 103 was dissolved in DMF (20 mL), to which was added phthalic anhydride (735 mg, 5 mmol). $Et_3N$ (1.4 mL, 10 mmol) was added thereto, and the mixture was stirred for 24 h at 80° C. The reaction was quenched by water, and the reaction mixture was extracted with EtOAc, and dried over $MgSO_4$. The solvent was removed under reduced pressure, and the residue was dissolved in DCM. TFA was added thereto, and the mixture was stirred for 2 h at room temperature. After completion of the reaction, the solvent was removed under reduced pressure. The residue was recrystallized from DCM/Hex to give the title compound (1.18 g, Yield 71%).

Mass [M+H]=410 (M+1)

Preparations 105 to 109

Indole-2-carboxylic acid esters prepared in Preparations 14, 15 and 17 and amino ethanol derivatives that are commercially available or prepared in Preparations 103 and 104 were reacted according to the same procedure as Preparation 101 to synthesize the Preparation Compounds in the following table.

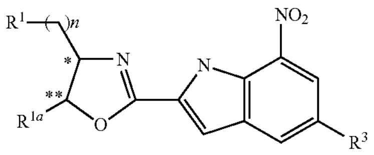

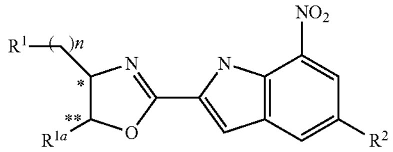

| Preparation | $R^1$ | $R^{1a}$ | * | ** | n | $R^3$ | Mass [M + H] |
|---|---|---|---|---|---|---|---|
| 105 | $MeO_2C$ | H | S | — | 1 | methyl | 317 |
| 106 | isobutyl | H | R | — | 0 | Cl | 321 |
| 107 | H | (S)—Ph—$CH_2$—$CH(NH_2)$— | — | R | 0 | Cl | 384 |
| 108 | Ph—$CH_2$— | 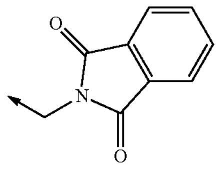 | S | R | 1 | Cl | 514 |
| 109 | H | H | — | — | 0 | H | 231 |

Preparation 110: 2-(Thiazol-2-yl)-7-nitro-1H-indole

Step A: 7-Nitro-1H-indole-2-carbothioic acid amide

7-Nitro-1H-indole-2-carboxylic acid prepared in Step A of Preparation 101 and ammonium chloride were reacted according to the same procedures as Steps B and C of Preparation 101 to give the title compound.

Step B: 2-(Thiazol-2-yl)-7-nitro-1H-indole

7-Nitro-1H-indole-2-carbothioic acid amide (1.15 g, 5 mmol) prepared in Step A was dissolved in DMF (15 mL). 2-Bromo-1,1-dioxyethane (985 mg, 5 mmol) was added thereto, and the mixture was stirred under reflux for 2 h at 100° C. The reaction was quenched by water, and the reaction mixture was extracted with EtOAc, and dried over $MgSO_4$. The solvent was removed under reduced pressure, and the residue was purified by column chromatography to give the title compound (612 mg, Yield 65%).

Mass [M+H]=245 (M+1)

Preparation 111: 2-(7-Nitro-1H-indol-2-yl)-thiazole-4-carboxylic acid methyl ester 3-Chloro-2-oxo-propionic acid methyl ester and 7-nitro-1H-indole-2-carbothioic acid amide prepared in Step A of Preparation 110 were reacted according to the same procedure as Preparation 110 to give the title compound.

Mass [M+H]=303 (M+1)

Preparation 112: [2-(7-Nitro-1H-indol-2-yl)-thiazol-4-yl]-methanol 2-(7-Nitro-1H-indol-2-yl)-thiazole-4-carboxylic acid methyl ester prepared in Preparation 111 was reacted according to the same procedures as Step A of Preparation 29 to give the title compound.

Mass [M+H]=275 (M+1)

Preparation 113: 2-(5-Methyl-7-nitro-1H-indol-2-yl)-thiazole-4-carboxylic acid ethyl ester Step A: (5-Methyl-7-nitro-1H-indol-2-yl)carbothioic acid amide (5-Methyl-7-nitro-1H-indol-2-yl)carboxylic acid was reacted according to the same procedure as Step A of Preparation 110 to give the title compound.

Step B: 2-(5-Methyl-7-nitro-1H-indol-2-yl)-thiazole-4-carboxylic acid ethyl ester (5-Methyl-7-nitro-1H-indol-2-yl)carbothioic acid amide prepared in Step A and 3-chloro-2-oxo-propionic acid ethyl ester were reacted according to the same procedure as Step B of Preparation 110 to give the title compound.

Mass [M+H]=331 (M+1)

Preparation 114: [2-(5-Methyl-7-nitro-1H-indol-2-yl)-thiazol-4-yl]-methanol 2-(5-Methyl-7-nitro-1H-indol-2-yl)-thiazole-4-carboxylic acid methyl ester prepared in Preparation 113 was reacted according to the same procedure as Step A of Preparation 29 to give the title compound.

Mass [M+H]=289 (M+1)

Preparation 115: [5-(7-Nitro-1H-indol-2-yl)-[1,2,4]oxadiazol-3-yl]-acetic acid methyl ester Step A: 2-(N-hydroxycarbamimidoyl)-acetic acid methyl ester 2-Cyano-acetic acid methyl ester (990 mg, 10 mmol) was dissolved in THF (30 mL). Hydroxy amine (690 mg, HCl salt, 10 mmol) was added thereto, and the mixture was stirred for 2 h at 80° C. After completion of the reaction, 1N HCl was added. The reaction mixture was extracted with EtOAc, and dried over $MgSO_4$. The solvent was removed under reduced pressure, and the residue was used in the next reaction without further purification.

Step B: 3-(Hydroxyimino)-3-[(7-nitro-1H-indole-2-carbonyl)-amino]-propionic acid methyl ester 2-(N-hydroxycarbamimidoyl)-acetic acid methyl ester prepared in Step A and 7-nitro-1H-indole-2-carboxylic acid prepared in Step A of Preparation 101 were reacted according to the same procedure as Step B of Preparation 101 to give the title compound.

Step C: 2-[5-(7-Nitro-1H-indol-2-yl)-[1,2,4]oxadiazol-3-yl]-acetic acid methyl ester 3-(Hydroxyimino)-3-[(7-nitro-1H-indole-2-carbonyl)-amino]-propionic acid methyl ester (960 mg, 1 mmol) prepared in Step B was dissolved in DMF (10 mL). Pyridine (1 mL) was added thereto, and the mixture was stirred for 4 h at 80° C. The reaction was quenched by aqueous $NH_4Cl$ solution. The reaction mixture was extracted with EtOAc, and dried over $MgSO_4$. The solvent was removed under reduced pressure, and the residue was purified by column chromatography to give the title compound (830 mg, Yield 90%).

Mass [M+H]=302 (M+1)

Preparation 116: 2-[5-(7-Nitro-1H-indol-2-yl)-[1,2,4]oxadiazol-3-yl]-ethanol

2-[5-(7-Nitro-1H-indol-2-yl)-[1,2,4]oxadiazol-3-yl]-acetic acid methyl ester prepared in Preparation 115 was reacted according to the same procedure as Step A of Preparation 29 to give the title compound.

Mass [M+H]=274 (M+1)

Preparation 117: 5-Methyl-7-nitro-2-[1,3,4]oxadiazol-2-yl-1H-indole

5-Methyl-7-nitro-1H-indole-2-carboxylic acid methyl ester (234 mg, 1 mmol) prepared in Preparation 15 was dissolved in methanol (10 mL), to which was added hydrazine (3 mL). The reaction solution was refluxed for 3 h, and concentrated under reduced pressure. To the concentrate was added trimethylorthoformate (10 mL), and the mixture was refluxed for 8 h. The reaction mixture was distilled under reduced pressure, and the resulting solid was washed with ethyl acetate to give the title compound (49 mg, Yield 20%).

Example 1

Cyclopentyl-[2-(4,5-dihydro-1,3-thiazol-2-yl)-1H-indol-7-yl]-amine

Step A: [2-(4,5-Dihydro-1,3-thiazol-2-yl)-1H-indol-7-yl]-amine 2-(4,5-Dihydro-thiazol-2-yl)-7-nitro-1H-indole prepared in Preparation 101 was reacted according to the same procedure as Step B of Preparation 1 to give the title compound.

Step B: Cyclopentyl-[2-(4,5-dihydro-1,3-thiazol-2-yl)-1H-indol-7-yl]-amine

[2-(4,5-Dihydro-1,3-thiazol-2-yl)-1H-indol-7-yl]-amine (15 mg, 0.07 mmol) prepared in Step A was dissolved in 1,2-dichloroethane (10 mL). Cyclopentanone (12 mg, 0.14 mmol) and sodium triacetoxyborohydride (29 mg, 0.14 mmol) were added thereto, and the mixture was stirred for 3 h at room temperature. The reaction was quenched by water, and the reaction mixture was extracted with ethyl acetate, dried over anhydrous magnesium sulfate, and filtered. The solvent was removed under reduced pressure, and the residue was purified by column chromatography to give the title compound (6.7 mg, Yield 34%).

$^1$H-NMR (400 HMz, $CDCl_3$); δ 10.27(s, 1H), 7.06(d, J=8.0 Hz, 1H), 7.00(t, J=7.6 Hz, 1H), 6.92(s, 1H), 6.52(d, J=7.2 Hz, 1H), 4.42(m, 2H), 4.38(m, 1H), 4.35(m, 2H), 2.00(m, 2H), 1.64(m, 4H), 1.46(m, 2H)

Example 2

[(R)-2-(7-cyclopentylamino-1H-indol-2-yl)-4,5-dihydro-1,3-thiazol-4-yl]-methanol Step A: 2,2-Dimethyl-propionic acid [(R)-2-(7-cyclopentylamino)-1H-indol-2-yl)-4,5-dihydro-thiazol-4-yl]methyl ester 2,2-Dimethyl-propionic acid (R)-2-(7-amino-1H-indol-2-yl)-4,5-dihydro-thiazol-4-yl methyl ester prepared in Preparation 40 was reacted according to the same procedure as Step B of Example 1 to give the title compound.

Step B: [(R)-2-(7-cyclopentylamino-1H-indol-2-yl)-4,5-dihydro-1,3-thiazol-4-yl]-methanol 2,2-Dimethyl-propionic acid [(R)-2-(7-cyclopentylamino)-1H-indol-2-yl)-4,5-dihydro-thiazol-4-yl]methyl ester prepared in Step A was reacted according to the same procedure as Step A of Preparation 29 to give the title compound.

$^1$H-NMR (500 HMz, $CDCl_3$); δ 11.17~11.08(m, 1H), 7.09 (m, 1H), 6.99(t, 1H), 6.96(s, 1H), 6.52(m, 1H), 4.72(m, 1H), 4.04(m, 1H), 3.75(m, 1H), 3.65(m, 1H), 3.51(m, 1H), 3.40(m, 1H), 1.90(m, 2H), 1.60~1.49(m, 4H), 1.41~1.24(m, 2H)

Example 3

[(R)-2-(5-chloro-7-cyclopentylamino-1H-indol-2-yl)-4,5-dihydro-thiazol-4-yl]-acetic acid methyl ester

[(R)-2-(5-chloro-7-nitro-1H-indol-2-yl)-4,5-dihydro-thiazol-4-yl]-acetic acid methyl ester prepared in Preparation 67 and cyclopentanone were reacted according to the same procedures as Steps A and B of Example 1 to give the title compound.

$^1$H NMR (DMSO-$d_6$, ppm); δ 11.51(s, 1H), 6.79(s, 1H), 6.79(s, 1H), 6.16(s, 1H), 6.13(d, 1H), 4.85(m, 1H), 3.80(m, 1H), 3.62(m, 1H), 3.58(s, 3H), 3.19(m, 1H), 2.71(m, 1H), 2.63(m, 1H), 1.93(m, 2H), 1.69(m, 2H), 1.56(m, 4H)

Example 4

[(R)-2-(5-chloro-7-cyclopentylamino-1H-indol-2-yl)-4,5-dihydro-thiazol-4-yl]-acetic acid

[(R)-2-(5-chloro-7-cyclopentylamino-1H-indol-2-yl)-4,5-dihydro-thiazol-4-yl]-acetic acid methyl ester prepared in Example 3 was reacted according to the same procedure as Step A of Preparation 29 to give the title compound.

$^1$H NMR (DMSO-$d_6$, ppm); δ 12.51(br s, 1H), 11.51(s, 1H), 6.79(s, 1H), 6.79(s, 1H), 6.16(s, 1H), 6.14(d, 1H), 4.87 (m, 1H), 3.80(m, 1H), 3.61(m, 1H), 3.19(m, 1H), 2.72(m, 1H), 2.64(m, 1H), 1.93(m, 2H), 1.69(m, 2H), 1.56(m, 4H)

Example 5

2-[(R)-2-(5-chloro-7-cyclopentylamino-1H-indol-2-yl)-4,5-dihydro-thiazol-4-yl]-ethanol

[(R)-2-(5-chloro-7-cyclopentylamino-1H-indol-2-yl)-4,5-dihydro-thiazol-4-yl]-acetic acid (391 mg, 1 mmol) prepared in Example 4 was dissolved in DCM (10 mL). Triethylamine (280 ul, 2 mmol) and isobutyric acid chloride (106 mg, 1 mmol) were added thereto, and the mixture was stirred for 30 min at 0° C. After completion of the reaction, the solvent was removed under reduced pressure. The residue was diluted with THF. $NaBH_4$ (74 mg, 2 mmol) was added thereto, and the mixture was stirred for 12 h. The reaction was quenched with a small amount of water. Again, excess water was added to the reaction mixture, which was then stirred for 30 min, extracted with EtOAc, dried over $MgSO_4$, and filtered. The solvent was removed under reduced pressure, and the residue was purified by column chromatography to give the title compound (272 mg, Yield 72%).

$^1$H NMR (400 MHz, DMSO-$d_6$); δ 11.47(s, 1H), 6.79(s, 1H), 6.67(s, 1H), 6.11(s, 1H), 6.09(m, 1H), 4.65(t, 1H), 4.54 (m, 1H), 3.80(m, 2H), 3.61(m, 2H), 3.52(m, 1H), 3.15(m, 1H), 2.47(m, 1H), 1.97(m, 2H), 1.68(m, 2H), 1.54(m, 4H)

Example 6

(R)-2-[7-cyclopentylamino-5-(hydroxymethyl)-1H-indol-2-yl]-4,5-dihydro-thiazol-4-yl-methanol Step A: 2,2-Dimethyl-propionic acid (R)-2-[7-cyclopentylamino-5-(2,2-dimethyl-propionyloxymethyl)-1H-indol-2-yl]-4,5-dihydro-thiazol-4-yl-methyl ester 2,2-Dimethyl-propionic acid (R)-2-[5-(2,2-dimethyl-propionyloxymethyl)-7-nitro-1H-indol-2-yl]-4,5-dihydro-thiazol-4-yl-methyl ester prepared in Preparation 43 and cyclopentanone were reacted according to the same procedure as Example 1 to give the title compound.

Step B: (R)-2-[7-cyclopentylamino-5-(hydroxymethyl)-1H-indol-2-yl]-4,5-dihydro-thiazol-4-yl-methanol 2,2-Dimethyl-propionic acid (R)-2-[7-cyclopentylamino-5-(2,2-dimethyl-propionyloxymethyl)-1H-indol-2-yl] amino}-4,5-dihydro-thiazol-4-yl-methyl ester prepared in Step A was reacted according to the same procedure as Step A of Preparation 29 to give the title compound.

$^1$H-NMR (400 MHz, $CDCl_3$); δ 9.63(brs, 1H), 7.40(s, 1H), 7.18(s, 1H), 6.90(s, 1H), 4.80(m, 1H), 4.73(s, 2H), 4.06(m, 1H), 3.84(m, 1H), 3.66(m, 2H), 3.48(m, 1H), 3.31(m, 1H), 1.79(m, 2H), 1.43(m, 4H), 1.26(m, 2H)

Example 7

[2-(4,5-Dihydro-thiazol-2-yl)-1H-indol-7-yl]-piperidin-4-yl-amine

Step A: [2-(4,5-Dihydro-thiazol-2-yl)-1H-indol-7-yl]-(1-BOC-piperidin-4-yl)-amine 2-(4,5-Dihydro-thiazol-2-yl)-7-nitro-1H-indole prepared in Preparation 101 and 1-BOC-4-piperidone were reacted according to the same procedure as Example 1 to give the title compound.

Step B: [2-(4,5-Dihydro-thiazol-2-yl)-1H-indol-7-yl]-piperidin-4-yl-amine

[2-(4,5-Dihydro-thiazol-2-yl)-1H-indol-7-yl]-(1-BOC-piperidin-4-yl)-amine prepared in Step A was reacted according to the same procedure as Step D of Preparation 29 to give the title compound.

$^1$H-NMR (400 HMz, $CDCl_3$, MeOH-$d_4$); δ 7.39(s, 1H), 7.07(d, J=8.0 Hz, 1H), 6.99(t, J=8.0 Hz, 1H), 6.93(s, 1H), 6.47(d, J=7.6 Hz, 1H), 4.41(m, 2H), 3.77(m, 1H), 3.48(m, 4H), 3.11(m, 2H), 2.29(m, 2H), 1.87(m, 2H)

Examples 8 to 117

The compounds prepared in Preparations 40, 48 to 100 were reacted to synthesize the Example Compounds in the following table according to a method selected from Examples 1 to 7.

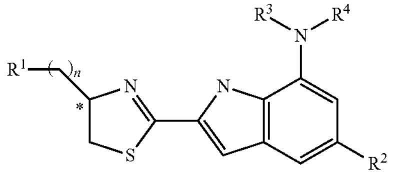

| Example | $R^1$ | * | n | $R^2$ | $R^3$ | $R^4$ |
|---|---|---|---|---|---|---|
| | | | | $H^1$ NMR data | | |
| 8 | carboxyl | R | 1 | methyl | H | (THP-4-yl)methyl |
| | (400 MHz, $CDCl_3$); δ 11.54 (brs, 1H), 7.11 (s, 1H), 6.80 (s, 1H), 6.22 (s, 1H), 5.29 (m, 1H), 3.92 (m, 2H), 3.68 (m, 1H), 3.35 (m, 2H), 3.21-3.04 (m, 3H), 2.84-2.52 (m, 2H), 2.32 (s, 3H), 1.90 (m, 1H), 1.74 (m, 2H), 1.35 (m, 2H) | | | | | |
| 9 | carboxyl | S | 1 | methyl | H | 1-(trifluoroacetyl)piperidin-4-yl |
| | (400 MHz, $CDCl_3$), δ 11.94 (brs, 1H), 6.98 (s, 1H), 6.78 (s, 1H), 6.25 (s, 1H), 5.33 | | | | | |

-continued

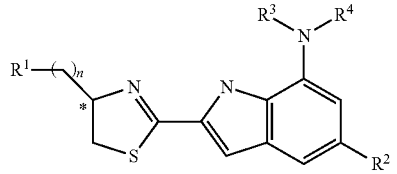

| Example | $R^1$ | * | n | $R^2$ | $R^3$ | $R^4$ |
|---|---|---|---|---|---|---|
| | $H^1$ NMR data | | | | | |
| | (m, 1H), 4.13 (m, 1H), 3.76-3.68 (m, 5H), 3.47-3.41 (m, 3H), 2.74-2.63 (m, 2H), 2.36 (s, 3H), 2.04 (m, 2H), 1.56 (m, 2H) | | | | | |
| 10 | carboxyl | S | 1 | H | H | (THP-2-yl)methyl |
| | (400 MHz, $CDCl_3$), δ 11.68 (brs, 1H), 7.06-6.98 (m, 3H), 6.45 (s, 1H), 5.32 (m, 1H), 3.96 (m, 1H), 3.77-3.61 (m, 2H), 3.43 (m, 1H), 3.28-3.21 (m, 3H), 2.80 (m, 1H), 2.65 (m, 1H), 1.83 (m, 1H), 1.71 (m, 1H), 1.62-1.42 (m, 4H) | | | | | |
| 11 | carboxyl | S | 1 | H | H | THP-4-yl |
| | (400 MHz, $CDCl_3$); δ 11.87 (brs, 1H), 7.15 (s, 1H), 7.03 (m, 2H), 6.50 (m, 1H), 5.39 (m, 1H), 4.06 (m, 2H), 3.80-3.62 (m, 2H), 3.57 (m, 2H), 3.29 (m, 1H), 2.83 (m, 1H), 2.69 (m, 1H), 2.11 (m, 2H), 1.64 (m, 2H) | | | | | |
| 12 | carboxyl | S | 1 | H | H | (THP-4-yl)methyl |
| | (400 MHz, $CDCl_3$); δ 11.89 (brs, 1H), 7.13 (s, 1H), 7.04 (m, 2H), 6.44 (m 1H), 5.39 (m, 1H), 3.98 (m, 2H), 3.77 (m, 1H), 3.41 (m, 2H), 3.25 (m, 1H), 3.13 (m, 2H), 2.78 (m, 1H), 2.64 (m, 1H), 2.00 (m, 1H), 1.79 (m, 2H), 1.44 (m, 2H) | | | | | |
| 13 | carboxyl | S | 1 | methyl | H | 1-acetyl-pyrrolidin-3-yl |
| | (400 MHz, $CDCl_3$) δ 10.13 (brs, 1H), 6.93 (s, 1H), 6.82 (s, 1H), 6.38 (s, 1H), 5.09 (m, 1H), 4.16 (m, 1H), 3.67 (m, 2H), 3.52 (m, 2H), 3.38 (m, 1H), 3.25 (m, 1H), 2.91 (m, 1H), 2.66 (m, 1H), 2.48 (s, 3H), 2.23 (m, 1H), 2.00 (m, 1H) | | | | | |
| 14 | carboxyl | S | 1 | H | H | c-Pen |
| | (400 MHz, $CDCl_3$); δ 11.74 (brs, 1H), 7.06 (s, 1H), 6.99 (m, 2H), 6.45 (s, 1H), 5.48 (m, 1H), 3.90 (m, 1H), 3.71 (m, 1H), 3.23 (m, 1H), 2.75 (m, 1H), 2.67 (m, 1H), 2.04 (m, 2H), 1.75 (m, 2H), 1.61-1.48 (m, 4H) | | | | | |
| 15 | carboxyl | R | 1 | phenoxy | H | (THP-4-yl)methyl |
| | (400 MHz, $CDCl_3$); δ 11.96 (brs, 1H), 7.30 (m, 2H), 7.03 (m, 4H), 6.60 (s, 1H), 6.20 (s, 1H), 5.36 (m, 1H), 3.93 (m, 1H), 3.73 (m, 1H), 3.35 (m, 2H), 3.23 (m, 1H), 3.06 (m, 2H), 2.72 (m, 1H), 2.62 (m, 1H), 1.92 (m, 1H), 1.73 (m, 2H), 1.40 (m, 2H) | | | | | |
| 16 | carboxyl | S | 1 | phenoxy | H | THP-4-yl |
| | (400 MHz, $CDCl_3$), δ 11.95 (brs, 1H), 7.28 (m, 2H), 7.06-6.96 (m, 4H), 6.58 (s, 1H), 6.24 (s, 1H), 5.33 (m, 1H), 3.98 (m, 2H), 3.75 (m, 1H), 3.58-3.47 (m, 3H), 2.23 (m, 1H), 2.78-2.62 (m, 2H), 2.04 (m, 2H), 1.26 (m, 2H) | | | | | |
| 17 | carboxyl | S | 2 | methyl | H | 4,4-difluorocyclohexane |
| | (400 MHz, $CDCl_3$); δ 11.94 (brs, 1H), 7.00 (s, 1H), 6.78 (s, 1H), 6.26 (s, 1H), 5.35 (m, 1H), 3.71 (m, 1H), 3.63 (m, 1H), 3.22 (m, 1H), 2.75 (m, 1H), 2.62 (m, 1H), 2.37 (s, 3H), 2.25 (m, 1H), 2.09-1.73 (m, 7H) | | | | | |
| 18 | carboxyl | S | 1 | chloro | H | (THP-4-yl)methyl |
| | (400 MHz, DMSO-$d_6$); δ 11.61 (br s, 1H), 6.85 (s, 1H), 6.75 (s, 1H), 6.21 (s, 1H). 6.15 (s, 1H), 4.91 (t, 1H), 3.90 (m, 2H). 3.65 (m, 1H). 3.41~3.20 (m, 4H), 3.05 (m, 2H), 2.80~2.66 (m, 2H), 1.88 (m, 1H), 1.76 (m, 2H), 1.31 (m, 2H), 1.09 (m, 1H) | | | | | |
| 19 | carboxyl | S | 1 | methyl | H | cyclobutyl |
| | (400 MHz, $CDCl_3$); δ 11.21 (br s, 1H), 6.66 (s, 1H), 6.61 (s, 1H), 6.00 (s, 1H), 4.89 (br s, 1H), 3.95 (m, 1H), 3.63 (m, 1H), 3.35 (m, 2H), 2.67 (m, 2H), 2.50 (s, 3H), 2.42 (m, 2H), 1.80 (m, 4H) | | | | | |
| 20 | carboxyl | S | 1 | methyl | H | tetrahydrofuran-3-yl |
| | (400 MHz, $CDCl_3$), δ 11.829d, 1H), 6.95 (s, 1H), 6.79 (s, 1H), 6.20 (d, 1H), 5.30 (br s, 1H), 4.15 (m, 1H), 4.05~3.75 (m, 5H), 3.66 (m, 1H), 3.19 (s, 1H), 2.79~2.61 (m, 2H), 2.37 (s, 3H), 2.23 (m, 1H), 1.98 (m, 1H) | | | | | |
| 21 | carboxyl | S | 1 | methyl | H | cyclopropylmethyl |
| | (400 MHz, $CDCl_3$/MeOH-$d_4$); δ 11.24 (br s, 1H), 6.84 (s, 1H), 6.77 (s, 1H), 6.25 (s, 1H), 5.05 (m, 1H), 3.56 (m, 1H), 3.15 (m, 2H), 3.03 (m, 2H), 2.78 (m, 1H), 2.63 (m, 1H), 2.34 (s 3H), 1.23 (m, 1H), 1.18 (m, 1H), 0.52 (m, 2H), 0.24 (m, 2H) | | | | | |
| 22 | carboxyl | S | 1 | methyl | H | (THP-4-yl)methyl |
| | (400 MHz, $CDCl_3$); δ 11.92 (br s, 1H), 6.98 (s, 1H), 6.77 (s, 1H), 6.22 (s, 1H), 6.29 (br s, 1H), 3.96 (m, 2H), 3.70 (m, 1H), 3.37 (m, 2H), 3.18 (m, 1H), 3.08 (m, 2H), 2.729m, 1H), 2.56 (m, 1H), 2.37 (s, 3H), 1.91 (m, 1H), 1.75 (m, 2H), 1.41 (m, 2H) | | | | | |
| 23 | carboxyl | S | 1 | methyl | H | (c-Pen)methyl |
| | (400 MHz, DMSO-$d_6$); δ 11.35 (br s, 1H), 6.67 (s, 1H), 6.61 (s, 1H), 6.09 (s, 1H), 5.81 (br s, 1H), 4.90 (m, 1H), 3.64 (m, 1H), 3.21 (m, 1H), 3.05 (m, 2H), 2.77~2.69 (m, 2H), 2.28 (s, 3H), s.23 (m, 1H), 1.85 (m, 2H), 1.65~1.58 (m, 4H), 1.32 (m, 2H) | | | | | |
| 24 | HO— | S | 2 | methyl | H | THP-4-yl |
| | (400 MHz, $CDCl_3$); δ 10.37 (br s, 1H), 6.84 (s, 1H), 6.82 (s, 1H), 6.32 (s, 1H), 4.64 (m, 1H), 4.00 (m, 4H), 3.63~3.51 (m, 4H), 3.11 (t, 1H), 2.38 (s, 3H), 2.05 (m, 4H), 1.51 (m, 2H) | | | | | |
| 25 | carboxyl | S | 1 | methyl | H | THP-4-yl |
| | (400 MHz, DMSO-$d_6$); δ 11.77 (br s, 1H), 6,98 (sm 2H), 6.67 (s, 1H), 4.95 (m, 1H), | | | | | |

-continued

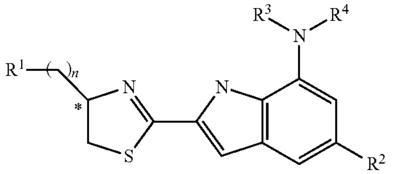

| Example | $R^1$ | * | n | $R^2$ | $R^3$ | $R^4$ | $H^1$ NMR data |
|---|---|---|---|---|---|---|---|
| | | | | | | | 4.02 (m, 2H), 3.72 (m, 2H), 3.42~3.29 (m, 3H), 2.86~2.69 (m, 2H), 2.50 (s, 1H), 1.94 (m, 2H), 162 (m, 2H) |
| 26 | carboxyl | S | 1 | methyl | H | c-Pen | (400 MHz, DMSO-$d_6$); δ 11.88 (br s, !H), b7.09 (s, 1H), 7.04 (s, 1H), 6.74 (s, 1H), 4.94 (m, 1H), 3.98 (m, 1H), 3.73 (m, 1H), 3.47 (m, 1H), 2.87~2.70 (m, 2H), 2.51 (s, 3H), 1.93 (m, 2H), 1.76~1.56 (m, 6H) |
| 27 | H | — | 0 | H | H | (thiophen-3-yl)methyl | (400 MHz, $CDCl_3$); δ 9.67 (s, 1H), 7.32 (dd, 1H), 7.21 (m, 1H), 7.13 (d, J = 8.0 Hz, 1H), 7.07 (d, J = 5.2 Hz, 1H), 7.02 (t, J = 8.0 Hz, 1H), 6.91 (s, 1H), 6.56 (d, J = 7.6 Hz, 1H), 4.42 (s, 2H), 4.36 (m, 2H), 3.36 (m, 2H) |
| 28 | H | — | 0 | H | H | tetrahydrofuran-3-yl | (400 MHz, $CDCl_3$) δ 10.36 (s, 1H), 7.10 (d, J = 8.0 Hz, 1H), 7.00 (t, J = 8.0 Hz, 1H), 6.99 (s, 1H), 6.45 (d, J = 7.6 Hz, 1H), 4.41 (m, 2H), 4.18 (s, 1H), 3.98~3.73 (m, 4H), 3.47 (m, 2H), 2.28 (m, 1H), 1.90 (m, 1H) |
| 29 | HO— | R | 1 | H | H | cyclohexyl | (500 MHz, $CDCl_3$) δ 11.17~11.08 (m, 1H), 7.09 (m, 1H), 6.99 (t, 1H), 6.96 (s, 1H), 6.52 (m, 1H), 4.72 (m, 1H), 4.04 (m, 1H), 3.75 (m, 1H), 3.65 (m, 1H), 3.51 (m, 1H), 3.40 (m, 1H), 1.90 (m, 2H), 1.60~1.49 (m, 4H), 1.4~1.24 (m, 2H) |
| 30 | carboxyl | R | 2 | H | H | THP-4-yl | (400 MHz, DMSO-$d_6$); δ 12.42 (br s, 1H), 11.34 (s, 1H), 6.80 (d, 1H), 6.72 (s, 1H), 6.33 (d, 1H), 5.79 (d, 1H), 4.86 (q, 1H), 3.88 (m, 2H), 3.60-3.52 (m, 2H), 3.42 (t, 2H), 3.17 (m, 1H), 2.74 (m, 1H), 2.59 (m, 1H), 1.94 (m, 2H), 1.39 (m, 2H) |
| 31 | HO— | R | 1 | chloro | H | isopropyl | (400 MHz, $CDCl_3$); δ 10.89 (br s, 1H), 7.00 (s, 1H), 6.83 (s, 1H), 6.43 (s, 1H), 4.75 (m, 1H), 4.04 (dd, 1H), 3.71 (dd, 1H), 3.61 (m, 1H), 3.43 (dd, 1H), 1.09 (t, 6H) |
| 32 | methyl | R | 0 | H | H | THP-4-yl | (400 MHz, $CDCl_3$); δ 11.13 (br s, 1H), 7.08~6.99 (m, 3H), 6.53 (d, 1H), 4,76 (m, 114), 4.09 (m, 2H), 3.72 (m, 1H), 3.63 (m, 3H), 3.12 (m, 1H), 2.13 (m, 2H), 1.68 (m, 2H), 1.48 (d, 3H) |
| 33 | HO— | R | 1 | (morpholin-4-yl)methyl | H | c-Pen | (400 MHz, $CDCl_3$); δ 10.77 (br s, 1H), 7.06 (s, 1H), 6.95 (s, 1H), 6.62 (s, 1H), 4.80 (m, 1H), 4.11 (m, 1H), 3.99 (m, 2H), 3.76 (m, 1H), 3.75 (m, 4H), 3.51 (s, 2H), 3.45 (m, 5H), 2.51 (br s, 4H), 2.00 (m, 2H), 1.45 (m, 2H) |
| 34 | HO— | R | 1 | (dimethylamino) methyl | H | c-Pen | (400 MHz, CDCl3); δ 10.86 (br s, 1H), 6.96 (s, 1H), 6.88 (s, 1H), 6.51 (s, 1H), 4.75 (m, 1H), 4.37 (m, 2H), 3.85 (m, 1H), 3.71 (m, 1H), 3.50 (s, 2H), 3.42 (m, 2H), 2.27 (s, 6H) 1.96 (m, 214), 1.59 (m, 4H), 1.39 (m, 2H) |
| 35 | HO— | R | 1 | (pyrrol-3-yl)methyl | H | c-Pen | (400 MHz, $CDCl_3$); δ 11.04 (1H, br), 7.85 (1H, br), 6.90~6.85 (2H, m), 6.62 (1H, s), 6.36 (1H, s), 6.13 (1H, m), 6.01 (1H, s), 4.77~4.67 (1H, m), 4.08~4.01 (1H, m), 3.99 (2H, s), 3.78~3.65 (2H, m), 3.52~3.38 (2H, m), 1.98~1.85 (2H, m), 1.65~1.47 (4H, m), 1.42~1.33 (1H, m), 1.33~1.26 (1H, m) |
| 36 | HO— | R | 1 | (1,3-imidazol-1-yl)methyl | H | c-Pen | (400 MHz, $CDCl_3$); δ 11.10 (1H, br), 8.21 (1H, s), 7.25 (1H, s), 7.23 (1H, s), 6.87 (3H, br), 6.16 (1H, s), 5.05 (2H, s), 4.81~4.73 (1H, m), 4.00~3.93 (1H, m), 3.79~1.73 (1H, m), 3.73~3.67 (1H, m), 3.49~3.37 (2H, m), 1.98~1.88 (2H, m), 1.66~1.53 (4H, m), 1.43~1.37 (2H, m) |
| 37 | HO— | R | 1 | (pyrazol-1-yl)methyl | H | c-Pen | (500 MHz, $CDCl_3$); δ 11.11 (1H, br), 7.52 (1H, d, J = 1.85 Hz), 7.34 (1H, d, J = 2.45 Hz), 6.93 (1H, s), 6.88 (1H, s), 6.34 (1H, s), 6.22 (1H, m), 5.31 (2H, s), 4.75~4.67 (1H, m), 4.02~3.95 (1H, m), 3.70~3.61 (2H, m), 3.47~3.38 (2H, m), 1.92~1.81 (2H, m), 1.60~1.46 (4H, m), 1.33~1.20 (2H, m) |
| 38 | HO— | R | 1 | acetylamino | H | c-Pen | (400 MHz, $CDCl_3$); δ 10.71 (br s, 1H), 7.26 (s, 1H), 7.23 (s, 1H), 6.88 (s, 1H), 4.77 (m, 1H), 4.02 (m, 1H), 3.80 (m, 1H), 3.73 (m, 1H), 3.47 (m, 2H), 2.20 (s, 3H), 2.04 (m, 2H), 1.60 (m, 4H), 1.44 (m, 2H) |
| 39 | carboxyl | R | 1 | phenoxymethyl | H | c-Pen | (500 MHz, $CDCl_3$); δ 11.79 (1H, br), 7.29~7.26 (2H, m), 7.03~7.00 (3H, m), 6.99 (1H, s), 6.93 (1H, m), 6.48 (1H, m), 5.39~5.30 (1H, m), 5.07 (2H, s), 3.94~3.86 (1H, m), 3.75~3.68 (1H, m), 3.24~3.18 (1H, m), 2.78~2.70 (1H, m), 2.68~2.61 (1H, m), 2.05~1.96 (2H, m), 1.79~4.70 (2H, m), 1.66~1.56 (4H, m) |

-continued

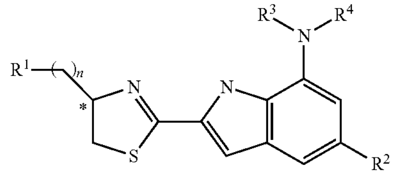

| Example | $R^1$ | * | n | $R^2$ | $R^3$ | $R^4$ |
|---|---|---|---|---|---|---|
| | | | | $H^1$ NMR data | | |
| 40 | $MeO_2C$— | R | 1 | (pyrrolidin-1-yl)methyl | H | c-Pen |
| | | | | (500 MHz, $CDCl_3$); δ 10.13 (1H, br), 6.97 (1H, s), 6.88 (1H, s), 6.73 (1H, s), 5.05~4.95 (1H, m), 4.04 (2H, s), 3.73 (3H, s), 3.70~3.60 (1H, m), 3.49 (4H, s), 3.25~3.15 (1H, m), 3.10~2.95 (1H, m), 2.90~2.85 (1H, m), 2.71~2.65 (1H, m) 2.15-1.53 (12H, m) | | |
| 41 | isobutyl | R | 0 | chloro | H | c-Pen |
| | | | | (500 MHz, $CDCl_3$); δ 10.68 (br s, 1H), 7.00 (s, 1H), 6.89 (s, 1H), 6.42 (s, 1H), 4.54 (t, 1H), 4.40 (m, 1H), 4.07 (t, 1H), 3.84 (m, 1H), 2.04 (m, 2H), 1.80~1.32 (m, 9H), 0.89 (d, 3H), 0.83 (d, 3H) | | |
| 42 | $EtO_2C$— | R | 2 | H | H | c-Pen |
| | | | | (400 MHz, $CDCl_3$); δ 9.79 (br s, 1H), 7.05 (m, 1H), 6.96 (m, 1H), 6.91 (s, 1H), 6.52 (d, J = 8 Hz, 1H), 4.72 (m, 1H), 4.08 (m, 2H), 3.90 (m, 1H), 3.55 (t, 1H), 3.12 (t, 1H), 2.52 (m, 2H), 2.04 (m, 4H), 1.63 (m, 2H), 1.53 (m, 4H), 1.28 (m, 1H), 1.20 (t, 3H) | | |
| 43 | HO— | R | 1 | H | H | (3R)-1-acetylpyrrolidin-3-yl |
| | | | | (500 MHz, $CDCl_3$); δ 10.86 (br s, 1H), 7.03 (m, 1H), 7.00 (m, 1H), 6.88 (d, 1H), 6.43 (m, 1H), 4.74 (m, 1H), 4.25 (m, 1H), 4.17 (m, 1H), 3.95 (m, 1H), 3.69 (m, 2H), 3.62 (m, 1H), 3.51~3.42 (m, 5H), 3.25 (m, 1H), 2.04 (m, 2H) | | |
| 44 | ethyl | R | 0 | fluoro | H | c-Pen |
| | | | | (500 MHz, $CDCl_3$); δ 11.22 (br s, 1H), 6.88 (s, 1H), 6.63 (d, 1H), 4.65 (m, 1H), 3.99 (br s, 1H), 3.75 (m, 1H), 3.53 (m, 1H), 3.117 (m, 1H), 2.02~1.94 (m, 2H), 1.77 (m, 1H), 1.63 (m, 5H), 1.44 (m, 1H), 1.28 (m, 1H), 0.94 (m, 3H) | | |
| 45 | HO— | R | 1 | fluoro | Me | c-Pen |
| | | | | (500 MHz, $CDCl_3$); δ 10.28 (br s, 1H), 6.92 (d, 1H), 6.70 (d, 1H), 6.59 (s, 1H), 4.71 (m, 1H), 4.22 (dd, 1H), 3.75 (dd, 1H), 3.69 (m,1 H), 3.59 (t, 1H), 3.35 (t, 1H), 2.68 (s, 3H), 1.82 (m, 1H), 1.72 (m, 1H), 1.62~1.40 (m, 6H) | | |
| 46 | $MeO_2C$— | S | 1 | ethoxy | H | c-Pen |
| | | | | (400 MHz, $CDCl_3$); δ 10.66 (br s, 1H), 6.82 (s, 1H), 6.41 (s, 1H), 6.17 (s, 1H), 5.08 (m, 1H), 4.01 (m, 2H), 3.80 (m, 1H), 3.67 (m, 1H), 3.49 (s, 3H), 3.20 (dd, 1H), 2.85 (dd, 1H), 2.65 (dd, 1H), 2.02 (m, 1H), 1.66~1.53 (m, 4H), 1.45~1.33 (m, 5H) | | |
| 47 | carboxyl | S | 1 | ethoxy | H | c-Pen |
| | | | | NMR (400 MHz, $CDCl_3$); δ 11.99 (br s, 1H), 6.95 (s, 1H), 6.34 (s, 1H), 6.11 (s, 1H), 5.33 (m, 1H), 4.04 (m, 2H), 3.83 (m, 1H), 3.69 (m, 1H), 3.18 (d, 1H), 2.73 (m, 1H), 2.59 (m, 1H), 2.00 (m, 2H), 1.73 (m, 2H), 1.59 (m, 4H), 1.43 (m, 3H) | | |
| 48 | HO— | S | 2 | ethoxy | H | c-Pen |
| | | | | (400 MHz, $CDCl_3$); δ 10.64 (br s, 1H), 6.82 (s, 1H), 6.39 (d, 1H), 6.15 (d, 1H), 4.69 (br s, 1H), 4.60 (m, 1H), 4.06~3.84 (m, 5H), 3.54 (m, 1H), 3.10 (m, 1H), 2.08~1.94 (m, 4H), 1.70 (m, 2H), 1.58 (m, 4H), 1.40 (m, 3H) | | |
| 49 | $EtO_2C$- | R | 0 | methyl | H | c-Pen |
| | | | | (400 MHz, $CDCl_3$) δ 9.74 (br s, 1H), 6.85 (d, J = 4 Hz, 2H), 6.37 (s, 1H), 5.33 (t, 1H), 4.23 (m, 2H), 3.87 (m, 1H), 3.71 (m, 2H), 2.39 (s, 3H), 2.03 (m, 2h), 1.68 (m, 2H), 1.61 (m, 2H), 1.47 (m, 2h), 1.26 (t, 3H) | | |
| 50 | carboxyl | S | 1 | phenoxy | H | c-Pen |
| | | | | (400 MHz, DMSO-$d_6$, Na salt); δ 11.85 (br s, 1H), 7.31 (t, 2H), 7.01 (t, 1H), 6.93 (d, J = 8 Hz, 2H), 6.64 (s, 1H), 6.48 (d, J = 4 Hz, 1H), 6.39 (s, 1H), 5.97 (s, 1H), 4.93 (m, 1H), 3.75 (m, 1H), 3.55 (t, 1H), 3.20 (q, 1H), 2.62 (dd, 1H), 2.15 (q, 1H), 1.90 (m, 2H), 1.72 (m, 2H), 1.60 (m, 4H) | | |
| 51 | HO— | R | 1 | H | H | THP-4-yl |
| | | | | (400 MHz, $CDCl_3$); δ 10.91 (br s, 1H), 7.01~6.91 (m, 3H), 6.48 (d, J = 7.2 Hz, 1H), 4.86 (m, 1H), 4.34 (m 2H), 4.00 (m, 2H), 3.61 (m, 1H), 3.54 (m, 3H), 3.31 (m, 1H), 2.05 (m, 2H), 1.55 (m, 2H), 1.16 (s, 9H) | | |
| 52 | HO— | R | 1 | H | H | THF-3-yl |
| | | | | (500 MHz, $CDCl_3$); δ 10.58 (br s, 1H), 7.14 (d, J = 7.95 Hz, 1H), 7.00 (m, 1H), 6.94 (m, 1H), 6.48 (d, J = 7.35 Hz, 1H), 4.79 (m, 1H), 4.15~3.95 ((m, 3H), 3.90~3.65 (m, 4H), 3.50 ~3.39 (m, 2H), 2.20 (m, 1H), 1.83 (m, 1H) | | |
| 53 | HO— | R | 1 | H | H | 1-(methanesulfonyl)pyrrolidin-3-yl |
| | | | | (500 MHz, $CDCl_3$); δ 10.50 (br s, 1H), 7.15 (d, J = 7.95 Hz, 1H), 7.00 (dd, 1H), 6.93 (s, 1H), 6.46 (d, J = 7.35 Hz, 1H), 4.77 (m, 1H), 4.18 (m, 1H), 4.08 (dd, 1H), 3.75 (dd, 1H), 3.59-3.36 (m, 6H), 3.48 (s, 3H), 2.27 (m, 1H), 1.95 (m, 1H) | | |
| 54 | HO— | R | 1 | fluoro | H | c-Pen |
| | | | | (400 MHz, $CDCl_3$); δ 10.73 (br s, 1H), 6.91 (s, 1H), 6.72 (m, 1H), 6.33 (m, 1H), 4.78 (m, 1H), 4.12 (m, 1H), 3.97 (br s, 1H), 3.79 (m, 1H), 3.75 (m, 1H), 3.49 (m, 2H), 2.01 (m, 2H), 1.62 (m, 4H), 1.41 (m, 2H) | | |
| 55 | HO— | R | 1 | fluoro | H | THP-4-yl |
| | | | | (400 MHz, $CDCl_3$); δ 10.45 (br s, 1H), 6.90 (s, 1H), 6.75 (m, 1H), 6.34 (m, 1H), | | |

-continued

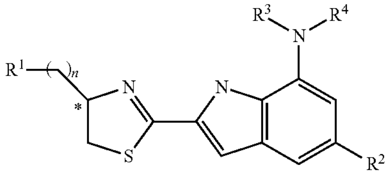

| Example | $R^1$ | * | n | $R^2$ | $R^3$ | $R^4$ |
|---|---|---|---|---|---|---|
| | | | | $H^1$ NMR data | | |
| | 4.82 (m, 1H), 4.12 (m, 1H), 4.01 (m, 2H), 3.94 (m, 1H), 3.78 (m, 1H), 3.54~3.43 (m, 5H), 2.03 (m, 2H), 1.50 (m, 2H) | | | | | |
| 56 | HO— | R | 2 | chloro | H | c-Pen |
| | (500 MHz, $CDCl_3$); δ 10.53 (br s, 1H), 7.24 (s, 1H), 6.84 (d, 1H), 6.45 (s, 1H), 4.74 (m, 1H), 4.06 (m, 1H), 3.81 (m, 1H), 3.71 (m, 1H), 3.45 (dd, 2H), 1.99 (m, 2H), 1.60 (m, 4H), 1.37 (m, 2H) | | | | | |
| 57 | HO— | R | 1 | chloro | H | 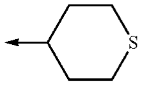 |
| | (400 MHz, $CDCl_3$); δ 10.87 (br s, 1H), 7.01 (s, 1H), 6.89 (s, 1H), 6.40 (s, 1H), 4.80 (m, 1H), 4.10 (m, 1H), 3.80 (m, 1H), 3.50 (m, 2H), 3.32 (m, 1H), 2.76 (m, 4H), 2.29 (m, 2H), 1.56 (m, 2H) | | | | | |
| 58 | HO— | R | 1 | bromo | H | c-Pen |
| | (400 MHz, $CDCl_3$); δ 10.59 (br s, 1H), 7.23 (s, 1H), 6.88 (s, 1H), 6.64 (d, 1H), 4.77 (m, 1H), 4.14 (m, 1H), 3.82 (m, 1H), 3.76 (m, 1H), 3.49 (dd, 2H), 2.04 (m, 2H), 1.65 (m, 4H), 1.41 (m, 2H) | | | | | |
| 59 | HO— | R | 1 | bromo | H | THP-4-yl |
| | (400 MHz, $CDCl_3$); δ 10.53 (br s, 1H), 7.25 (s, 1H), 6.87 (s, 1H), 6.63 (d, 1H), 4.80 (m, 1H), 4.14 (m, 1H), 4.03 (m, 2H), 3.79 (m, 1H), 3.56-3.3.44 (m, 4H), 2.02 (m, 2H), 1.45 (m, 2H) | | | | | |
| 60 | HO— | R | 1 | methoxy | H | c-Pen |
| | (500 MHz, DMSO-$d_6$); δ 11.23 (br s, 1H), 6.60 (s, 1H), 6.23 (s, 1H), 5.89 (m, 1H), 5.84 (m, 1H), 4.96 (m, 1H), 4.65 (m, 1H), 3.77 (m, 1H), 3.70 (m, 1H), 3.45 (m, 1H), 3.33 (m, 1H), 3.29 (s, 3H), 1.91 (m, 214), 1.67 (m, 2H), 1.53 (m, 4H) | | | | | |
| 61 | HO— | R | 1 | (pyridin-3-yl)oxy | H | c-Pen |
| | (400 MHz, $CDCl_3$); δ 11.16 (br s, 1H), 8.42 (d, 1H), 8.28 (m, 1H), 7.30 (m, 1H), 7.22 (m, 1H), 6.88 (s, 1H), 6.67 (d, 1H), 6.28 (d, 1H), 4.83 (m, 1H), 4.02 (m, 1H), 3.75 (m, 2H), 3.46 (m, 2H), 1.97 (m, 2H), 1.63 (m, 4H), 1.43 (m, 2H) | | | | | |
| 62 | HO— | R | 1 | (pyridin-3-yl)oxy | H | THP-4-yl |
| | (400 MHz, $CDCl_3$); δ 10.96 (br s, 1H), 8.36 (d, J = 2.4 Hz, 1H), 8.26 (m, 1H), 7.27 (m, 1H), 7.19 (m, 1H), 6.83 (s, 1H), 6.63 (d, J = 1.6 Hz, 1H), 6.24 (d, J = 1.6 Hz, 1H), 4.81 (m, 1H), 4.01~3.94 (m, 3H), 3.75 (m, 1H), 3.47 (s, 3H), 3.48~3.29 (m, 5H), 1.93 (m, 2H), 1.52 (m, 2H) | | | | | |
| 63 | HO— | R | 1 | methanesulfonyl-methyl | H | c-Pen |
| | (500 MHz, $CDCl_3$); δ 11.10 (brs, 1H), 7.01 (s, 1H), 6.88 (m, 1H), 6.49 (s, 1H), 4.76 (m, 1H), 4.26 (s, 2H), 3.99 (m, 1H), 3.79 (m, 1H), 3.68 (m, 1H), 3.43 (m, 2H), 2.73 (s, 3H), 1.96 (m, 2H), 1.57 (m, 4H), 1.35 (m, 2H) | | | | | |
| 64 | HO— | R | 1 | (isoindol-1,3-dion-2-yl)methyl | H | c-Pen |
| | (500 MHz, DMSO-$d_6$); δ 11.30 (brs, 1H), 8.83 (brs, 1H), 7.69 (m, 1H), 7.51 (m, 1H), 7.44 (m, 2H), 6.78 (s, 1H), 6.67 (d, 1H), 6.28 (s, 1H), 5.81 (s, 1H), 4.96 (brs, 1H), 4.67 (m, 1H), 4.37 (d, 2H), 3.83 (m, 1H), 3.70 (m, 1H), 3.52 (m, 1H), 3.46 (m, 1H), 1.94 (m, 2H), 1.68 (m, 2H), 1.54 (m, 4H) | | | | | |
| 65 | $MeO_2C$— | R | 1 | chloro | H | THP-4-yl |
| | (400 MHz, DMSO-$d_6$); δ 11.52 (s, 1H), 6.81 (s, 1H), 6.71 (s, 1H), 6.28 (s, 1H), 6.07 (d, 1H), 4.90 (m, 1H), 3.86 (m, 2H), 3.64 (s, 3H), 3.62 (m, 2H), 3.44 (t, 2H), 2.82-2.71 (m, 2H), 1.94 (m, 2H), 1.40 (m, 2H) | | | | | |
| 66 | carboxyl | R | 1 | chloro | H | THP-4-yl |
| | (400 MHz, DMSO-$d_6$); δ 12.43 (br s, 1H), 11.53 (s, 1H), 6.81 (s, 1H), 6.71 (s, 1H), 6.28 (s, 1H), 6.06 (d, 1H), 4.87 (m, 1H), 3.87 (m, 2H), 3.62 (m, 2H), 3.44 (t, 2H), 3.19 (m, 1H), 3.74 (m, 1H), 2.63 (m, 1H), 1.94 (m,. 2H), 1.41 (m, 2H) | | | | | |
| 67 | HO— | R | 2 | chloro | H | THP-4-yl |
| | (400 MHz, DMSO-$d_6$); δ 11.48 (s, 1H), 6.81 (s, 1H), 6.68 (s, 1H), 6.28 (s, 1H), 6.05 (d, 1H), 4.66 (q, 1H), 4,54 (t, 1H), 3.87 (m, 2H), 3.61-3.54 (m, 3H), 3.44 (t, 2H), 3.15 (m, 1H), 1.99-1.93 (m, 3H), 1.73 (m, 1H), 1.40 (m, 2H), 1.20 (m, 1H) | | | | | |
| 68 | carboxyl | R | 1 | bromo | H | c-Pen |
| | (400 MHz, $CDCl_3$); δ 12.50 (br s, 1H), 7.10 (sm 1H), 7.06 (s, 1H), 6.56 (s, 1H), 5.31 (m, 1H), 3.89 (m, 2H), 3.40 (m, 1H), 2.99 (m, 1H), 2.83 (m, 1H), 2.08 (m, 2H), 1.86 (m, 2H), 1.66 (m, 4H) | | | | | |

-continued

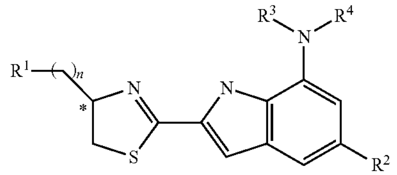

| Example | $R^1$ | * | n | $R^2$ | $R^3$ | $R^4$ |
|---|---|---|---|---|---|---|
| | | | $H^1$ NMR data | | | |
| 69 | HO— | R | 2 | bromo | H | c-Pen |
| | (400 MHz, $CDCl_3$); δ 10.42 (br s, 1H), 7.18 (s, 1H), 6.87 (s, 1H), 6.59 (d, 1H), 4.67 (m, 2H), 4.02 (m, 2H), 3.91 (m, 1H), 3.63 (m, 1H), 3.16 (t, 1H), 2.10 (m, 4H), 1.74 (m, 2H), 1.4 (m, 4H) | | | | | |
| 70 | HO— | R | 2 | bromo | H | THP-4-yl |
| | (400 MHz, $CDCl_3$); δ 10.50 (br s, 1H), 7.19 (s, 1H), 6.89 (s, 1H), 6.59 (d, 1H), 4.67 (m, 2H), 4.05 (m, 4H), 3.63 (m, 4H), 3.18 (t, 1H), 2.12 (m, 4H), 1.64 (m, 4H) | | | | | |
| 71 | carboxyl | R | 1 | fluoro | H | c-Pen |
| | (400 MHz, $CDCl_3$); δ 11.09 (br s, 1H), 6.73 (s, 1H), 6.45 (dd, 1H), 6.07 (dd, 1H), 4.98 (m, 1H), 3.79 (m, 1H), 3.59 (m, 1H), 3.16 (m, 1H), 2.79 (m, 1H), 2.60 (m, 1H), 1.96 (m, 2H), 1.71 (m, 2H), 1.58 (m, 4H) | | | | | |
| 72 | $EtO_2C$— | R | 1 | fluoro | H | c-Pen |
| | (400 MHz, $CDCl_3$); δ 10.71 (br s, 1H), 6.86 (s, 1H), 6.64 (dd, 1H), 6.23 (dd, 1H), 5.07 (m, 1H), 3.99 (q, 2H), 3.91 (m, 1H), 3.76 (m, 1H), 3.64 (m, 1H), 3.22 (m, 1H), 2.88 (m, 1H), 2.65 (m, 1H), 2.00 (m, 2H), 1.63 (m, 4H), 1.40 (m, 2H), 1.12 (t, 3H) | | | | | |
| 73 | HO— | R | 2 | fluoro | H | c-Pen |
| | (400 MHz, $CDCl_3$); δ 10.90 (br s, 1H), 6.91 (s, 1H), 6.65 (dd, 1H), 6.26 (dd, 1H), 4.68 (m, 1H), 4.08 (m, 2H), 3.88 (m, 1H), 3.62 (m, 1H), 3.15 (t, 1H), 2.10 (m, 4H), 1.74 (m, 2H), 1.62 (m, 4H) | | | | | |
| 74 | carboxyl | R | 1 | fluoro | H | THP-4-yl |
| | (400 MHz, DMSO-$d_6$); δ 11.45 (s, 1H), 6.75 (d, 1H), 6.22 (dd, 1H), 6.16 (d, J = 6.8 Hz, 1H), 4.91 (m, 1H), 3.88 (m, 2H), 3.66 (m, 1H), 3.61 (m, 1H), 3.48 (m, 2H), 3.22 (m, 1H), 2.80 (m, 1H), 2.65 (m, 1H), 2.99 (m, 2H), 1.40 (m, 2H) | | | | | |
| 75 | carboxyl | R | 1 | H | H | c-Pen |
| | (400 MHz, $CDCl_3$); δ 11.77 (br s, 1H), 7.04 (d, 1H), 6.97 (m, 2H), 6.43 (d, 1H), 5.34 (m, 1H), 3.88 (m, 1H), 3.69 (m, 1H), 3.19 (m, 1H), 2.72 (m, 1H), 2.60 (m, 1H), 2.01 (m, 2H), 1.74 (m, 2H), 1.59 (m, 4H) | | | | | |
| 76 | $EtO_2C$— | R | 1 | H | H | c-Pen |
| | (400 MHz, $CDCl_3$); δ 10.12 (br s, 1H), 7.05 (m, 1H), 6.99 (m, 1H), 6.91 (d, 1H), 6.51 (d, 1H), 5.07 (m, 1H), 4.09 (q, 2H), 3.87 (m, 1H), 3.65 (m, 1H), 3.21 (m, 1H), 2.86 (m, 1H), 2.65 (m, 1H), 2.01 (m, 2H), 1.74 (m, 2H), 1.62 (m, 4H), 1.46 (m, 2H), 1.81 (t, 3H) | | | | | |
| 77 | HO— | R | 2 | H | H | c-Pen |
| | (400 MHz, DMSO-$d_6$); δ 11.28 (s, 1H), 6.77-6.74 (m, 2H), 6.69 (s, 1H), 6.25 (d, 1H), 5.78 (d, 1H), 4.65 (q, 1H), 4.53 (t, 1H), 3.82 (m, 1H), 3.60 (m, 2H), 3.51 (m, 1H), 3.11 (m, 1H), 1.99-1.91 (m, 3H), 1.75-1.67 (m, 3H), 1.56-1.54 (m, 4H) | | | | | |
| 78 | carboxyl | R | 0 | H | H | THP-4-yl |
| | (400 MHz, DMSO-$d_6$); δ 12.42 (br s, 1H), 11.34 (s, 1H), 6.80 (d, 1H), 6.72 (s, 1H), 6.33 (d, 1H), 5.79 (d, 1H), 4.86 (q, 1H), 3.88 (m, 2H), 3.60-3.52 (m, 2H), 3.42 (t, 2H), 3.17 (m, 1H), 2.74 (m, 1H), 2.59 (m, 1H), 1.94 (m, 2H), 1.39 (m, 2H) | | | | | |
| 79 | HO— | R | 2 | H | H | THP-4-yl |
| | (400 MHz, DMSO-$d_6$); δ 11.29 (s, 1H), 6.79 (m, 2H), 6.70 (s, 1H), 6.33 (d, 1H), 5.76 (d, 1H), 4.66 (q, 1H), 4.54 (t, 1H), 3.88 (m, 2H), 3.62-3.59 (m, 3H), 3.53 (t, 1H), 3.43 (m, 2H), 3.12 (m, 1H), 1.96 (m, 3H), 1.75 (m, 1H), 1.40 (m, 2H) | | | | | |
| 80 | $MeO_2C$— | R | 1 | methoxy | H | c-Pen |
| | (400 MHz, DMSO-$d_6$); δ 11.24 (s, 1H), 6.62 (s, 1H), 6.22 (s, 1H), 5.89 (d, 1H), 5.84 (s, 1H), 4.83 (q, 1H), 3.77 (m, 1H), 3.64 (s, 3H), 3.59 (s, 3H), 3.56 (m, 1H), 3.15 (m, 1H), 2.69 (m, 1H), 2.58 (m, 1H), 1.90 (m, 2H), 1.67 (m, 2H), 1.51 (m, 4H) | | | | | |
| 81 | carboxyl | R | 1 | methoxy | H | c-Pen |
| | (400 MHz, DMSO-$d_6$); δ 12.54 (br s, 1H), 11.21 (s, 1H), 6.63 (s, 1H), 6.23 (s, 1H), 5.89 (d, 1H), 5.84 (s, 1H), 4.84 (q, 1H), 3.77 (m, 1H), 3.64 (s, 3H), 3.56 (m, 1H), 3.15 (m, 1H), 2.69 (m, 1H), 2.58 (m, 1H), 1.90 (m, 2H), 1.67 (m, 2H), 1.52 (m, 4H) | | | | | |
| 82 | carboxyl | R | 1 | methoxy | H | THP-4-yl |
| | (500 MHz, DMSO-$d_6$); δ 11.21 (br s, 1H), 6.64 (m, 1H), 6.26 (m, 1H), 5.95 (m, 1H), 5.8 4(m, 1H), 4.85 (m, 1H), 3.85 (m, 1H), 3.64 (s, 3H), 3.63-3.49 (m, 2H), 3.43 (m, 2H), 3.17 (m, 1H), 2.73 (m, 1H), 2.62 (m, 1H), 1.94 (m, 2H), 1.72 (m, 1H), 1.38 (m, 2H) | | | | | |
| 83 | carboxyl | R | 1 | ethoxy | H | c-Pen |
| | (400 MHz, DMSO-$d_6$); δ 11.24 (br s, 1H), 6.65 (d, J = 2.0 Hz, 1H), 6.26 (d, J = 2.0 Hz, 1H), 5.92 (d, J = 6.0 Hz, 1H), 5.88 (d, J = 2.0 Hz, 1H), 4.89 (m, 1H), 3.94 (q, 2H), 3.81 (m, 1H), 3.65 (m, 1H), 3.20 (m, 1H), 2.74 (m, 1H), 2.62 (m, 1H), 1.94 (m, 2H), 1.72 (m, 2H), 1.61 (m, 4H), 1.31 (t, 3H) | | | | | |
| 84 | carboxyl | R | 1 | O(n-Pr) | H | c-Pen |
| | (500 MHz, $CDCl_3$); δ 12.79 (br s, 1H), 7.05 (s, 1H), 6.26 (s, 1H), 6.22 (s, 1H), 5.14 (br s, 1H), 3.88 (m, 3H), 3.41 (m, 2H), 3.07 (m, 1H), 2.83 (m, 1H), 2.03 (m, 2H), 1.82 (m, 3H), 1.69 (m, 2H), 1.60 (m, 2H), 1.04 (t, 3H) | | | | | |

-continued

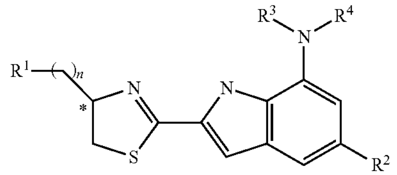

| Example | $R^1$ | * | n | $R^2$ | $R^3$ | $R^4$ |
|---|---|---|---|---|---|---|
| | | | | $H^1$ NMR data | | |
| 85 | carboxyl | R | 1 | phenoxy | H | c-Pen |
| | (400 MHz, $CDCl_3$); δ 11.92 (br s, 1H), 7.28 (m, 2H), 7.00 (m, 4H), 6.56 (s, 1H), 6.22 (s, 1H), 5.34 (br s, 1H), 3.81 (br s, 1H), 3.70 (m, 1H), 3.22 (d, J = 12.0 Hz, 1H), 2.76~2.62 (m, 2H), 1.96 (m, 2H), 1.73 (m, 2H), 1.58 (m, 4H) | | | | | |
| 86 | carboxyl | R | 1 | phenoxy | H | THP-4-yl |
| | (400 MHz, $CDCl_3$); δ 11.98 (br s, 1H), 7.28 (m, 2H), 7.00 (m, 4H), 6.58 (s, 1H), 6.22 (s, 1H), 5.34 (br s, 1H), 3.98 (br s, 2H), 3.70 (m, 1H), 3.50 (m, 3H), 3.21 (m, 2H), 2.74 (m, 1H), 2.66 (m, 1H), 2.05 (m, 2H), 1.58 (m, 2H) | | | | | |
| 87 | $MeO_2C$— | R | 1 | (pyridin-3-yl)oxy | H | c-Pen |
| | (400 MHz, $CDCl_3$); δ 10.89 (br s, 1H), 8.41 (d, 1H), 8.26 (m, 1H), 7.27 (m, 1H), 7.19 (m, 1H), 6.85 (s, 1H), 6.62 (d, 1H), 6.22 (m, 1H), 5.04 (m, 1H), 4.13 (br s, 1H), 3.78 (m, 1H), 3.65 (m, 1H), 3.59 (s, 3H), 3.20 (m, 1H), 2.83 (m, 1H), 2.67 (m, 1H), 1.98 (m, 2H), 1.61 (m, 4H), 1.46 (m, 2H) | | | | | |
| 88 | carboxyl | R | 1 | (pyridin-3-yl)oxy | H | c-Pen |
| | (400 MHz, $CDCl_3$); δ 11.86 (br s, 1H), 8.40 (d, 1H), 8.26 (m, 1H), 7.25 (m, 1H), 7.17 (m, 1H), 6.96 (s, 1H), 6.57 (d, 1H), 6.18 (d, 1H), 5.33 (br s, 1H), 3.80 (br s, 1H), 3.70 (m, 1H), 3.21 (m, 1H), 2.73 (m, 1H), 2.65 (m, 1H), 1.96 (m, 2H), 1.72 (m, 2H), 1.58 (m, 4H) | | | | | |
| 89 | MeO2C- | R | 1 | (pyridin-3-yl)oxy | H | THP-4-yl |
| | (400 MHz, DMSO-$d_6$); δ 11.48 (br s, 1H), 8.30 (d, 1H), 8.25 (m, 1H), 7.34 (m, 1H), 7.29 (m, 1H), 6.76 (d, 1H), 6.46 (d, 1H), 6.18 (d, 1H), 4.93 (m, 1H), 3.87 (m, 3H), 3.66 (s, 3H), 3.59 (m, 1H), 3.44 (m, 2H), 3.23 (m, 1H), 2.81 (m, 2H), 1.95 (m, 2H), 1.43 (m, 2H) | | | | | |
| 90 | carboxyl | R | 1 | (pyridin-3-yl)oxy | H | THP-4-yl |
| | (400 MHz, MeOH-$d_4$); δ 8.14 (s, 1H), 8.07 (s, 1H), 7.25 (m, 2H), 6.76 (s, 1H), 6.45 (s, 1H), 6.12 (d, 1H), 4.84 (m, 1H), 3.85 (m, 1H), 3.83 (m, 1H), 3.53 (m, 1H), 3.40 (m, 2H), 3.21 (m, 2H), 3.12 (m, 1H), 2.73 (m, 1H), 2.59 (m, 1H), 1.93 (m, 2H), 1.46 (m, 2H) | | | | | |
| 91 | $MeO_2C$— | R | 1 | methyl | H | c-Pen |
| | (400 MHz, DMSO-$d_6$); δ 11.19 (s, 1H), 6.62 (s, 1H), 6.55 (s, 1H), 6.07 (s, 1H), 5.75 (d, 1H), 4.88 (q, 1H), 3.79 (m, 1H), 3.63-3.57 (m, 5H), 3.17 (m, 1H), 2.82-2.73 (m, 2H), 2.23 (s, 3H), 1.94 (m, 2H), 1.68 (m, 2H), 1.55 (m, 3H) | | | | | |
| 92 | carboxyl | R | 1 | methyl | H | c-Pen |
| | (400 MHz, DMSO-$d_6$); δ 12.42 (br s, 1H), 11.21 (s, 1H), 6.61 (s, 1H), 6.54 (s, 1H), 6.02 (s, 1H), 5.76 (d, 1H), 4.87 (q, 1H), 3.77 (m, 1H), 3.62 (t, 2H), 3.16 (m, 1H), 2.81-2.72 (m, 2H), 2.23 (s, 3H), 1.94 (m, 2H), 1.68 (m, 2H), 1.55 (m, 3H) | | | | | |
| 93 | carboxyl | R | 1 | methyl | H | THP-4-yl |
| | (500 MHz, $CDCl_3$); δ 11.85 (br s, 1H), 6.97 (d, 1H), 6.76 (s, 1H), 6.26 (s, 1H), 5.32 (m, 1H), 3.99 (m, 2H), 3.71 (m, 1H), 3.65 (m, 1H), 3.54 (m, 2H), 3.23 (m, 1H), 2.76 (m, 1H), 2.64 (m, 1H), 2.31 (s, 3H), 2.06 (m, 2H), 1.58 (m, 2H) | | | | | |
| 94 | carboxyl | R | 1 | 4-(methane-sulfonyl) phenoxy | H | c-Pen |
| | (500MHz, DMSO-d6); δ 11.71 (br s, 1H), 7.81 (d, 2H), 7.05 (m, 2H), 6.65 (s, 1H), 6.49 (s, 1H), 6.35 (m, 1H), 5.96 (s, 1H), 4.86 (m, 1H), 3.75 (m, 1H), 3.52 (m, 1H), 3.17 (m, 1H), 3.12 (s, 3H), 1.87 (m, 2H), 1.67 (m, 2H), 1.53 (m, 4H) | | | | | |
| 95 | $MeO_2C$— | R | 1 | phenoxymethyl | H | c-Pen |
| | (500 MHz, $CDCl_3$); δ 9.49 (br s, 1H), 7.27 (m, 2H), 7.10 (s, 1H), 7.01 (m, 2H), 6.93 (m, 1H), 6.89 (s, 1H), 6.59 (s, 1H), 5.07 (s, 2H), 5.02 (m, 1H), 3.93 (m, 1H), 3.71 (s, 3H), 3.65 (m, 1H), 3.21 (m, 1H), 2.88 (m, 1H), 2.68 (m, 1H), 2.04 (m, 2H), 1.75 (m, 2H), 1 58 (m, 4H) | | | | | |
| 96 | $MeO_2C$— | R | 1 | phenyl-aminomethyl | H | c-Pen |
| | (500 MHz, $CDCl_3$); δ 9.47 (br s, 1H), 7.21 (dd, 2H), 7.07 (s, 1H), 6.88 (s, 1H), 6.75 (m, 3H), 6.57 (s, 1H), 5.08 (m, 1H), 4.35 (s, 2H), 3.94 (m, 1H), 3.72 (s, 3H), 3.68 (m, 1H), 3.23 (m, 1H), 2.92 (m, 1H), 2.10~1.30 (m, 8H) | | | | | |
| 97 | $MeO_2C$— | R | 1 | methanesulfonyl-methyl | H | c-Pen |
| | (500 MHz, $CDCl_3$); δ 10.22 (br s, 1H), 7.00 (s, 1H), 6.87 (s, 1H), 6.50 (s, 1H), 5.05 (m, 1H), 4.27 (s, 2H), 3.87 (m, 1H), 3.61 (s, 3H), 3.22 (m, 1H), 2.83 (m, 1H), 2.72 (s, 3H) 2.66 (m, 1H), 2.03 (m, 2H), 1.64 (m, 4H), 1.46 (m, 2H) | | | | | |
| 98 | carboxyl | R | 1 | methanesulfonyl-methyl | H | c-Pen |

-continued

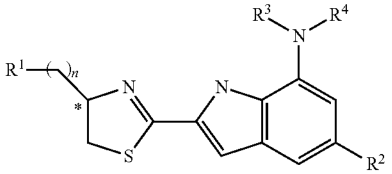

| Example | $R^1$ | * | n | $R^2$ | $R^3$ | $R^4$ | $H^1$ NMR data |
|---|---|---|---|---|---|---|---|
| | | | | | | | (400 MHz, DMSO-$d_6$); δ 11.68 (br s, 1H), 6.85 (s, 1H), 6.71 (s, 1H), 6.33 (s, 1H), 6.18 (m, 1H), 4.88 (m, 1H), 4.35 (s, 2H), 3.84 (m, 1H), 3.56 (m, 1H), 3.20 (m, 1H), 2.84 (s, 3H), 2.55 (m, 1H), 2.09 (m, 1H), 1.97 (m, 2H), 1.73 (m, 2H), 1.58 (m, 4H) |
| 99 | HO— | R | 2 | methanesulfonyl-methyl | H | c-Pen | (500 MHz, $CDCl_3$); δ 10.41 (br s, 1H), 6.98 (s, 1H), 6.90 (s, 1H), 6.49 (s, 1H), 4.68 (m, 1H), 4.28 (s, 2H), 3.96 (m, 3H), 3.59 (m, 1H), 3.13 (m, 1H), 2.05 (m, 4H), 1.72 (m, 2H), 1.60 (m, 4H) |
| 100 | EtNHC(O)— | R | 1 | H | H | c-Pen | (400 MHz, $CDCl_3$), δ 9.66, 7.08-6.99 (m, 2H), 6.92 (d, 1H), 6.55 (d, J = 7.2 Hz, 1H), 5.88 (m, 1H), 5.02 (m, 1H), 4.13 (m, 1H), 3.61 (m, 1H), 3.32~3.18 (m, 3H), 2.67 (1H, m), 2.52 (m, 1H), 2.04 (m, 1H), 1.72~1.53 (m, 6H), 1.08 (m, 3H) |
| 101 | carboxyl | R | 2 | chloro | H | c-Pen | (400 MHz, DMSO-$d_6$, Na salt); δ 11.69 (br s, 1H), 6.82 (d, J = 4.0 Hz, 1H), 6.68 (s, 1H), 6.27 (s, 1H), 6.18 (s, 1H), 4.63 (m, 1H), 3.83 (m, 1H), 3.50 (m, 1H), 3.13 (m, 1H), 2.08~1.96 (m, 6H), 1.72 (m, 2H), 1.58 (m, 4H) |
| 102 | HO— | R | 3 | chloro | H | c-Pen | (400 MHz, $CDCl_3$); δ 10.42 (br s, 1H), 6.94 (s, 1H), 6.82 (s, 1H), 6.37 (s, 1H), 4.58 (m, 1H), 4.56 (m, 1H), 3.75 (m, 2H), 3.65 (m, 1H), 1.95 (m, 7H), 1.51 (m, 4H), 1.31 (m, 2H) |
| 103 | carboxyl | R | 2 | chloro | H | THP-4-yl | (400 MHz, DMSO-$d_6$, Na salt); δ 11.53 (br s, 1H), 6.86 (s, 1H), 6.76 (s, 1H), 6.34 (s, 1H), 4.67 (m, 1H), 3.91 (m, 2H), 3.49 (m, 4H), 3.21 (m, 1H), 2.50 (m, 2H), 2.01 (m, 4H), 1.43 (m, 2H) |
| 104 | HO— | R | 3 | chloro | H | THP-4-yl | (400 MHz, $CDCl_3$); δ 11.00 (br s, 1H), 6.93 (s, 1H), 6.82 (s, 1H), 6.31 (s, 1H), 4.89 (br s, 1H), 4.56 (m, 1H), 3.95 (m, 1H), 3.85 (m, 1H), 3.77 (m, 1H), 3.65 (m, 1H), 3.51 (m, 4H), 3.10 (m, 1H), 1.97 (m, 2H), 1.83 (m, 3H), 1.74 (m, 1H), 1.44 (m, 1H), 1.40 (m, 1H) |
| 105 | $EtO_2C$— | R | 2 | methyl | H | c-Pen | (400 MHz, $CDCl_3$); δ 10.75 (br s, 1H), 6.82 (d, 2H), 6.32 (s, 1H), 4.71 (m, 1H), 4.01 (q, 2H), 3.83 (m, 1H), 3.53 (m, 1H), 3.11 (m, 1H), 2.44 (m, 2H), 2.37 (s, 3H), 2.01 (m, 4H), 1.64 (m, 4H), 1.40 (m, 2H) |
| 106 | carboxyl | R | 2 | methyl | H | c-Pen | (400 MHz, $CDCl_3$); δ 11.34 (br s, 1H), 6.56 (s, 1H), 6.54 (s, 1H), 6.06 (s, 1H), 5.05 (br d, 1H), 4.60 (m, 1H), 3.81 (m, 1H), 3.45 (m, 1H), 3.06 (m, 1H), 2.28 (s, 3H), 2.09~1.93 (m, 5H), 1.78~1.54 (m, 7H) |
| 107 | carboxyl | R | 2 | phenoxy | H | c-Pen | (400 MHz, DMSO-$d_6$); δ 11.59 (br s, 1H), 7.29 (m, 2H), 7.01 (m, 1H), 6.92 (m, 2H), 6.67 (s, 1H), 6.40 (d, 1H), 6.21 (d, 1H), 5.99 (d, 1H), 4.63 (m, 1H), 3.75 (m, 1H), 3.50 (m, 1H), 3.11 (m, 1H), 2.08 (m, 2H), 2.03 (m, 1H), 1.90 (m, 2H), 1.81 (m, 1H), 1.71 (m, 2H), 1.56 (m, 4H) |
| 108 | $EtO_2C$— | R | 2 | fluoro | H | c-Pen | (400 MHz,$CDCl_3$); δ 10.48 (br s, 1H), 6.91 (s, 1H), 6.69 (m, 1H), 6.30 (m, 1H), 4.77 (m, 1H), 4.19~4.02 (m, 3H), 3.84 (m, 1H), 3.60 (m, 1H), 3.18 (m, 1H), 2.51 (m, 2H), 2.07 (m, 4H), 1.74~1.46 (m, 6H), 1.21 (m, 3H) |
| 109 | carboxyl | R | 2 | fluoro | H | c-Pen | (400 MHz,DMSO-$d_6$); δ 11.63 (br s, 1H), 6.49 (m, 1H), 6.33 (m, 1H), 6.09 (m, 1H, 6.66 (m, 1H), 4.61 (m, 1H), 3.85 (m, 1H), 3.52 (m, 1H), 3.11 (m, 1H), 2.09~1.74 (m, 12H), |
| 110 | $EtO_2C$— | R | 2 | bromo | H | c-Pen | (400 MHz, $CDCl_3$); δ 10.02 (br s, 1H), 7.16 (s, 1H), 6.81 (s, 1H), 6.57 (s, 1H), 4.74 (m, 1H), 4.11 (m, 2H), 4.02 (m, 2H), 3.59 (q, 1H), 3.16 (q, 1H), 2.52 (m, 2H), 2.06 (m, 4H), 1.72 (m, 3H), 1.49 (m, 2H), 1.19 (t, 3H) |
| 111 | carboxyl | R | 2 | bromo | H | c-Pen | (400 MHz, DMSO-$d_6$); δ 11.77 (br s, 1H), 6.96 (s, 1H), 6.68 (s, 1H), 6.31 (m, 1H), 6.29 (s, 1H), 4.64 (m, 1H), 3.82 (m, 1H), 3.53 (m, 1H), 3.13 (m, 1H), 2.05 (m, 2H), 1.97 (m, 2H), 1.77 (m, 3H), 1.58 (m, 4H) |
| 112 | carboxyl | R | 2 | H | H | c-Pen | (400 MHz, DMSO-$d_6$); δ 11.46 (br s, 1H), 6.85 (m, 2H), 6.70 (s, 1H), 6.27 (d, J = 4.0 Hz, 1H), 5.94 (d, J = 8.0 Hz, 1H), 4.65 (m, 1H), 3.86 (m, 1H), 3.52 (m, 1H), 3.11 (m, 1H), 2.05 (m, 2H), 1.97 (m, 3H), 1.78 (m, 3H), 1.56 (m, 4H) |
| 113 | carboxyl | R | 2 | methoxy | H | c-Pen | (400 MHz, DMSO-$d_6$); δ 11.28 (br s, 1H), 6.61 (s, 1H), 6.27 (s, 1H), 5.97 (m, 1H), 5.88 (s, 1H), 4.59 (m, 1H), 3.75 (m, 1H), 3.68 (s, 3H), 3.48 (m, 2H), 3.08 (m, 1H), 2.00 (m, 5H), 1.75 (m, 3H), 1.57 (m, 4H) |

-continued

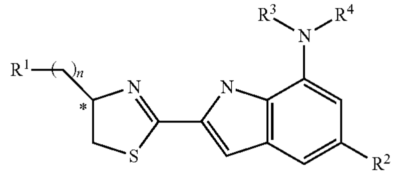

| Example | $R^1$ | * | n | $R^2$ | $R^3$ | $R^4$ |
|---|---|---|---|---|---|---|
| | | | | $H^1$ NMR data | | |
| 114 | $EtO_2C$— | R | 2 | ethoxy | H | c-Pen |
| | | | | (500 MHz, $CDCl_3$); δ 9.79 (br s, 1H), 6.80 (s, 1H), 6.44 (s, 1H), 6.19 (s, 1H), 4.69 (m, 1H), 4.11 (q, 2H), 4.03 (q, 2H), 3.83 (m, 1H), 3.54 (m, 1H), 3.11 (m, 1H), 2.49 (m, 2H), 2.02 (m, 4H), 1.69 (m, 2H), 1.60 (m, 2H), 1.48 (m, 2H), 1.25 (t, 3H), 1.19 (t, 3H) | | |
| 115 | carboxyl | R | 2 | ethoxy | H | c-Pen |
| | | | | (400 MHz, DMSO-$d_6$); δ 11.37 (br s, 1H), 6.78 (s, 1H), 6.30 (s, 1H), 5.94 (s, 1H), 4.64 (m, 1H), 3.93 (q, 2H), 3.82 (m, 1H), 3.60 (m, 1H), 3.21 (m, 1H), 2.44 (m, 2H), 1.97 (m, 4H), 1.71 (m, 2H), 1.57 (m, 4H), 1.32 (t, 3H) | | |
| 116 | $EtO_2C$— | R | 2 | $OCF_3$ | H | c-Pen |
| | | | | (500MHz, $CDCl_3$); δ 10.97 (br s, 1H), 6.93 (s, 1H), 6.86 (s, 1H), 6.30 (s, 1H), 4.76 (m, 1H), 4.05-3.89 (m, 3H), 3.78 (m, 1H), 3.57 (m, 1H), 3.16 (m, 2H), 2.42 (m, 2H), 2.00 (m, 4H), 1.63 (m, 2H), 1.45 (m, 1H), 1.34 (m, 1H) | | |
| 117 | carboxyl | R | 2 | $OCF_3$ | H | c-Pen |
| | | | | (40 MHz, DMSO-$d_6$) 11.61 (br s, 1H), 6.85 (d, 1H), 6.77 (s, 1H), 6.16 (s, 1H), 4.66 (m, 1H), 3.85 (m, 1H), 3.60 (m, 2H), 3.20 (m, 1H), 2.42 (m, 2H), 1.99 (m, 4H), 1.71 (m, 2H), 1.58 (m, 4H) | | |

Examples 118 to 123

The compounds prepared in Preparations 102 and 105 to 109 were reacted to synthesize the Example Compounds in the following table according to a method selected from Examples 1 to 7.

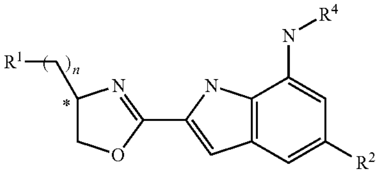

| Example | $R^1$ | * | n | $R^2$ | $R^4$ |
|---|---|---|---|---|---|
| | | | | H1 NMR data | |
| 118 | hydroxy | S | 2 | methyl | THP-4-yl |
| | | | | (400 MHz, $CDCl_3$); δ 10.11 (br s, 1H), 6.91 (s, 1H), 6.86 (s, 1H), 6.34 (s, 1H), 4.60 (t, 1H), 4.48 (m, 1H), 4.10~3.93 (m, 5H), 3.63~3.52 (m, 3H), 2.39 (s, 3H), 2.07 (d, 2H), 1.94 (m, 2H), 1.58 (m, 2H) | |
| 119 | carboxyl | S | 1 | methyl | c-Pen |
| | | | | (400 MHz, $CDCl_3$/MeOH-$d_4$); δ, 6.97 (s, 1H), 6.79 (s, 1H), 6.33 (s, 1H), 4.86 (m, 1H), 4.62 (dd, 1H), 4.35 (dd, 1H), 3.95 (m, 1H), 2.94 (dd, 1H), 2,67 (dd, 1H), 2.39 (s, 3H), 2.07 (m, 2H), 1,78 (m, 2H), 1.65 (m, 4H) | |
| 120 | carboxyl | S | 1 | methyl | THP-4-yl |
| | | | | (400 MHz, $CDCl_3$/MeOH-$d_4$); δ 6.94 (s, 1H), 6.81 (s, 1H), 6.32 (s, 1H), 4.87 (m, 1H), 4.59 (dd, 1H), 4.34 (dd, 1H), 4.02 (d, 1H), 3.68~3.58 (m, 3H), 2.92 (dd, 1H), 2.68 (dd, 1H), 2.38 (s, 3H), 2.13 (d, 2H), 1.57 (m, 2H) | |
| 121 | carboxyl | S | 1 | Cl | c-Pen |
| | | | | (400 MHz, $CDCl_3$/MeOH-$d_4$); δ 6.89 (s, 1H), 6.85 (s, 1H), 6.30 (s, 1H), 4.79 (m, 1H), 4.55 (dd, 1H), 4.30 (dd, 1H), 3.82 (m, 1H), 2.86 (dd, 1H), 2.264 (dd, 1H), 2.01 (m, 2H), 1.71 (m, 2H), 1.57 (m, 4H) | |
| 122 | carboxyl | S | 1 | Cl | (THP-4-yl)methyl |
| | | | | (400 MHz, MeOH-$d_4$); δ 6.96 (s, 1H), 6.84 (s, 1H), 6.27 (s, 1H), 4.78 (m, 1H), 4.60 (dd, 1H), 4.31 (dd, 1H), 3.94 (dd, 2H), 3.40 (m, 2H), 3.08 (d, 2H), 2.98 (dd, 2H), 2.64 (dd, 2H), 1.94 (m, 1H), 1.75 (m, 2H), 1.37 (m, 2H) | |
| | | | | (400 MHz, MeOH-$d_4$); δ 7.36-7.18 (6H, m), 6.95 (1H, s), 6.75 (1H, s), 6.27 (1H, d, J = 1.2 Hz), 3.84 (1H, brs), 3.77 (1H, brs), 3.66-3.56 (1H, m), 3.34 (1H, brs), 2.77 (2H, brs), 1.93 (2H, brs), 1.54-1.48 (6H, m) | |

-continued

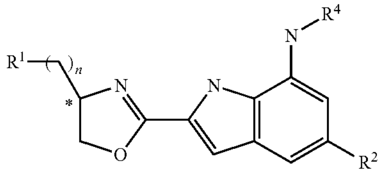

| Exam-ple | R¹ | * | n | R² | R⁴ |
|---|---|---|---|---|---|
| | | | H1 NMR data | | |
| 123 | H | — | 0 | H | THP-4-yl |
| | NMR (500 MHz, $CDCl_3$); δ 11.38 (br s, 1H), 7.10 (d, 8 Hz, 1H), 7.00~6.98 (m, 2H), 6.52 (d, J = 8.0 Hz, 1H), 4.50 (m, 2H), 4.12 (m, 2H), 4.00 (m, 2H), 3.58 (m, 1H), 3.50 (m, 2H), 2.04 (m, 2H), 1.47 (m, 2H) | | | | |

Example 124

[2-((4S,5R)-5-aminomethyl-4-benzyl-dihydro-oxazol-2-yl)-5-chloro-1H-indol-7-yl]-cyclopentyl-amine Step A: 2-[(4S,5R)-benzyl-2-(5-chloro-7-cyclopentylamino-1H-indol-2-yl)-4,5-dihydro-oxazol-5-ylmethyl]isoindol-1,3-dione 2-[(4S,5R)-benzyl-2-(5-chloro-7-nitro-1H-indol-2-yl)-4,5-dihydro-oxazol-5-ylmethyl]isoindol-1,3-dione prepared in Preparation 108 and cyclopentanone were reacted according to the same procedure as Example 1 to give the title compound.

Step B: [2-((4S,5R)-5-aminomethyl-4-benzyl-dihydro-oxazol-2-yl)-5-chloro-1H-indol-7-yl]-cyclopentyl-amine 2-[(4S,5R)-benzyl-2-(5-chloro-7-cyclopentylamino-1H-indol-2-yl)-4,5-dihydro-oxazol-5-ylmethyl]isoindol-1,3-dione (50 mg, 1 mmol) prepared in Step A was dissolved in ethanol (10 mL). Hydrazine hydrochloride (1.8 mL, 0.33 mmol) was added thereto, and the mixture was stirred for 4 h at 80° C. After completion of the reaction, the solvent was removed under reduced pressure, and the residue was purified by column chromatography to give the title compound (16 mg, Yield 39%).

$^1$H-NMR (400 MHz, MeOH-$d_4$); δ 7.36-7.18 (6H, m), 6.95 (1H, s), 6.75 (1H, s), 6.27 (1H, d, J=1.2 Hz), 3.84 (1H, brs), 3.77 (1H, brs), 3.66-3.56 (1H, m), 3.34 (1H, brs), 2.77 (2H, brs), 1.93 (2H, brs), 1.54-1.48 (6H, m)

Example 125

{2-[(R)-5-((S)-1-amino-2-phenyl-ethyl)-4,5-dihydro-oxazol-2-yl]-5-chloro-1H-indol-7-yl}-cyclopentyl-amine {(S)-1-[(R)-2-(5-chloro-7-nitro-1H-indol-2-yl)-4,5-dihydro-oxazol-5-yl]-2-phenyl-ethyl}-carbamic acid t-butyl ester prepared in Preparation 107 was reacted according to the same procedure as Example 1, and the product thus obtained (50 mg, 1 mmol) was dissolved in DCM (2 mL). TFA (2 mL) was added thereto, and the mixture was stirred for 2 h. The solvent was removed under reduced pressure, and the residue was purified column chromatography to give the title compound (38 mg, Yield 92%).

$^1$H-NMR (400 MHz, MeOH-$d_4$); δ 10.4 (1H, brs), 7.34-7.31 (2H, m), 7.27-7.20 (3H, m), 7.03 (1H, d, J=1.6 Hz), 6.95 (1H, s), 6.46 (1H, d, J=1.6 Hz), 4.65-4.59 (1H, m), 4.25-4.04 (2H, m), 3.92-3.83 (2H, m), 3.15-3.07 (1H, m), 2.90-2.85 (1H, m), 2.72-2.64 (1H, m), 2.05-2.00 (2H, m), 1.58 (2H, brs), 1.68-1.63 (4H, m), 1.49-1.47 (2H, m)

Examples 126 to 134

The compounds prepared in Preparations 110 to 117 were reacted to synthesize the Example Compounds in the following table according to a method selected from Examples 1 to 7.

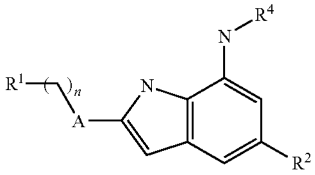

| Exam-ple | A | R¹ | n | R² | R⁴ |
|---|---|---|---|---|---|
| | | H¹ NMR data | | | |
| 126 | isoxadiazol-3-yl | 5-carboxyl | 1 | H | THP-4-yl |
| | (500 HMz, $CDCl_3$, MeOH-$d_4$); δ 7.20 (s, 1H), 6.96 (d, J = 8.0 Hz, 1H), 6.92 (t, J = 8.0 Hz, 1H), 6.42 (d, J = 7.4 Hz, 1H), 3.96 (m, 2H), 3.83 (s, 2H), 3.57 (m, 1H), 3.49 (m, 2H), 2.02 (m, 2H), 1.54 (m, 2H) | | | | |

-continued

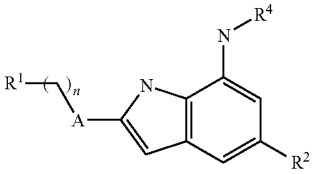

| Example | A | $R^1$ | n | $R^2$ | $R^4$ |
|---|---|---|---|---|---|
| | $H^1$ NMR data | | | | |
| 127 | isoxadiazol-3-yl | 5-hydroxy | 2 | H | THP-4-yl |
| | (400 MHz, $CDCl_3$); δ 10.40 (br s, 1H), 7.27 (s, 1H), 7.08 (d, J = 8.0 Hz, 1H), 7.04 (t, J = 8.0 Hz, 1H), 6.55 (d, J = 7.4 Hz, 1H), 4.11 (m, 4H), 3.70 (m, 1H), 3.61 (t, 2H), 3.06 (m, 2H), 2.14 (m, 2H), 1.66 (m, 2H) | | | | |
| 128 | oxadiazol-2-yl | H | 0 | methyl | c-Pen |
| | (400 MHz, $CDCl_3$); δ 9.97 (br s, 1H), 8.43 (s, 1H), 7.10 (s, 1H), 6.81 (s, 1H), 6.40 (s, 1H), 4.15 (br s, 1H), 3.94 (m, 1H), 2.42 (s, 3H), 2.04 (m, 2H), 1.73 (m, 2H), 1.63 (m, 2H), 1.54 (m, 2H) | | | | |
| 129 | thiazol-2-yl | 4-hydroxy | 1 | methyl | c-Pen |
| | (400 MHz, $CDCl_3$); δ 10.42 (br s, 1H), 7.14 (s, 1H), 6.88 (d, J = 4 Hz, 1H), 6.86 (s, 1H), 6.36 (s, 1H), 4.70 (s, 2H), 3.86 (m, 1H), 3.69 (br s, 1H), 2.39 (s, 3H), 1.95 (m, 2H), 1.37 (m, 4H), 1.26 (m, 2H) | | | | |
| 130 | thiazol-2-yl | 5-hydroxy | 1 | methyl | c-Pen |
| | (400 MHz, DMSO-$d_6$), δ 11.39 (s, 1H), 7.70 (s, 1H), 6.78 (s, 1H), 6.60 (s, 1H), 1H), 5.72 (d, J = 8 Hz, 1H), 5.62 (m, 1H), 4.72 (d, J = 4 Hz, 2H), 3.88 (m, 1H), 2.30 (s, 3H), 1.99 (m, 2H), 1.74 (m, 2H), 1.57 (m, 4H) | | | | |
| 131 | thiazol-2-yl | 4-$EtO_2C$— | 0 | methyl | c-Pen |
| | (400 MHz, $CDCl_3$); δ 9.36 (br s, 1H), 8.07 (s, 1H), 6.91 (d, J = 4 Hz, 1H), 6.84 (s, 1H), 6.37 (s, 1H), 4.37 (q, 2H), 3.95 (m, 1H), 3.64 (br s, 1H), 2.40 (s, 3H), 2.04 (m, 2H), 1.76 (m, 2H), 1.65 (m, 2H), 1.55 (m, 2H) 1.33 (t, 3H) | | | | |
| 132 | thiazol-2-yl | 4-carboxyl | 0 | methyl | c-Pen |
| | (400 MHz, DMSO-$d_6$, Na salt); δ 7.89 (s, 1H), 6.81 (s, 1H), 6.65 (br s, 1H), 6.59 (s, 1H), 6.13 (s, 1H), 3.87 (m, 1H), 2.31 (s, 3H), 2.01 (m, 2H), 1.75 (m, 4H), 1.55 (m, 2H) | | | | |
| 133 | thiazol-2-y1 | 4-hydroxyl | H | c-Pen | |
| | (400 MHz, $CDCl_3$); δ 10.60 (br s, 1H), 7.14 (s, 1H), 6.99 (m, 3H), 6.53 (d, J = 8 Hz, 1H), 4.71 (s, 2H), 3.87 (m, 1H), 3.74 (m, 1H), 1.96 (m, 2H), 1.59 (m, 4H), 1.37 (m, 2H) | | | | |
| 134 | thiazol-2-y1 | 4-$MeO_2C$— | 0 | H | c-Pen |
| | (400 MHz, $CDCl_3$); δ 9.31 (br s, 1H), 8.08 (s, 1H), 7.05 (m, 3H), 6.56 (d, j + 8 Hz, 1H), 3.96 (s, 3H), 3.73 (m, 1H), 2.07 (m, 2H), 1.80 (m, 2H), 1.67 (m, 4H) | | | | |

Example 135

{(R)-2-[5-methyl-7-(4-oxo-cyclohexylamino)-1H-indol-2-yl]-4,5-dihydro-thiazol-4-yl}acetic acid Step A: {(R)-2-[7-(1,4-dioxa-spiro[4,5]dec-8-ylamino)-5-methyl-1H-indol-2-yl]-4,5-dihydro-thiazol-4-yl}-acetic acid ethyl ester

[(R)-2-(5-methyl-7-nitro-1H-indol-2-yl)-4,5-dihydro-thiazol-4-yl]-acetic acid ethyl ester prepared in Preparation 54 and 1,4-dioxa-spiro[4,5]decan-8-one were reacted according to the same procedure as Example 1 to give the title compound.

Step B: {(R)-2-[5-methyl-7-(4-oxo-cyclohexylamino)-1H-indol-2-yl]-4,5-dihydro-thiazol-4-yl}acetic acid {(R)-2-[7-(1,4-dioxa-spiro[4,5]dec-8-yl)amino-5-methyl-1H-indol-2-yl]-4,5-dihydro-thiazol-4-yl}-acetic acid ethyl ester (177 mg, 4 mmol) prepared in Step A was dissolved in methanol (10 mL). HCl (conc. 2 mL) was added thereto, and the mixture was reacted for 6 h at 60° C. The solvent was removed under reduced pressure, and water was added to the residue. The reaction mixture was extracted with EtOAc, dried, concentrated, and purified by HPLC to give the title compound (76 mg, Yield 50%).

$^1$H-NMR (500 MHz, $CDCl_3$); δ 11.99(br s, 1H), 7.00(s, 1H), 6.79(s, 1H), 6.30(s, 1H), 5.34(m, 1H), 3.89(m, 1H), 3.71(m, 1H), 3.21(m, 1H), 2.66(m, 2H), 2.59(m, 2H), 2.43-2.35(m, 5H), 2.26(m, 2H), 1.97(m, 2H)

Example 136

2-[(R)-2-(5-chloro-7-cyclopentylamino-1H-indol-2-yl)-4,5-dihydro-thiazol-4-yl]-1-morpholin-4-yl-ethanone

[(R)-2-(5-chloro-7-cyclopentylamino-1H-indol-2-yl)-4,5-dihydro-thiazol-4-yl]-acetic acid prepared in Example 4 and morpholine were reacted according to the same procedure as Step B of Preparation 101 to give the title compound.

$^1$H-NMR (500 MHz, DMSO-$d_6$); δ 11.52(br s, 1H), 6.80(s, 1H), 6.69(s, 1H), 6.16(s, 1H), 6.12(m, 1H), 4.95(m, 1H), 3.81(m, 1H), 3.63(m, 1H), 3.41(m, 8H), 3.12(m, 1H), 2.85(m, 1H), 2.69(m, 1H), 1.93(m, 2H), 1.68(m, 2H), 1.56(m, 4H)

Examples 137 to 155

The compounds prepared in Examples 4, 11, 66, 71, 75, 81 and 101 and commercially available amines were reacted to synthesize the Example Compounds in the following table according to the same procedure as Step B of Preparation 101.

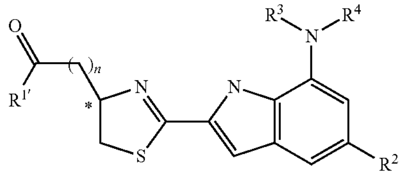

| Example | $R^{1'}$ | * | n | $R^2$ | $R^4$ | $H^1$ NMR data |
|---|---|---|---|---|---|---|
| 137 | 1-(morpholin-4-yl)ethylamino | R | 1 | chloro | c-Pen | (500 MHz, DMSO-$d_6$); δ 11.53(br s, 1H), 7.91(m, 1H), 6.80(s, 1H), 6.70(s, 1H), 6.16(s, 1H), 6.12(m, 1H), 4.93(m, 1H), 3.80(m, 1H), 3.53(m, 5H), 3.20(m, 3H), 2.60(m, 1H), 2.32(m, 7H), 1.93(m, 2H), 1.68(m, 2H), 1.53(m, 4H) |
| 138 | 1-(morpholin-4-yl)propylamino | R | 1 | chloro | c-Pen | (500 MHz, DMSO-$d_6$); δ 11.52(br s, 1H), 7.94(m, 1H), 6.79(s, 1H), 6.70(s, 1H), 6.16(s, 1H), 6.12(m, 1H), 4.93(m, 1H), 3.80(m, 1H), 3.51(m, 5H), 3.10(m, 3H), 2.59(m, 1H), 2.37(m, 1H), 2.25(m, 6H), 1.93(m, 2H), 1.68(m, 2H), 1.53(m, 6H) |
| 139 | methylamino | R | 1 | chloro | c-Pen | (500 MHz, DMSO-$d_6$); δ 11.52(br s, 1H), 7.90(m, 1H), 6.80(s, 1H), 6.69(s, 1H), 6.16(s, 1H), 6.13(m, 1H), 4.93(m, 1H), 3.80(m, 1H), 3.55(m, 1H), 3.15(m, 1H), 2.58(m, 4H), 2.39(m, 1H), 1.93(m, 2H), 1.68(m, 2H), 1.56(m, 4H) |
| 140 | dimethylamino | R | 1 | chloro | c-Pen | (500 MHz, DMSO-$d_6$); δ 11.53(br s, 1H), 6.79(s, 1H), 6.69(s, 1H), 6.16(s, 1H), 6.12(m, 1H), 4.93(m, 1H), 3.81(m, 1H), 3.63(m, 1H), 3.15(m, 1H), 2.95(s, 3H), 2.87(m, 1H), 2.83(s, 3H), 2.65(m, 1H), 1.93(m, 2H), 1.69(m, 2H), 1.53(m, 4H) |
| 141 | 4-(methyl)piperazin-1-yl | R | 1 | chloro | c-Pen | (500 MHz, DMSO-$d_6$); δ 11.52(br s, 1H), 6.80(s, 1H), 6.69(s, 1H), 6.16(s, 1H), 6.12(m, 1H), 4.94(m, 1H), 3.80(m, 1H), 3.62(m, 1H), 3.42(m, 4H), 3.35(m, 1H), 3.15(m, 1H), 2.85(m, 1H), 2.66(m, 1H), 2.24(m, 4H), 2.13(s, 3H), 1.93(m, 2H), 1.68(m, 2H), 1.55(m, 4H) |
| 142 | 3-dimethylaminopyrrolidin-1-yl | R | 1 | chloro | c-Pen | (500 MHz, DMSO-$d_6$); δ 11.53(br s, 1H), 6.80(s, 1H), 6.69(s, 1H), 6.16(s, 1H), 6.12(m, 1H), 4.94(m, 1H), 3.81(m, 1H), 3.62(m, 3H), 3.30(m, 1H), 3.17(m, 2H), 2.78(m, 1H), 2.53(m, 2H), 2.11(s, 3H), 2.07(s, 3H), 1.93(m, 2H), 1.69(m, 3H), 1.59(m, 5H) |
| 143 | piperidin-1-yl | R | 1 | chloro | c-Pen | (500 MHz, DMSO-$d_6$); δ 11.52(br s, 1H), 6.80(s, 1H), 6.69(s, 1H), 6.16(s, 1H), 6.12(m, 1H), 4.94(m, 1H), 3.81(m, 1H), 3.63(m, 1H), 3.45(m, 1H), 3.38(m, 3H), 3.14(m, 1H), 2.85(m, 1H), 1.93(m, 2H), 1.68(m, 2H), 1.48(m, 10H) |
| 144 | methylamino | R | 1 | chloro | THP-4-yl | (500 MHz, DMSO-$d_6$); δ 11.54(br s, 1H), 7.91(m, 1H), 6.81(s, 1H), 6.70(s, 1H), 6.28(s, 1H), 6.08(m, 1H), 4.93(m, 1H), 3.85(m, 2H), 3.56(m, 2H), 3.44(m, 2H), 3.15(m, 1H), 2.06(m, 4H), 2.37(m, 1H), 1.93(m, 2H), 1.39(m, 2H) |
| 145 | morpholin-4-yl | R | 1 | chloro | THP-4-yl | (500 MHz, DMSO-$d_6$); δ 11.53(br s, 1H), 6.81(s, 1H), 6.70(s, 1H), 6.28(s, 1H), 6.08(m, 1H), 4.96(m, 1H), 3.86(m, 2H), 3.47(m, 12H), 3.15(m, 1H), 2.85(m, 1H), 2.69(m, 1H), 1.94(m, 2H), 1.39(m, 2H) |
| 146 | 4-(methyl)piperazin-1-yl | R | 1 | fluoro | c-Pen | (400 MHz, DMSO-$d_6$); δ 11.44(br s, 1H), 6.73(s, 1H), 6.52(dd, 1H), 6.19(d, J = 1.2 Hz, 1H), 6.07(dd, 1H), 4.99(m, 1H), 3.84(m, 2H), 3.65(m, 1H), 3.49(m, 4H), 3.20(m, 1H), 2.88(m, 1H), 2.71(m, 1H), 2.28(m, 4H), 2.17(s, 3H), 1.98(m, 2H), 1.72(m, 2H), 1.58(m, 4H) |
| 147 | (morpholin-4-yl)ethylamino | R | 1 | fluoro | c-Pen | (400 MHz, DMSO-$d_6$); δ 11.46(br s, 1H), 7.95(m, 1H), 6.75(s, 1H), 6.73(dd, 1H), 6.18(d, J = 4.0 Hz, 1H), 6.07(dd, 1H), 5.00(m, 1H), 3.84(m, 1H), 3.58(m, 1H), 3.53(m, 4H), 3.20(m, 3H), 2.73(m, 1H), 2.45(m, 3H), 2.34(m, 4H), 1.98(m, 2H), 1.72(m, 2H), 1.59(m, 4H) |
| 148 | methylamino | R | 1 | methoxy | c-Pen | (500 MHz, DMSO-$d_6$); δ 11.22(br s, 1H), 7.90(m, 1H), 6.61(s, 1H), 6.23(s, 1H), 5.87(m, 1H), 5.85(s, 1H), 4.90(m, 1H), 3.76(m, 1H), 3.64(s, 3H), 3.52(m, 1H), 3.12(m, 1H), 2.58(m, 4H), 2.35(m, 1H), 1.91(m, 2H), 1.67(m, 2H), 1.53(m, 4H) |
| 149 | morpholin-4-yl | R | 1 | methoxy | c-Pen | (500 MHz, DMSO-$d_6$); δ 11.21(br s, 1H), 6.62(s, 1H), 6.24(s, 1H), 5.87(m, 1H), 5.85(s, 1H), 4.92(m, 1H), 3.77(m, 1H), 3.65(s, 3H), 3.60(m, 1H), 3.58-3.33(m, 8H), 3.13(m, 1H), 2.84(m, 1H), 2.66(m, 1H), 1.91(m, 2H), 1.67(m, 2H), 1.53(m, 4H) |
| 150 | methylamino | R | 1 | H | c-Pen | (500 MHz, DMSO-$d_6$); δ 11.33(br s, 1H), 7.90(m, 1H), 6.78(m, 1H), 6.71(s, 1H), 6.24(s, 1H), 5.80(m, 1H), 4.93(m, 1H), 3.81(m, 1H), 3.54(m, 1H), 3.14(m, 1H), 2.62(m, 1H), 2.58(m, 3H), 2.38(m, 1H), 1.93(m, 2H), 1.69(m, 2H), 1.54(m, 4H) |
| 151 | morpholin-4-yl | R | 1 | H | c-Pen | (500 MHz, DMSO-$d_6$); δ 11.32(br s, 1H), 6.78(m, 1H), 6.71(s, 1H), 6.24(s, 1H), 5.81(m, 1H), 4.95(m, 1H), 3.81(m, 1H), 3.61(m, 1H), 3.59-3.39(m, 8H), 3.15(m, 1H), 2.87(m, 1H), 2.68(m, 1H), 1.93(m, 2H), 1.68(m, 2H), 1.54(m, 4H) |
| 152 | methylamino | R | 1 | H | THP-4-yl | (500 MHz, DMSO-$d_6$); δ 11.34(br s, 1H), 7.90(m, 1H), 6.79(m, 1H), 6.72(s, 1H), 6.33(m, 1H), 5.76(m, 1H), 4.93(m, 1H), 3.86(m, 1H), 3.54(m, 2H), 3.43(m, 2H), 3.14(m, 1H), 2.61(m, 1H), 2.59(m, 3H), 2.38(m, 1H), 1.95(m, 2H), 1.40(m, 2H) |

-continued

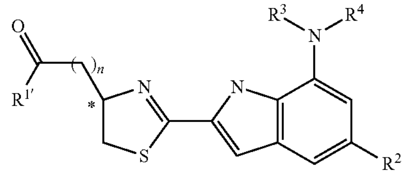

| Example | $R^{1'}$ | * | n | $R^2$ | $R^4$ |
|---|---|---|---|---|---|
| | $H^1$ NMR data | | | | |
| 153 | morpholin-4-yl | R | 1 | H | THP-4-yl |
| | (500 MHz, DMSO-$d_6$); δ 11.34(br s, 1H), 6.79(m, 1H), 6.72(s, 1H), 6.33(m, 1H), 5.77(m, 1H), 4.95(m, 1H), 3.87(m, 1H), 3.61(m, 1H), 3.57-3.38(m, 11H), 3.15(m, 1H), 2.87(m, 1H), 2.68(m, 1H), 1.95(m, 2H), 1.40(m, 2H) | | | | |
| 154 | (morpholin-4-yl)ethylamino | R | 2 | chloro | c-Pen |
| | (400 MHz, $CDCl_3$); δ 11.13(br s, 1H), 7.06(br s, 1H), 6.93(s, 1H), 6.82(s, 1H), 6.39(s, 1H), 4.61(m, 1H), 3.88(m, 2H), 3.77(s, 4H), 3.45(m, 2H), 3.07(m, 1H), 2.70(m, 6H), 2.44(m, 2H), 2.10(m, 3H), 1.95(m, 1H), 1.71(m, 2H), 1.64(m, 2H), 1.54(m, 2H) | | | | |
| 155 | 4-(methyl)piperazin-1-yl | R | 2 | chloro | c-Pen |
| | (400 MHz, $CDCl_3$); δ 10.33(br s, 1H), 6.97(s, 1H), 6.81(s, 1H), 6.42(s, 1H), 4.64(m, 1H), 3.85(m, 1H), 3.65(m, 2H), 3.56(m, 1H), 3.45(m, 2H), 3.13(m, 1H), 2.43(m, 6H), 2.04(m, 2H), 1.72(m, 8H), 1.54(m, 2H) | | | | |

Example 156

Cyclopentyl-{5-methanesulfonylmethyl-2-[(R)-4-(2-morpholin-4-yl-ethyl)-4,5-dihydro-thiazol-2-yl]-1H-indol-7-yl}-amine Step A: Cyclopentyl-{2-[(R)-4-(2-iodo-ethyl)-4,5-dihydro-thiazol-2-yl]-5-methanesulfonylmethyl-1H-indol-7-yl}-amine 2-[(R)-2-(7-cyclopentylamino-5-methanesulfonylmethyl-1H-indol-2-yl)-4,5-dihydro-thiazol-4-yl]-ethanol (178 mg, 0.42 mmol) prepared in Example 99 was dissolved in tetrahydrofuran (10 mL). Iodine (161 mg, 0.63 mmol), triphenylphosphine (166 mg, 0.63 mmol) and imidazole (86 mg, 1.23 mmol) were added thereto, and the mixture was stirred for 8 h at room temperature. The reaction was quenched by water, and the reaction mixture was extracted with ethyl acetate. The extract was washed with saturated aqueous sodium chloride solution, dried over anhydrous magnesium sulfate, and filtered. The solvent was removed under reduced pressure, and the residue was purified by column chromatography to give the title compound (120 mg, Yield 54%).

Step B: Cyclopentyl-{5-methanesulfonylmethyl-2-[(R)-4-(2-morpholin-4-yl-ethyl)-4,5-dihydro-thiazol-2-yl]-1H-indol-7-yl}-amine Cyclopentyl-{2-[(R)-4-(2-iodo-ethyl)-4,5-dihydro-thiazol-2-yl]-5-methanesulfonylmethyl-1H-indol-7-yl}-amine (116 mg, 0.22 mmol) prepared in Step A was dissolved in N,N-dimethylformamide (4 mL). Morpholine (57 mg, 0.66 mmol) was added thereto, and the mixture was stirred for 8 h at room temperature. The reaction was quenched by water, and the reaction mixture was extracted with ethyl acetate. The extract was dried over anhydrous magnesium sulfate. The solvent was removed under reduced pressure, and the residue was purified by column chromatography to give the title compound (68 mg, Yield 64%).

$^1$H-NMR (500 HMz, $CDCl_3$); δ 10.60(br s, 1H), 6.99(s, 1H), 6.89(s, 1H), 6.49(s, 1H), 4.79(m, 1H), 4.26(s, 2H), 3.86 (m, 1H), 3.57(m, 5H), 3.19(m, 1H), 2.72(s, 3H), 2.45(m, 2H), 2.32(m, 2H), 2.26(m, 2H), 2.04(m, 2H), 1.80(m, 2H), 1.66(m, 4H), 1.41(m, 2H)

Example 157

1-(4-{2-[(R)-2-(7-cyclopentylamino-5-methanesulfonylmethyl-1H-indol-2-yl)-4,5-dihydro-thiazol-4-yl]-ethyl}-piperazin-1-yl)-ethanone Cyclopentyl-{2-[(R)-4-(2-iodo-ethyl)-4,5-dihydro-thiazol-2-yl]-5-methanesulfonylmethyl-1H-indol-7-yl}-amine prepared in Step A of Example 156 and acetylpiperazine were reacted according to the same procedure as Step B of Example 156 to give the title compound.

$^1$H-NMR (500 HMz, $CDCl_3$); δ 10.62(br s, 1H), 6.99(s, 1H), 6.89(s, 1H), 6.46(s, 1H), 4.77(m, 1H), 4.26(s, 2H), 3.87 (m, 1H), 3.57(m, 1H), 3.30(m, 2H), 3.16(m, 1H), 2.72(s, 3H), 2.46(m, 2H), 2.31(m, 2H), 2.21(m, 2H), 2.04(s, 3H), 2.03(m, 2H), 1.79(m, 2H), 1.64(m, 4H), 1.45(m, 2H)

Example 158

Cyclopentyl-[2-((R)-4-pyrrolidin-1-ylmethyl-4,5-dihydro-thiazol-2-yl)-1H-indol-7-yl]-amine

[(R)-2-(7-cyclopentylamino-1H-indol-2-yl)-4,5-dihydro-thiazol-4-yl]-methanol prepared in Example 2 and pyrrolidine were reacted according to the same procedure as Example 156 to give the title compound.

$^1$H-NMR (400 HMz, DMSO-$d_6$); δ 11.37(br s, 1H), 6.83 (m, 1H), 6.75(d, J=2.0 Hz, 1H), 6.29(d, J=8.0 Hz, 1H), 5.86 (d, J=8.0 Hz, 1H), 4.80(m, 1H), 3.87(m, 1H), 3.52(m, 1H), 3.43(m, 1H), 3.33(m, 2H), 2.78(m, 2H), 2.61(m, 2H), 1.99(m, 2H), 1.72(m, 6H), 1.60(m, 4H)

Example 159

{5-Chloro-2-[(R)-4-(2-dimethylamino-ethyl)-4,5-dihydro-thiazol-2-yl]-1H-indol-7-yl}-cyclopentyl-amine 2-[(R)-2-(5-chloro-7-cyclopentylamino-1H-indol-2-yl)-4,5-dihydro-thiazol-4-yl]-ethanol prepared in Example 5 and dimethylamine were reacted according to the same procedure as Example 156 to give the title compound.

$^1$H-NMR (500 HMz, $CDCl_3$); δ 10.07(br s, 1H), 6.99(s, 1H), 6.80(s, 1H), 6.42(s, 1H), 4.67(m, 1H), 3.54(m, 1H), 3.16(m, 1H), 2.46(m, 1H), 2.37(m, 1H), 2.19(s, 6H), 2.02(m, 3H), 1.81(m, 4H), 1.69(m, 4H)

Example 160

{5-Chloro-2-[(R)-4-(2-piperazin-1-yl-ethyl)-4,5-dihydro-thiazol-2-yl]-1H-indol-7-yl}-cyclopentyl-amine Step A: {5-Chloro-2-[(R)-4-(2-1-BOC-piperazin-4-yl-ethyl)-4,5-dihydro-thiazol-2-yl]-1H-indol-7-yl}-cyclopentyl-amine 2-[(R)-2-(5-chloro-7-cyclopentylamino-1H-indol-2-yl)-4,5-dihydro-thiazol-4-yl]-ethanol prepared in Example 5 and 1-BOC-piperazine were reacted according to the same procedure as Example 156 to give the title compound.

Step B: {5-Chloro-2-[(R)-4-(2-piperazin-1-yl-ethyl)-4,5-dihydro-thiazol-2-yl]-1H-indol-7-yl}-cyclopentyl-amine {5-Chloro-2-[(R)-4-(2-1-BOC-piperazin-4-yl-ethyl)-4,5-dihydro-thiazol-2-yl]-1H-indol-7-yl}-cyclopentyl-amine prepared in Step A was dissolved in dichloromethane (50 mL). 4N hydrochloric acid ethyl acetate solution (1.3 mL, 5.28 mmol) was added thereto, and the mixture was stirred for 4 h at room temperature. After completion of the reaction, the solvent was removed under reduced pressure. The residue was recrystallized from DCM and ethylether to give the title compound (125 mg, Yield 55%).

$^1$H NMR (DMSO-$d_6$, ppm); δ 11.48(1H, s), 6.79(1H, s), 6.67(1H, s), 6.11(1H, s), 6.10(1H, d), 4.61(1H, m), 3.80(1H, m), 3.54(1H, m), 3.15(1H, m), 2.93(2H, m), 2.50-2.41(2H, m), 2.31(3H, m), 1.95(4H, m), 1.79(1H, m), 1.68(3H, m), 1.57-1.50(4H, m), 1.20(1H, m)

FAB MS (m/e)=432

Example 161

(5-Chloro-2-{(R)-4-[2-(4-ethanesulfonyl-piperazin-1-yl)-ethyl]-4,5-dihydro-thiazol-2-yl}-1H-indol-7-yl)-cyclopentyl-amine {5-Chloro-2-[(R)-4-(2-piperazin-1-yl-ethyl)-4,5-dihydro-thiazol-2-yl]-1H-indol-7-yl}-cyclopentyl-amine prepared in Example 160 and ethyl sulfonylchloride were reacted according to the same procedure as Step B of Preparation 29 to give the title compound.

$^1$H-NMR (500 HMz, $CDCl_3$); δ 11.29(br s, 1H), 6.97(s, 1H), 6.86(s, 1H), 6.37(s, 1H), 4.93(m, 1H), 3.92(br s, 1H), 3.77(m, 1H), 3.57(m, 1H), 3.16(m, 1H), 2.95(m, 2H), 2.80(m, 4H), 2.42-2.28(m, 4H), 2.03(m, 4H), 1.74(m, 3H), 1.63(m, 4H), 1.43(m, 1H), 1.32(t, 3H)

Example 162

1-(4-{2-[(R)-2-(5-chloro-7-cyclopentylamino-1H-indol-2-yl)-4,5-dihydro-thiazol-4-yl]ethyl}-piperazin-1-yl)-2-hydroxy-ethanone {5-Chloro-2-[(R)-4-(2-piperazin-1-yl-ethyl)-4,5-dihydro-thiazol-2-yl]-1H-indol-7-yl}-cyclopentyl-amine prepared in Example 160 and glycolic acid were reacted according to the same procedure as Step B of Preparation 101 to give the title compound.

$^1$H-NMR (500 HMz, DMSO-$d_6$); δ 11.47(br s, 1H), 6.79(s, 1H), 6.68(s, 1H), 6.16(s, 1H), 6.10(m, 1H), 4.63(m, 1H), 4.50(m, 1H), 4.04(m, 2H), 3.81(m, 1H), 3.55(m, 1H), 3.43(m, 2H), 3.16(m, 1H), 2.52(m, 2H), 2.35(m, 4H), 1.95(m, 3H), 1.81(m, 1H), 1.68(m, 2H), 1.53(m, 4H)

Example 163

{5-Chloro-2-[(R)-4-(2-pyrazol-1-yl-ethyl)-4,5-dihydro-thiazol-2-yl]-1H-indol-7-yl}-cyclopentyl-amine 2-[(R)-2-(5-chloro-7-cyclopentylamino-1H-indol-2-yl)-4,5-dihydro-thiazol-4-yl]-ethanol (81 mg, 0.11 mmol) prepared in Example 5 was dissolved in tetrahydrofuran (4 mL). Iodine (13.2 mg, 0.11 mmol) and imidazole (9.7 mg, 0.14 mmol) were added thereto, and the mixture was stirred for 2 h at room temperature. After completion of the reaction, the reaction mixture was filtered to remove solid moiety. The solvent was removed under reduced pressure, and tetrahydrofuran (4 mL) was added to the residue. Pyrazole (58 mg, 0.85 mmol) and sodium hydride (60% mineral oil, 21 mg, 0.85 mmol) were added thereto, and the mixture was stirred for 8 h at room temperature. The reaction was quenched by water, and the reaction mixture was extracted with ethyl acetate, dried over anhydrous magnesium sulfate, and filtered. The solvent was removed under reduced pressure, and the residue was purified by column chromatography to give the title compound (24 mg, Yield 34%).

$^1$H NMR (DMSO-$d_6$, ppm); δ 11.50(1H, s), 7.76(1H, s), 7.42(1H, s), 6.80(1H, s), 6.70(1H, s), 6.22(1H, s), 6.17(1H, s), 6.11(1H, d), 4.49(1H, quin), 4.32(2H, m), 3.80(1H, m), 3.53 (1H, t), 3.12(1H, t), 2.38(1H, m), 2.14(1H, m), 1.92(2H, m), 1.68(2H, m), 1.59-1.50(4H, m)

Example 164

(S)-1-{2-[(R)-2-(5-chloro-7-cyclopentylamino-1H-indol-2-yl)-4,5-dihydro-thiazol-4-yl]-ethyl}-pyrrolidine-2-carboxylic acid Step A: 2-{2-[(R)-2-(5-chloro-7-cyclopentylamino-1H-indol-2-yl)-4,5-dihydro-thiazol-4-yl]-ethyl}-pyrrolidine-2-carboxylic acid methyl ester 2-[(R)-2-(5-chloro-7-cyclopentylamino-1H-indol-2-yl)-4,5-dihydro-thiazol-4-yl]-ethanol prepared in Example 5 and (S)-pyrrolidin-2-yl-carboxylic acid methyl ester were reacted according to the same procedure as Example 156 to give the title compound.

Step B: (S)-1-{2-[(R)-2-(5-chloro-7-cyclopentylamino-1H-indol-2-yl)-4,5-dihydro-thiazol-4-yl]-ethyl}-pyrrolidine-2-carboxylic acid 2-{2-[(R)-2-(5-chloro-7-cyclopentylamino-1H-indol-2-yl)-4,5-dihydro-thiazol-4-yl]-ethyl}-pyrrolidine-2-carboxylic acid methyl ester prepared in Step A was hydrolyzed according to the same procedure as Step A of Preparation 101 to give the title compound.

$^1$H NMR ($CDCl_3$, ppm); δ 12.04(1H, s), 11.02(1H, s), 6.85(1H, s), 6.69(1H, s), 6.31(1H, s), 6.24(1H, m), 4.37(1H, m), 4.10(1H, m), 3.86(1H, m), 3.79(1H, m), 3.59(1H, m), 3.28(1H, m), 3.17(1H, m), 2.88(2H, m), 2.59(1H, m), 2.21 (1H, m), 2.06-1.59(11H, m), 1.23(1H, m)

Example 165

{5-Chloro-2-[(R)-4-(2-methanesulfonyl-ethyl)-4,5-dihydro-thiazol-2-yl]-1H-indol-7-yl}-cyclopentyl-amine 2-[(R)-2-(5-chloro-7-cyclopentylamino-1H-indol-2-yl)-4,5-dihydro-thiazol-4-yl]-ethanol (50 mg, 0.11 mmol) prepared in Example 5 was dissolved in N,N-dimethylformamide (2 mL). Sodium methanesulfonate (54 mg, 0.55 mmol) was added thereto, and the mixture was stirred for 8 h at room temperature. The reaction was quenched by water. The reaction mixture was extracted with ethyl acetate, dried over anhydrous magnesium sulfate, and filtered. The solvent was removed under reduced pressure, and the residue was purified by column chromatography to give the title compound (19 mg, Yield 45%).

$^1$H-NMR (400 HMz, $CDCl_3$); δ 10.39(br s, 1H), 7.03(s, 1H), 6.89(s, 1H), 6.48(s, 1H), 6.17(s, 1H), 4.77(m, 1H), 3.87 (m, 1H), 3.59(m, 1H), 3.29(m, 1H), 3.17(m, 2H), 2.86(s, 3H), 2.26(m, 2H), 2.10(m, 2H), 1.70(m, 4H), 1.51(m, 2H)

Example 166

3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid ethyl ester 2-[(R)-2-(5-chloro-7-cyclopentylamino-1H-indol-2-yl)-4,5-dihydro-thiazol-4-yl]-ethanol prepared in Example 5 and 5-methyl-3H-imidazole-4-carboxylic acid ethyl ester were reacted according to the same procedure as Example 156 to give the title compound.

$^1$H-NMR (500 HMz, DMSO-$d_6$); δ 11.49(br s, 1H), 7.71(s, 1H), 6.80(s, 1H), 6.72(s, 1H), 6.17(s, 1H), 6.08(m, 1H), 4.56 (m, 1H), 4.16(m, 4H), 3.81(m, 1H), 3.58(m, 1H), 3.18(m, 1H), 2.46(s, 3H), 2.11(m, 2H), 1.95(m, 2H), 1.68(m, 2H), 1.53(m, 4H), 1.22(m, 3H)

Example 167

3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid 3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid ethyl ester prepared in Example 166 was reacted according to the same procedure as Step A of Preparation 101 to give the title compound.

$^1$H NMR (DMSO-$d_6$, ppm); δ 11.50(1H, s), 7.71(1H, s), 6.80(1H, s), 6.72(1H, s), 6.17(1H, s), 6.08(1H, m), 4.55(1H, m), 4.13(2H, m), 3.80(1H, m), 3.55(2H, m), 2.19-2.15(2H, m), 1.95(3H, m), 1.68(3H, m), 1.51(5H, m)

Example 168

1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid Step A: 1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid ethyl ester 2-{2-[(R)-5-chloro-7-(tetrahydropyran-4-yl)amino-1H-indol-2-yl]-4,5-dihydro-thiazol-4-yl}-ethanol prepared in Example 67 and piperidine-3-carboxylic acid ethyl ester were reacted according to the same procedure as Example 156 to give the title compound.

$^1$H NMR (DMSO-$d_6$, ppm); δ 11.48(1H, s), 6.82(1H, s), 6.67(1H, s), 6.29(1H, s), 6.04(1H, d), 4.61(1H, quin), 4.47 (1H, m), 3.87(2H, m), 3.62(2H, q), 3.56(2H, m), 3.44-3.39 (4H, m), 3.14(2H, m), 2.52(1H, m), 2.37-2.30(6H, m), 1.96-1.92(3H, m), 1.81(1H, m), 1.42(2H, m), 1.28(3H, t)

Step B: 1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid 1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid ethyl ester prepared in Step A was reacted according to the same procedure as Step A of Preparation 101 to give the title compound.

$^1$H NMR (DMSO-$d_6$, ppm); δ 13.17(1H, s), 11.94(1H, s), 6.80(1H, s), 6.68(1H, s), 6.28(1H, s), 6.04(1H, d), 4.62(1H, quin), 4.47(1H, m), 3.87(2H, m), 3.56(2H, m), 3.44~3.39 (4H, m), 3.14(2H, m), 2.52(1H, m), 2.37~2.30(6H, m), 1.96-1.92(3H, m), 1.80(1H, m), 1.40(2H, m)

Example 169

[(S)-1-(2-{(R)-2-[5-chloro-7-(tetrahydro-pyran-4-ylamino)-1H-indol-2-yl]-4,5-dihydro-thiazol-4-yl]-ethyl)-pyrrolidin-3-yl}-carbamic acid t-butyl ester 2-{2-[(R)-5-chloro-7-(tetrahydropyran-4-yl)amino-1H-indol-2-yl]-4,5-dihydro-thiazol-4-yl}-ethanol prepared in Example 67 and (S)-3-BOC-amino-pyrrolidine were reacted according to the same procedure as Example 156 to give the title compound.

$^1$H-NMR (500 HMz, DMSO-$d_6$); δ 11.48(br s, 1H), 6.92 (m, 1H), 6.81(s, 1H), 6.68(s, 1H), 6.28(m, 1H), 6.05(m, 1H), 4.63(m, 1H), 3.86(m, 3H), 3.59(m, 1H), 3.54(m, 1H), 3.44(m, 2H), 3.14(m, 1H), 2.71-2.58(m, 2H), 2.25(m, 1H), 1.95(m, 4H), 1.75(m, 1H), 1.52(m, 1H), 1.39(m, 2H), 1.37-1.32(m, 11H)

Example 170

(2-{(R)-4-[2-((S)-3-amino-pyrrolidin-1-yl)-ethyl]-4,5-dihydro-thiazol-2-yl}-5-chloro-1H-indol-7-yl)-(tetrahydro-pyran-4-yl)-amine

[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-carbamic acid t-butyl ester (150 mg, 0.27 mmol) prepared in Example 169 was dissolved in dichloromethane (30 mL). 4N hydrochloric acid dioxane solution (0.34 mL, 1.35 mmol) was added thereto, and the mixture was stirred for 4 h at room temperature. After completion of the reaction, the solvent was removed under reduced pressure. The residue was recrystallized from DCM/ethylether to give the title compound (92 mg, Yield 75%).

$^1$H NMR (DMSO-$d_6$, ppm); δ 10.92(1H, s), 8.63(2H, s, br), 6.86(1H, s), 6.83(1H, s), 6.43(1H, s), 6.11(1H, m), 4.72(1H, m), 3.65(5H, m), 3.45(5H, m), 3.22(3H, m), 2.37(2H, m), 2.19(3H, m), 1.90(2H, m), 1.49(2H, m)

Example 171

N-[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-acetamide (2-{(R)-4-[2-((S)-3-amino-pyrrolidin-1-yl)-ethyl]-4,5-dihydro-thiazol-2-yl}-5-chloro-1H-indol-7-yl)-(tetrahydro-pyran-4-yl)-amine (85 mg, 0.19 mmol) prepared in Example 170 was dissolved in dichloromethane (10 mL). Diisopropylethylamine (0.13 mL, 0.75 mmol) and acetylchloride (0.013 mL, 0.19 mmol) were added thereto, and the mixture was stirred for 30 min at room temperature. The reaction was quenched by water, and the reaction mixture was extracted with ethyl acetate, dried over anhydrous magnesium sulfate, and filtered. The solvent was removed under reduced pressure, and the residue was purified by column chromatography to give the title compound (39 mg, Yield 42%).

$^1$H NMR (DMSO-$d_6$, ppm); δ 11.49(1H, s), 7.97(1H, s), 6.81(1H, s), 6.69(1H, s), 6.28(1H, s), 6.05(1H, d), 4.64(1H, quin), 4.12(1H, m), 3.85(2H, m), 3.53(2H, m), 3.44(2H, t), 3.34(2H, m), 3.15(1H, t), 2.72-2.60(3H, m), 2.39(1H, m), 2.05-1.87(4H, m), 1.80-1.72(4H, m), 1.53(1H, m), 1.37(2H, m)

Example 172

Cyclopentyl-{2-[(R)-4-(2-methoxy-ethyl)-4,5-dihydro-thiazol-2-yl]-1H-indol-7-yl}-amine 2-[2-(7-Cyclopentylamino-1H-indol-2-yl)-4,5-dihydro-thiazol-4-yl]-ethanol prepared in Example 77 and sodium methoxide were reacted according to the same procedure as Example 165 to give the title compound.

$^1$H-NMR (500 HMz, DMSO-$d_6$); δ 10.62(br s, 1H), 7.03(d, J=7.95 Hz, 1H), 6.99(t, 1H), 6.93(s, 1H), 6.48(d, J=7.35 Hz, 1H), 4.83(m, 1H), 3.83(m, 1H), 3.56(m, 1H), 3.46(m, 2H), 3.20(m, 4H), 2.05~1.87(m, 4H), 1.70~1.38(m, 6H)

Examples 173 to 224

The compounds prepared in Examples 2, 5, 24, 56, 67, 73, 77, 79, 99 and 102 and commercially available amines or sodium methanesulfonate were reacted to synthesize the Example Compounds in the following table according to a method selected from Examples 156 to 172.

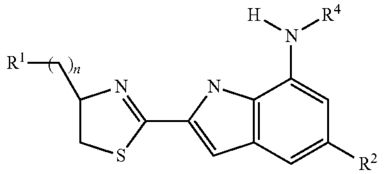

| Example | $R^1$ | * | n | $R^2$ | $R^4$ | $H^1$ NMRdata |
|---|---|---|---|---|---|---|
| 173 | amino | R | 1 | H | c-Pen | (400 MHz, DMSO-$d_6$); δ 6.92(s, 1H), 6.86(m, 2H), 6.28(d, J = 6 Hz, 1H), 5.84(m, 1H), 4.24(m, 1H), 3.86(m, 2H), 3.56(m, 1H), 2.75(m, 2H), 1.97(m, 2H), 1.72(m, 2H), 1.56(m, 4H) |
| 174 | (3R)-3-(amino)pyrrolidin-1-yl | R | 2 | chloro | c-Pen | (400 MHz, DMSO-$d_6$); δ 11.24(s, 1H), 6.62(s, 1H), 6.22(s, 1H), 5.89(d, 1H), 5.84(s, 1H), 4.83(q, 1H), 3.77(m, 1H), 3.64(s, 3H), 3.59(s, 3H), 3.56(m, 1H), 3.15(m, 1H), 2.69(m, 1H), 2.58(m, 1H), 1.90(m, 2H), 1.67(m, 2H), 1.51(m, 4H) |
| 175 | 2-oxopiperazin-4-yl | R | 2 | methoxy | c-Pen | (400 MHz, $CDCl_3$); δ 10.75(br s, 1H), 7.11(br s, 1H), 6.82(s, 1H), 6.39(d, J = 4 Hz, 1H), 6.13(d, J = 4 Hz, 1H), 4.71(m, 1H), 3.84(m, 1H), 3.81(s, 3H), 3.50(m, 1H), 3.28(m, 2H), 3.16(m, 2H), 3.08(m, 1H), 2.57(m, 4H), 2.01(m, 2H), 1.95(m, 1H), 1.84(m, 1H), 1.71(m, 2H), 1.57(m, 4H) |
| 176 | (3S)-3-(amino)pyrrolidin-1-yl | S | 2 | chloro | c-Pen | (400 MHz, MeOD); δ 7.51(s, 1H), 7.28(s, 1H), 7.06(s, 1H), 4.27(m, 1H), 4.15(m, 1H), 3.95-3.8(m, 5H), 3.67(m, 3H), 3.44(dd, 1H), 2.70(m, 1H), 2.40-2.25(m, 3H), 2.10(m, 2H), 1.91(m, 4H), 1.71(m 2H) |
| 177 | (3S)-3-(dimethylaminophenyl)ethyl aminopyrrolidin-1-yl | S | 2 | chloro | c-Pen | (500 Hz, $CDCl_3$); δ 7.16(t, 1H), 6.89(s, 1H), 6.74(s, 1H), 6.61(m, 3H), 6.34(s, 1H), 4.64(m, 1H), 3.86(m, 1H), 3.66(m, 2H), 3.51(m, 2H), 3.45-3.25(br s, 2H), 3.25-3.05(br s, 2H), 3.03(t, 1H), 3.05-2.95(br s, 1H), 2.92(s, 6H), 2.38(br s, 1H), 2.05-1.85(m, 5H), 1.80-1.65(m, 4H), 1.58(m, 1H) |
| 178 | 1-(acetyl)piperazin-4-yl | S | 2 | chloro | c-Pen | (500 Hz, $CDCl_3$); δ 10.17(br s, 1H), 7.00(s, 1H), 6.83(s, 1H), 6.43(s, 1H), 4.75(m, 1H), 3.83(m, 2H), 3.58(m, 1H), 3.56(dd, 1H), 3.48(m, 1H), 3.32(m, 1H), 3.25(m, 1H), 3.15(dd, 1H), 2.46(m, 2H), 2.36(m, 1H), 2.26(m, 2H), 2.20(m, 1H), 2.05(s, 3H), 2.04(m, 2H), 1.96(m, 1H), 1.80(m, 1H), 1.66(m, 3H), 1.48(m, 2H) |
| 179 | 1-(acetyl)piperazin-4-yl | S | 2 | chloro | H | (500 Hz, DMSO); δ 11.70(br s, 1H), 10.41(s, 1H), 7.91(s, 1H), 7.78(d, 1H), 7.58(s, 1H), 7.46(s, 2H), 7.36(m, 3H), 7.09(t, 1H), 7.05(s, 1H), 6.97(d, 2H), 3.86(s, 2H), 2.90(br s, 2H) |
| 180 | pyrrolidin-1-yl | R | 2 | methoxy | c-Pen | (500 MHz, $CDCl_3$); δ 10.11(br s, 1H), 6.82(s, 1H), 6.44(s, 1H), 6.16(s, 1H), 4.72(m, 1H), 3.81(s, 3H), 3.74(m, 1H), 3.54(dd, 1H), 3.15(dd, 1H), 2.62(m, 1H), 2.46(m, 1H), 2.42(m, 4H), 2.01(m, 4H), 1.84(m, 1H), 1.73-1.64(m, 3H), 1.58(m, 2H), 1.50(m, 1H), 1.42(m, 1H) |
| 181 | pyrrolidin-1-yl | R | 2 | H | THP-4-yl | (500 MHz, $CDCl_3$); δ 7.80-7.78 (2H, m), 7.51-7.47 (2H, m), 4.79-4.66 (4H, m), 4.39 (4H, brs), 3.73-3.55 (6H, m), 3.42-3.33 (6H, m), 3.04-2.98 (2H, m) |
| 182 | 2-oxopiperazin-4-yl | S | 2 | methyl | THP-4-yl | (500 MHz, $CDCl_3$); δ 11.05 (s, 1H), 7.72 (s, 1H), 6.82 (s, 1H), 6.78 (s, 1H), 6.27 (s, 1H), 4.71-4.67 (m, 1H), 4.03-4.01 (m, 2H), 3.62-3.47 (m, 4H), 3.30-3.20 (m, 2H), 3.15 (d, 2H), 3.11-3.08 (m, 1H), 2.59-2.53 (m, 4H), 2.42-2.36 (m, 3H), 2.09-2.04 (m, 2H), 1.95-1.92 (m, 1H), 1.84-1.81 (m, 1H), 1.59-1.51 (m, 2H) |

-continued

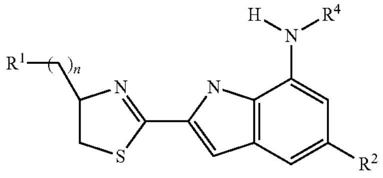

| Example | $R^1$ | * | n | $R^2$ | $R^4$ | $H^1$ NMRdata |
|---|---|---|---|---|---|---|
| 183 | 2-oxopiperazin-4-yl | R | 2 | methane sulfonyl methyl | c-Pen | (400 MHz, $CDCl_3$); δ 10.61 (brs, 1H), 6.97 (s, 1H), 6.85 (s, 1H), 6.72 (s, 1H), 6.48 (s, 1H), 4.75-4.69 (m, 2H), 4.28 (s, 2H), 3.93 (m, 1H), 3.58 (m, 1H), 3.42-3.23 (m, 3H), 3.19-3.10 (m, 2H), 2.75-2.52 (m, 6H), 2.06 (m, 2H), 1.93 (m, 2H), 1.74 (m, 2H), 1.68-1.53 (m, 6H) |
| 184 | morpholin-4-yl | S | 2 | methyl | THP-4-yl | (400 MHz, $CDCl_3$); δ 10.91(s, 1H), 6.85(s, 1H), 6.83(s, 1H), 6.28(s, 1H), 4.81(m, 1H), 3.96(m, 2H), 3.60~3.41(m, 7H), 3.17(, 1H), 2.40(m, 2H), 2.36(s, 3H), 2.29(m, 2H), 2.18(m, 2H), 2.04~1.79(m, 4H), 1.39(m, 2H) |
| 185 | 1-(acetyl)piperazin-4-yl | R | 2 | chloro | c-Pen | (500 MHz, DMSO-$d_6$); δ 11.47(br s, 1H), 6.79(s, 1H), 6.68(s, 1H), 6.16(s, 1H), 6.11(m, 1H), 4.62(m, 1H), 3.80(m, 1H), 3.55(m, 1H), 3.39(m, 4H), 3.15(m, 1H), 2.46(m, 1H), 2.32(m, 4H), 1.95(m, 4H), 1.80(m, 1H), 1.68(m, 2H), 1.53(m, 4H) |
| 186 | 4-methyl-piperazin-1-yl | R | 2 | chloro | c-Pen | (500 MHz, DMSO-$d_6$); δ 11.47(br s, 1H), 6.79(s, 1H), 6.67(s, 1H), 6.16(s, 1H), 6.10(m, 1H), 4.59(m, 1H), 3.80(m, 1H), 3.54(m, 1H), 3.15(m, 1H), 2.40(m, 10H), 2.13(s, 3H), 1.95(m, 3H), 1.78(m, 1H), 1.68(m, 2H), 1.53(m, 4H) |
| 187 | 4-(hydroxy)piperidin-1-yl | R | 2 | chloro | c-Pen | (500 MHz, DMSO-$d_6$); δ 11.48(br s, 1H), 6.79(s, 1H), 6.68(s, 1H), 6.16(s, 1H), 6.10(m, 1H), 4.60(m, 1H), 3.80(m, 1H), 3.54(m, 1H), 3.32(m, 4H), 3.16(m, 1H), 2.71(m 1H), 2.60(m, 1H), 2.32(m, 5H), 1.71(m, 5H), 1.57(m, 5H) |
| 188 | 2-oxopiperazin-4-yl | R | 2 | chloro | c-Pen | (500 MHz, DMSO-$d_6$); δ 11.48(br s, 1H), 7.71(s, 1H), 6.79(s, 1H), 6.68(s, 1H), 6.16(s, 1H), 6.10(m, 1H), 4.61(m, 1H), 3.81(m, 1H), 3.55(m, 1H), 3.13(m, 3H), 2.92(m, 2H), 2.56(m 3H), 1.96(m, 3H), 1.80(m, 1H), 1.68(m, 2H), 1.53(m, 4H) |
| 189 | piperidin-1-yl | R | 2 | chloro | c-Pen | (500 MHz, DMSO-$d_6$); δ 11.52(br s, 1H), 6.80(s, 1H), 6.70(s, 1H), 6.16(s, 1H), 6.12(m, 1H), 4.63(m, 1H), 3.80(m, 1H), 3.57(m, 1H), 3.29(m, 4H), 3.17(m, 1H), 2.60(m, 4H), 1.95(m, 3H), 1.68(m, 2H), 1.58(m, 9H) |
| 190 | 1,1-dioxo-thiomorpholin-4-yl | R | 2 | chloro | c-Pen | (500 MHz, DMSO-$d_6$); δ 11.48(br s, 1H), 6.79(s, 1H), 6.68(s, 1H), 6.16(s, 1H), 6.09(m, 1H), 4.61(m, 1H), 3.80(m, 1H), 3.56(m, 1H), 3.16(m, 1H), 3.07(m, 4H), 2.89(m, 4H), 2.67(m, 2H), 1.94(m, 3H), 1.81(m, 1H), 1.68(m, 2H), 1.53(m, 4H) |
| 191 | 2-oxopyrrolidin-1-yl | R | 2 | chloro | c-Pen | (500 MHz, DMSO-$d_6$); δ 11.49(br s, 1H), 6.80(s, 1H), 6.69(s, 1H), 6.16(s, 1H), 4.51(m, 1H), 3.80(m, 1H), 3.57(m, 1H), 3.46(m, 1H), 3.32(m, 1H), 3.15(m, 1H), 2.18(m, 2H), 1.91(m, 5H), 1.80(m, 1H), 1.68(m, 2H), 1.53(m, 4H) |
| 192 | (3S)-3-(dimethylaminocarboxy)piperidin-1-yl | R | 2 | chloro | THP-4-yl | (400 MHz, DMSO-$d_6$); δ 11.48(s, 1H), 6.81(s, 1H), 6.69(s, 1H), 6.28(s, 1H), 6.04(d, 1H), 4.60(q, 1H), 3.87(m, 2H), 3.56(m, 2H), 3.44(t, 2H), 3.16(m, 1H), 2.97(s, 3H), 2.95(m, 1H), 2.88-2.76(m, 2H), 2.74(m, 5H), 1.96(m, 4H), 1.80(m, 2H), 1.66(m, 2H), 1.50-1.37(m, 3H), 1.23(m, 1H) |
| 193 | piperazin-1-yl | R | 2 | chloro | THP-4-yl | (400 MHz, DMSO-$d_6$); δ 11.42(s, 1H), 6.83(s, 1H), 6.74(s, 1H), 6.30(s, 1H), 6.02(d, 1H), 4.69(m, 1H), 3.85(m, 1H), 3.52-3.42(m, 6H), 3.35(m, 3H), 3.20(m, 2H), 2.16(m, 2H), 1.92(m, 3H), 1.42(m, 3H) |
| 194 | 1-(hydroxymethylcarbonyl) piperazin-4-yl | R | 2 | chloro | THP-4-yl | (500 MHz, DMSO-$d_6$); δ 11.48(br s, 1H), 6.81(s, 1H), 6.69(d, J = 1.8 Hz, 1H), 6.29(s, 1H), 6.05(d, J = 7.4 Hz, 1H), 4.62(m, 1H), 4.49(t, 1H), 4.04(m, 2H), 3.87(m, 2H), 3.56(m, 1H), 3.45(m, 4H), 3.29(m, 4H), 3.16(m, 1H), 2.36(m, 4H). 1.96(m, 3H), 1.80(m, 1H), 1.40(m, 2H) |
| 195 | 1-(trifluoroacetyl)piperazin-4-yl | R | 2 | chloro | THP-4-yl | (500 MHz, DMSO-$d_6$); δ 11.47(s, 1H), 6.81(s, 1H), 6.69(s, 1H), 6.28(s, 1H), 6.09(d, 1H), 4.62(q, 1H), 3.87(m, 2H), 3.56(m, 4H), 3.47-3.38(m, 7H), 3.16(m, 1H), 2.53(m, 1H), 2.37~2.30(m, 4H), 1.94(m, 3H), 1.81(m, 1H), 1.40(m, 2H) |
| 196 | 1-[(furan-2-yl)carbonyl] piperazin-4-yl | R | 2 | chloro | THP-4-yl | (500 MHz, DMSO-$d_6$); δ 11.48(br s, 1H), 7.79(s, 1H), 6.81(s, 1H), 6.69(s, 1H), 6.59(m, 1H), 6.28(s, 1H), 6.05(m, 1H), 4.63(m, 1H), 3.86(m, 2H), 3.57(m, 6H), 3.44(m, 2H), 3.16(m, 2H), 2.56(m, 1H), 1.96(m, 3H), 1.83(m, 1H), 1.41(m, 2H) |

-continued

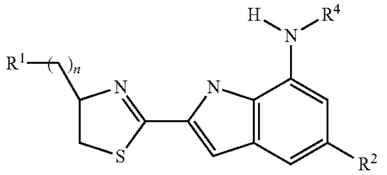

| Example | $R^1$ | * | n | $R^2$ | $R^4$ |
|---|---|---|---|---|---|
| | $H^1$ NMRdata | | | | |
| 197 | 1-(1,4-pyrazin-2-yl)piperazin-4-yl | R | 2 | chloro | THP-4-yl |
| | (500 MHz, DMSO-$d_6$); δ 11.48(br s, 1H), 8.27(s, 1H), 8.04(s, 1H), 7.80(s, 1H), 6.81(s, 1H), 6.69(s, 1H), 6.29(s, 1H), 6.05(m, 1H), 4.64(m, 1H), 3.86(m, 2H), 3.57(m, 2H), 3.53(m, 4H), 3.18(m, 1H), 2.57(m, 1H). 1.99(m, 1H), 1.95(m, 2H), 1.83(m, 1H), 1.40(m, 2H) | | | | |
| 198 | 1-(1,3-pyrazin-2-yl)piperazin-4-yl | R | 2 | chloro | THP-4-yl |
| | (500 MHz, DMSO-$d_6$); δ 11.49(br s, 1H), 8.31(m, 1H), 6.81(s, 1H), 6.69(s, 1H), 6.58(m, 1H), 6.28(s, 1H), 6.06(m, 1H), 4.65(m, 1H), 3.86(m, 2H), 3.69(m, 4H), 3.58(m, 2H), 3.45(m, 2H), 3.35(m, 1H), 3.18(m, 1H), 2.56(m, 1H). 2.43(m, 3H), 2.00(m, 1H), 1.96(m, 2H), 1.40(m, 2H) | | | | |
| 199 | amino | R | 2 | fluoro | c-Pen |
| | (400 MHz, $CDCl_3$/DMSO-$d_6$); δ 11.28(br s, 1H), 6.80(br s, 2H), 6.80(d, J = 2.0 Hz), 6.50(dd, 1H), 6.16(dd, 1H), 4.58(m, 1H), 3.81(m, 1H), 3.54(m, 1H), 3.24(m, 2H), 3.02(m, 1H), 2.13~1.55(m, 10H) | | | | |
| 200 | 1-(acetyl)piperazin-4-yl | R | 2 | fluoro | c-Pen |
| | (400 MHz, $CDCl_3$); δ 10.47(br s, 1H), 6.87(s, 1H), 6.66(d, J = 8.0 Hz, 1H), 6.26(d, J = 12.0 Hz, 1H), 4.80(m, 1H), 3.92(m, 1H), 3.81(m, 1H), 3.59(m, 2H), 3.49(m, 1H), 3.28(m, 1H), 3.18(m, 1H), 2.44(m, 2H), 2.34(m, 1H), 2.23(m, 2H), 2.14(m, 1H), 2.05(s, 3H), 1.93(m, 1H), 1.81(m, 1H), 1.71(m, 5H), 1.48(m, 2H) | | | | |
| 201 | morpholin-4-yl | R | 2 | fluoro | c-Pen |
| | (400 MHz, $CDCl_3$); δ 10.92(br s, 1H), 6.87(s, 1H), 6.64(d, J = 8.0 Hz, 1H), 6.24(d, J = 12.0 Hz, 1H), 4.83(m, 1H), 3.93(m, 1H), 3.77(m, 1H), 3.54(m, 4H), 3.47(m, 1H), 3.17(m, 1H), 2.38(m, 1H), 2.33(m, 2H), 2.16(m, 2H), 2.04(m, 3H), 1.77(m, 1H), 1.65(m, 4H), 1.47(m, 1H), 1.35(m, 1H) | | | | |
| 202 | dimethylamino | R | 2 | fluoro | c-Pen |
| | (400 MHz, $CDCl_3$); δ 10.99(br s, 1H), 6.80(s, 1H), 6.60(d, J = 8.0 Hz, 1H), 6.22(d, J = 12.0 Hz, 1H), 4.59(m, 1H), 4.13(m, 1H), 3.47(m, 1H), 3.03(m, 1H), 2.90(m, 1H), 2.55(m, 1H), 2.42(s, 6H), 2.01(m, 3H), 1.81(m, 1H), 1.62(m, 2H), 1.55(m, 4H) | | | | |
| 203 | pyrrolidin-1-yl | R | 2 | fluoro | c-Pen |
| | (400 MHz, $CDCl_3$); δ 11.39(br s, 1H), 6.81(s, 1H), 6.63(dd, 1H), 6.25(dd, 1H), 4.59(m, 1H), 4.17(m, 1H), 3.89(m, 1H), 3.32(m, 1H), 3.07(m, 3H), 2.71(m, 1H), 2.09(m, 2H), 1.95(m, 4H), 1.77(m, 2H), 1.65(m, 4H) | | | | |
| 204 | 1,1-dioxo-thiomorpholin-4-yl | R | 2 | fluoro | c-Pen |
| | (400 MHz, $CDCl_3$); δ 11.05(br s, 1H), 6.94(s, 1H), 6.60(d, J = 8.0 Hz, 1H), 6.26(d, J = 12.0 Hz, 1H), 4.74(m, 1H), 3.85(m, 1H), 3.62(t, 1H), 3.49(q, 1H), 3.18(q, 1H), 3.00(m, 8H), 2.74(m, 2H), 2.05(m, 3H), 1.79(m, 2H), 1.63(m, 4H) | | | | |
| 205 | 2-oxopiperazin-4-yl | R | 2 | fluoro | c-Pen |
| | (400 MHz, $CDCl_3$); δ 11.26(br s, 1H), 7.26(br s, 1H), 6.87(s, 1H), 6.58(d, J = 8.0 Hz, 1H), 6.22(d, J = 12.0 Hz, 1H), 4.73(m, 1H), 3.84(m, 1H), 3.53(t, 1H), 3.19(m, 5H), 2.57(m, 4H), 2.04(m, 3H), 1.95(m, 1H), 1.74(m, 2H), 1.62(m, 2H) | | | | |
| 206 | 1-(hydroxymethylcarbonyl) piperazin-4-yl | R | 2 | fluoro | c-Pen |
| | (400 MHz, $CDCl_3$); δ 11.26(br s, 1H), 6.89(s, 1H), 6.63(d, J = 8.0 Hz, 1H), 6.22(d, J = 12.0 Hz, 1H), 4.85(m, 1H), 4.10(s, 2H), 3.77(m, 1H), 3.57(m, 2H), 3.41(m, 1H), 3.14(q, 1H), 3.00(m, 1H), 2.91(m, 1H), 2.38(m, 3H), 2.12(m, 2H), 2.02(m, 4H), 1.85(m, 1H), 1.77(m, 1H), 1.63(m, 4H), 1.36(m, 1H), 1.26(m, 1H) | | | | |
| 207 | methanesulfonyl | R | 2 | fluoro | c-Pen |
| | (400 MHz, $CDCl_3$); δ 9.89(br s, 1H), 6.87(s, 1H), 6.67(dd, 1H), 6.28(dd, 1H), 4.77(m, 1H), 3.83(t, 1H), 3.59(m, 1H), 3.31(m, 1H), 3.13(m, 2H), 2.84(s, 3H), 2.27(m, 2H), 2.04(m, 2H), 1.68(m, 6H), 1.51(m, 2H) | | | | |
| 208 | dimethylamino | R | 2 | fluoro | THP-4-yl |
| | (400 MHz, $CDCl_3$); δ 11.27(br s, 1H), 6.79(s, 1H), 6.60(d, J = 8.0 Hz, 1H), 6.22(d, J = 12.0 Hz, 1H), 4.61(m, 1H), 4.13(m, 2H), 3.59(m, 4H), 3.04(m, 1H), 2.55(s, 4H), 2.04(m, 6H), 1.65(m, 2H), 1.26(m, 2H) | | | | |
| 209 | pyrrolidin-1-yl | R | 2 | fluoro | THP-4-yl |
| | (400 MHz, $CDCl_3$); δ 11.16(br s, 1H), 6.87(s, 1H), 6.68(d, J = 8.0 Hz, 1H), 6.26(d, J = 12.0 Hz, 1H), 4.69(m, 1H), 4.17(d, J = 8.0 Hz, 2H), 3.60(m, 5H), 3.17(m, 1H), 2.90(m, 1H), 2.67(m, 5H), 2.09(m, 3H), 1.90(m, 4H), 1.57(m, 2H) | | | | |
| 210 | morpholin-4-yl | R | 2 | fluoro | THP-4-yl |
| | (400 MHz, $CDCl_3$); δ 11.16(br s, 1H), 6.86(s, 1H), 6.64(d, J = 8.0 Hz, 1H), 6.23(d, J = 12.0 Hz, 1H), 4.75(m, 1H), 4.02(m, 1H), 3.66(m, 4H), 3.51(m, 4H), 3.18(m, 1H), 2.60(m, 1H), 2.49(m, 4H), 2.07(m, 4H), 1.80(m, 1H), 1.54(m, 2H) | | | | |

-continued

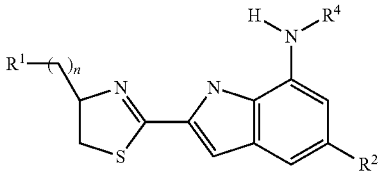

| Example | $R^1$ | * | n | $R^2$ | $R^4$ |
|---|---|---|---|---|---|
| | $H^1$ NMRdata | | | | |
| 211 | 1-(acetyl)piperazin-4-yl | R | 2 | fluoro | THP-4-yl |
| | (400 MHz, $CDCl_3$); δ 10.20(br s, 1H), 6.87(s, 1H), 6.68(d, J = 8.0 Hz, 1H), 6.27(d, J = 12.0 Hz, 1H), 4.76(m, 1H), 4.01(m, 3H), 3.61(m, 4H), 3.30(m, 2H), 3.20(m, 1H), 2.51(m, 2H), 2.33(m, 4H), 2.06(m, 7H), 1.99(m, 1H), 1.49(m, 2H) | | | | |
| 212 | 1,1-dioxo-thiomorpholin-4-yl | R | 2 | fluoro | THP-4-yl |
| | (400 MHz, $CDCl_3$); δ 6.93(s, 1H), 6.64(d, J = 8.0 Hz, 1H), 6.28(d, J = 12.0 Hz, 1H), 4.68(m, 1H), 4.03(m, 2H), 3.55(m, 3H), 3.26(m, 2H), 3.17(m, 3H), 3.05(m, 4H), 2.95(m, 1H), 2.82(m, 1H), 2.09(m, 4H), 1.82(m, 1H), 1.65(m, 2H) | | | | |
| 213 | methanesulfonyl | R | 2 | fluoro | THP-4-yl |
| | (400 MHz, $CDCl_3$); δ 10.15(br s, 1H), 6.86(s, 1H), 6.65(dd, 1H), 6.26(dd, 1H), 4.77(m, 1H), 4.05(m, 1H), 3.56(m, 4H), 3.36(m, 1H), 3.24(m, 2H), 3.12(m, 1H), 2.91(s, 3H), 2.32(m, 1H), 2.22(m, 1H), 2.13(m, 1H), 2.02(m, 1H), 1.54(m, 2H) | | | | |
| 214 | 2-oxopiperazin-4-yl | R | 2 | fluoro | THP-4-yl |
| | (400 MHz, $CDCl_3$); δ 11.07(br s, 1H), 7.70(br s, 1H), 6.83(s, 1H), 6.61(d, J = 8.0 Hz, 1H), 6.22(d, J = 12.0 Hz, 1H), 5.19(m, 1H), 4.71(m, 1H), 4.05(d, J = 12.0 Hz, 2H), 3.55(m, 4H), 3.33(m, 3H), 3.14(m, 1H), 2.73(m, 4H), 2.10(m, 2H), 1.98(m, 2H), 1.58(m, 4H) | | | | |
| 215 | 1-(hydroxymethylcarbonyl) piperazin-4-yl | R | 2 | fluoro | THP-4-yl |
| | (400 MHz, $CDCl_3$); δ 11.19(br s, 1H), 6.89(s, 1H), 6.65(d, J = 8.0 Hz, 1H), 6.23(d, J = 12.0 Hz, 1H), 4.82(m, 1H), 4.20(m, 1H), 4.18(s, 2H), 3.98(m, 2H), 3.61(m, 2H), 3.47(m, 4H), 3.16(m, 3H), 2.42(m, 3H), 2.17(m, 5H), 1.90(m, 2H), 1.40(m, 2H) | | | | |
| 216 | dimethylamino | R | 2 | H | c-Pen |
| | (500 MHz, DMSO-$d_6$); δ 10.62(br s, 1H), 7.03(d, J = 7.95 Hz, 1H), 6.99(t, 1H), 6.93(s, 1H), 6.48(d, J = 7.35 Hz, 1H), 4.83(m, 1H), 3.83(m, 1H), 3.56(m, 1H), 3.46(m, 2H), 3.20(m, 4H), 2.05~1.87(m, 4H), 1.70~1.38(m, 6H) | | | | |
| 217 | piperidin-1-yl | R | 2 | H | c-Pen |
| | (400 MHz, $CDCl_3$); δ 10.34(br s, 1H), 7.04(d, 1H), 6.99(t, 1H), 6.49(d, 1H), 4.72(m, 1H), 3.86(m, 1H), 3.51(m, 1H), 3.15(m, 1H), 2.30~2.00(m, 8H), 2.69~1.40(m, 14H) | | | | |
| 218 | methanesulfonyl | R | 2 | H | THP-4-yl |
| | (400 MHz, $CDCl_3$); δ 10.02(br s, 1H), 7.08(d, 1H), 7.00(t, 1H), 6.95(s, 1H), 6.54(d, 1H), 4.78(m, 1H), 4.01(m, 2H), 3.61-3.47(m, 4H), 3.33(m, 1H), 3.15(m, 2H), 2.85(s, 3H), 2.25(m, 2H). 2.05(m, 2H), 1.51(m, 2H) | | | | |
| 219 | 1-(hydroxymethylcarbonyl) piperazin-4-yl | R | 2 | methoxy | c-Pen |
| | (400 MHz, $CDCl_3$); δ 11.13(br s, 1H), 6.98(s, 1H), 6.42(s, 1H), 6.13(d, 1H), 4.85(m, 1H), 4.07(s, 2H), 3.81(m, 8H), 3.55(m, 2H), 3.39(m, 1H), 3.13(m, 1H), 2.96(m, 1H), 2.90(m, 1H), 2.35(m, 3H), 2.10(m, 2H), 1.99(m, 3H), 1.84(m, 1H), 1.75(m, 1H), 1.62(m, 4H), 1.44(m, 1H), 1.35(m, 1H) | | | | |
| 220 | 1-(acetyppiperazin-4-yl | R | 3 | chloro | c-Pen |
| | (400 MHz, $CDCl_3$); δ 10.33(br s, 1H), 6.97(s, 1H), 6.81(s, 1H), 6.42(s, 1H), 4.64(m, 1H), 3.85(m, 1H), 3.65(m, 2H), 3.56(m, 1H), 3.45(m, 2H), 3.13(m, 1H), 2.43(m, 6H), 2.04(m, 2H), 1.72(m, 8H), 1.54(m, 2H) | | | | |
| 221 | morpholin-4-yl | R | 1 | H | c-Pen |
| | (400 MHz, DMSO-$d_6$); δ 11.37(br s, 1H), 6.83(m, 1H), 6.75(m, 1H), 6.29(d, J = 8.0 Hz, 1H), 5.85(d, J = 8.0 Hz, 1H), 4.87(m, 1H), 3.87(m, 1H), 3.61(m, 4H), 3.35(m, 3H), 2.71(m, 1H), 2.54(m, 2H), 2.44(m, 2H), 1.99(m, 2H), 1.74(m, 6H), 1.59(m, 4H) | | | | |
| 222 | morpholin-4-yl | R | 3 | chloro | c-Pen |
| | (400 MHz, $CDCl_3$); δ 11.07(br s, 1H), 6.90(s, 1H), 6.74(s, 1H), 6.36(s, 1H), 4.61(m, 1H), 3.94(m, 4H), 3.55(m, 1H), 3.04(m, 3H), 2.04(m, 7H), 1.71(m, 3H), 1.61(m, 4H), 1.26(m, 3H) | | | | |
| 223 | dimethylamino | R | 1 | H | c-Pen |
| | (400 MHz, $CDCl_3$); δ 9.87(br, 1H), 7.05(d, J = 8.0 Hz, 1H), 6.99(t, 1H), 6.89(s, 1H), 6.52(d, J = 8.0 Hz, 1H), 4.83(m, 1H), 3.91(m, 1H), 3.50(t, 1H), 3.29(t, 1H), 2.63(m, 1H), 2.44(m, 1H), 2.29(s, 6H), 2.04(m, 2H), 1.70(m, 2H), 1.50(m, 4H) | | | | |
| 224 | morpholin-4-yl | R | 2 | chloro | c-Pen |
| | (DMSO-$d_6$, ppm); δ 11.46(1H, s), 6.79(1H, s), 6.68(1H, s), 6.11(1H, s), 6.09(1H, d), 4.61(1H, quin), 3.81(1H, m), 3.57(4H, m), 3.15(1H, m), 2.50-2.43(3H, m), 2.35(4H, m), 1.95(2H, m), 1.80(1H, m), 1.68(2H, m), 1.57-1.49(4H, m), 1.21(1H, m) | | | | |

Example 225

{5-Methyl-2-[(R)-4-(2-morpholin-4-yl-ethyl)-4,5-dihydro-oxazol-2-yl]-1H-indol-7-yl}-(tetrahydropyran-4-yl)-amine 2-[(R)-2-(5-methyl-7-nitro-1H-indol-2-yl)-4,5-dihydro-oxazol-4-yl]acetic acid prepared in Example 104, tetrahydro-pyran-4-one and morpholine were consecutively reacted according to the same procedures as Example 1, Step A of Preparation 29, and Example 156 to give the title compound.

$^1$H NMR (400 MHz, $CDCl_3$); δ 10.11(br s, 1H), 6.91(s, 1H), 6.86(s, 1H), 6.34(s, 1H), 4.60(t, 1H), 4.48(m, 1H), 4.10~3.93(m, 5H), 3.63~3.52(m, 3H), 2.39(s, 3H), 2.07(d, 2H), 1.94(m, 2H), 1.58(m, 2H)

Example 226

{5-Methyl-2-[(S)-4-(2-morpholin-4-yl-ethyl)-4,5-dihydro-thiazol-2-yl]-1H-indol-7-yl}-(tetrahydro-pyran-4-ylmethyl)-amine Step A: ((S)-2-{5-methyl-7-[(tetrahydro-pyran-4-ylmethyl)-amino]-1H-indol-2-yl}-4,5-dihydro-thiazol-4-yl)-acetic acid isopropyl ester

[(5-Methyl-7-nitro-1H-indol-2-yl)-4,5-dihydro-thiazol-4-yl]-acetic acid isopropyl ester prepared in Preparation 52 and tetrahydropyran-4-carboxyaldehyde were reacted according to the same procedure as Example 1 to give the title compound.

Step B: 2-((R)-2-{5-methyl-7-[(tetrahydro-pyran-4-ylmethyl)-amino]-1H-indol-2-yl}-4,5-dihydro-thiazol-4-yl)-ethanol ((S)-2-{5-methyl-7-[(tetrahydro-pyran-4-ylmethyl)-amino]-1H-indol-2-yl}-4,5-dihydro-thiazol-4-yl)-acetic acid isopropyl ester prepared in Step A was reacted according to the same procedure as Example 5 to give the title compound.

Step C: {5-Methyl-2-[(S)-4-(2-morpholin-4-yl-ethyl)-4,5-dihydro-thiazol-2-yl]-1H-indol-7-yl}-(tetrahydro-pyran-4-ylmethyl)-amine 2-((R)-2-{5-methyl-7-[(tetrahydro-pyran-4-ylmethyl)-amino]-1H-indol-2-yl}-4,5-dihydro-thiazol-4-yl)-ethanol prepared in Step B and morpholine were reacted according to the same procedure as Example 156 to give the title compound.

$^1$H NMR (500 MHz, $CDCl_3$); δ 11.13(s, 1H), 6.82(d, 2H), 6.24(s, 1H), 4.81-4.78(m, 1H), 3.88-3.81(m, 2H), 3.60-3.46 (m, 5H), 3.35-3.30(m, 2H), 3.19-3.17(m, 1H), 3.01(br, 2H), 2.38-2.26(m, 7H), 2.14(s, 2H), 1.91-1.88(m, 1H), 1.75-1.71 (m, 2H), 1.53~1.47(m, 2H), 1.28-1.16(m, 2H).

Examples 227 to 257

The compounds of Examples 10, 22, 51, 66 and 82 were reacted according to the same procedure as Example 226, or the compounds of Preparations 52 and 71 and commercially available aldehydes or ketones and amines were selectively reacted according to the same procedure as Example 226 to synthesize the Example Compounds in the following table.

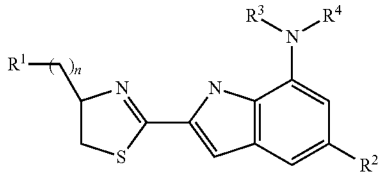

| Example | $R^1$ | * | n | $R^2$ | $R^3$ | $R^4$ |
|---|---|---|---|---|---|---|
| | $H^1$ NMR data | | | | | |
| 227 | 1-(acetyl)piperazin-4-yl | S | 2 | phenoxy | isobutyl | isobutyl |
| | (400 MHz, $CDCl_3$); δ 9.56 (1H, brs), 7.30-7.24 (2H, m), 7.04-7.00 (1H, m), 6.96-6.94 (3H, m), 6.84 (1H, d, J = 2.4 Hz), 6.63 (1H, d, J = 2.0 Hz), 4.79-4.72 (1H, m), 3.64-3.52 (3H, m), 3.45-3.34 (2H, m), 3.17-3.00 (5H, m), 2.64-2.52 (2H, m), 2.44-2.35 (1H, m), 2.08 (1H, s), 2.06-1.99 (1H, m), 1.91-1.82 (1H, m), 1.50-1.40 (2H, m), 1.38-1.26 (4H, m), 0.82-0.79 (12H, m) | | | | | |
| 228 | pyrrolidin-1-yl | S | 2 | phenoxy | isobutyl | isobutyl |
| | (400 MHz, $CDCl_3$); δ 9.24 (1H, brs), 7.31-7.27 (2H, m), 7.05-7.02 (1H, m), 6.97-6.95 (3H, m), 6.86 (1H, d, J = 2.0 Hz), 6.68 (1H, d, J = 2.0 Hz), 4.77-4.70 (1H, m), 3.63-3.58 (1H, m), 3.41-3.28 (6H, m), 3.19-3.05 (5H, m), 2.52-2.46 (1H, m), 2.26-2.20 (1H, m), 2.16-2.13 (4H, m), 1.56-1.46 (2H, m), 1.38-1.33 (4H, m), 0.85-0.83 (12H, m) | | | | | |
| 229 | 1-(hydroxymethylcarbonyl) piperazin-4-yl | S | 2 | phenoxy | H | c-Pen |
| | (400 MHz, $CDCl_3$); δ 10.7 (1H, brs), 7.30-7.27 (2H, m), 7.04-6.97 (3H, m), 6.86 (1H, s), 6.62 (1H, d, J = 2.0 Hz), 6.28 (1H, d, J = 2.5 Hz), 4.87-4.80 (1H, m), 3.80-3.75 (1H, m), 3.59-3.55 (2H, m), 3.49-3.45 (1H, m), 3.18-3.08 (2H, m), 3.03-3.01 (1H, m), 2.47-2.38 (3H, m), 2.24-2.14 (3H, m), 2.05-1.88 (4H, m), 1.84-1.55 (8H, m), 1.49-1.39 (2H, m) | | | | | |
| 230 | piperazin-1-yl | S | 2 | phenoxy | H | c-Pen |
| | (400 MHz, $CDCl_3$); δ 7.40-7.36 (4H, m), 7.16-7.12 (1H, m), 7.04-7.02 (2H, m), 6.94 (1H, s), 4.20-4.15 (1H, m), 3.99-3.94 (1H, m), 3.91-3.80 (5H, m), 3.75-3.63 (6H, m), 3.58-3.48 (1H, m), 2.44-2.40 (2H, m), 2.09-2.07 (2H, m), 1.91-1.89 (4H, m), 1.71-1.69 (2H, m) | | | | | |
| 231 | 1-BOC-piperazin-4-yl | S | 2 | phenoxy | H | c-Pen |
| | (400 MHz, $CDCl_3$); δ 10.7(1H, s), 7.30-7.26 (2H, m), 7.03-6.98 (3H, m), 6.85 (1H, s), 6.62 (1H, d, J = 2.0 Hz), 6.26 (1H, d, J = 2.4 Hz), 4.82-4.77 (1H, m), 3.87 (1H, brs), 3.78-3.74 (1H, m), 3.59-3.54 (1H, m), 3.31 (4H, brs), 3.19-3.14 (1H, m), 2.48-2.35 (2H, m), 2.26 (1H, brs), 2.17 (1H, brs), 2.03-1.91 (4H, m), 1.84-1.75 (1H, m), 1.67-1.53 (4H, m), 1.45 (9H, s), 1.42-1.35 (1H, m) | | | | | |

-continued

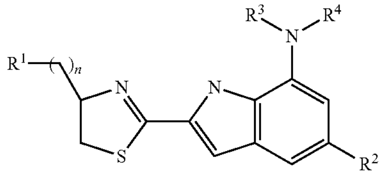

| Example | $R^1$ | * | n | $R^2$ | $R^3$ | $R^4$ |
|---|---|---|---|---|---|---|
| | | | | $H^1$ NMR data | | |
| 232 | 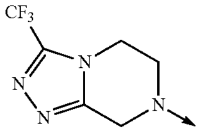 | S | 2 | phenoxy | H | c-Pen |
| | (400 MHz, $CDCl_3$); δ 10.9 (1H, brs), 7.32-7.28 (2H, m), 7.05-6.99 (3H, m), 6.90 (1H, s), 6.59 (1H, d, J = 1.6 Hz), 6.29 (1H, d, J = 2.0 Hz), 4.77-4.74 (1H, m), 4.06-3.99 (1H, m), 3.95-3.82 (4H, m), 3.62-3.57 (1H, m), 3.18-3.14 (1H, m), 2.87-2.80 (3H, m), 2.77-2.74 (1H, m), 2.00-1.98 (4H, m), 1.69 (2H, brs), 1.60-1.56 (6H, m) | | | | | |
| 233 | 2-oxopiperazin-4-yl | S | 2 | phenoxy | H | c-Pen |
| | (400 MHz, $CDCl_3$); δ 10.7 (1H, brs), 7.30-7.26 (2H, m), 7.03-7.00 (3H, m), 6.82 (1H, s), 6.60 (1H, d, J = 2.0 Hz), 3.25 (1H, d, J = 2.0 Hz), 4.74-4.71 (2H, m), 3.83 (1H, brs), 3.56-3.52 (1H, m), 3.50-3.26 (2H, m), 3.20-3.10 (2H, m), 2.68-2.61 (4H, m), 2.01-1.86 (4H, m), 1.73-1.58 (8H, m) | | | | | |
| 234 | 1-[(tetrahydrofuran-2-yl)carbonyl] piperazin-4-yl | S | 2 | phenoxy | H | c-Pen |
| | (400 MHz, $CDCl_3$); δ 10.67-10.58 (1H, m), 7.30-7.27 (2H, m), 7.04-6.98 (m, 3H), 6.85 (1H, d, J = 1.2 Hz), 6.62 (1H, d, J = 2.0 Hz), 6.27 (1H, brs), 4.84-4.78 (1H, m), 4.58-4.54 (m, 1H), 3.96-3.91 (1H, m), 3.87-3.71 (3H, m), 3.59-3.42 (3H, m), 3.19-3.14 (1H, m), 2.47-2.37 (2H, m), 2.33-2.16 (4H, m), 2.07-1.87 (6H, m), 1.83-1.75 (4H, m), 1.68-1.56 (1H, m), 1.49-1.40 (2H, m) | | | | | |
| 235 | 1-(pyridin-2-yl)piperazin-4-yl | S | 2 | phenoxy | H | c-Pen |
| | (400 MHz, $CDCl_3$); δ 10.3 (1H, s), 8.19-8.18 (1H, m), 7.49-7.45 (1H, m), 7.29-7.25 (2H, m), 7.03-6.98 (3H, m), 6.85 (1H, s), 6.64-6.60 (3H, m), 6.28 (1H, d, J = 2.4 Hz), 4.82-4.78 (1H, m), 3.79 (1H, brs), 3.60-3.55 (1H, m), 3.49-3.45 (4H, m), 3.21-3.17 (1H, m), 2.55-2.41 (6H, m), 1.99 (3H, brs), 1.88-1.86 (1H, m), 1.70 (3H, brs), 1.61-1.47 (3H, m) | | | | | |
| 236 | 1-(2-fluorophenyl) piperazin-4-yl | S | 2 | phenoxy | H | c-Pen |
| | (400 MHz, $CDCl_3$); δ 10.7 (1H, s), 7.29-7.25 (2H, m), 7.07-6.98 (5H, m), 6.95-6.88 (2H, m), 6.86 (1H, s), 6.23 (1H, d, J = 1.6 Hz), 6.28(1H, d, J = 1.6 Hz), 4.88-4.81 (1H, m), 3.89 (1H, brs), 3.60-3.56 (1H, m), 3.23-3.18 (1H, m), 2.99 (4H, brs), 2.54-2.43 (5H, m), 2.04-1.94 (3H, m), 1.98-1.82 (2H, m), 1.68-1.37 (6H, m) | | | | | |
| 237 | 2-oxopiperazin-4-yl | S | 2 | H | H | c-Pen |
| | (400 MHz, $CDCl_3$); δ 10.23 (brs, 1H), 7.00 (m, 2H), 6.89 (s, 1H), 6.48 (s, 1H), 4.72 (m, 1H), 3.92 (m, 1H), 3.54 (m, 1H), 3.38-3.11 (m, 5H), 2.73-2.58 (m, 4H), 2.11-1.96 (m, 4H), 1.74-1.55 (m, 6) | | | | | |
| 238 | (3S)-3-(amino) pyrrolidin-1-yl | S | 2 | phenoxy | H | c-Pen |
| | (400 Hz, $CDCl_3$); δ 9.97(br s, 1H), 7.32(m, 1H), 7.01-6.95(m, 6H), 6.93(m, 3H), 6.69(s, 1H), 6.34(m, 1H), 4.83(m, 1H), 3.85(m, 1H), 3.62(dd, 1H), 3.24(dd, 1H), 3.10(m, 4H), 2.58(m, 6H), 2.05(m, 3H), 1.92(m, 1H), 1.70(m, 6H), 1.53(m, 2H) | | | | | |
| 239 | 1-(acetyl)piperazin-4-yl | S | 2 | phenoxy | H | c-Pen |
| | (400 MHz, $CDCl_3$); δ 10.6 (1H, s), 7.31-7.27 (2H, m), 7.04-6.98 (3H, m), 6.84 (1H, s), 6.60 (1H, d, J = 2.0 Hz), 6.27 (1H, d, J = 1.6 Hz), 4.77-4.72 (1H, m), 4.30 (1H, brs), 3.81 (1H, brs), 3.74 (1H, brs), 3.64-3.55 (2H, m), 3.41 (1H, brs), 3.17-3.10 (2H, m), 2.89 (1H, brs), 2.68-2.63 (3H, m), 2.56-2.48 (2H, m), 2.06 (3H, s), 2.03-1.90 (4H, m), 1.72 (2H, brs), 1.60-1.56 (4H, m) | | | | | |
| 240 | (2R)-2-(aminocarbonyl) pyrrolidin-1-yl | S | 2 | methyl | H | (THP-4-yl)methyl |
| | ($CDCl_3$, 400 MHz) δ 11.31 (s, 1H), 8.18 (br, 1H), 7.24 (d, 1H), 6.83 (s, 1H), 6.75 (s, 1H), 6.22 (s, 1H), 5.50 (br, 1H), 4.71-4.64 (m, 1H), 4.07-3.99 (m, 2H), 3.57-3.38 (m, 3H), 3.28-3.25 (m, 1H), 3.19-3.06 (m, 4H), 2.88-2.81 (m, 1H), 2.75-2.70 (m, 1H), 2.49-2.41 (m, 1H), 2.39 (s, 3H) 2.25-2.12 (m, 1H), 2.08-2.04 (m, 1H), 1.99-1.95 (m, 2H), 1.83-1.80 (m, 4H), 1.53-1.40 (m, 2H) | | | | | |
| 241 | (2R)-2-(hydroxylmethyl) pyrrolidin-1-yl | S | 2 | methyl | H | (THP-4-yl)methyl |
| | ($CDCl_3$, 400 MHz) δ 10.25 (s, 1H), 6.76 (s, 1H), 6.74 (s, 1H), 6.23 (s, 1H), 4.67-4.58 (m, 2H), 4.16-4.09 (m, 1H), 4.00-3.94 (m, 2H), 3.73-3.68 (m, 1H), 3.50-3.36 (m, 2H), 3.11 (d, 2H), 2.99-2.94 (m, 2H), 2.32 (s, 3H), 2.15-2.07 (m, 2H), 2.02-1.92 (m, 3H), 1.76-1.73 (m, 2H), 1.42-1.36 (m, 2H), 1.14-1.08 (m, 2H), 0.86-0.81 (m, 2H), 0.73-0.68 (m, 2H) | | | | | |

-continued

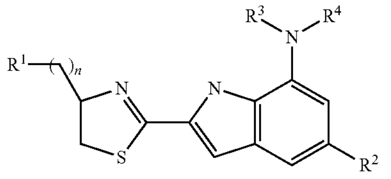

| Example | $R^1$ | * | n | $R^2$ | $R^3$ | $R^4$ |
|---|---|---|---|---|---|---|
| | | | | $H^1$ NMR data | | |
| 242 | (3R)-3-(acetylamino) pyrrolidin-1-yl | S | 2 | phenoxy | H | c-Pen |
| | (500 Hz, $CDCl_3$); δ 11.45(br s, 1H), 8.14(br s, 1H), 6.90(s, 1H), 6.77(s, 1H), 6.37(s, 1H), 4.83(m, 1H), 4.66(m, 1H), 4.05(m, 1H), 3.91(m, 1H), 3.77(m, 1H), 3.62-3.52(m, 2H), 3.13(m, 1H), 3.08-3.00(m, 2H), 2.84(m, 1H), 2.43(m, 1H), 2.23(m, 1H), 2.05(m, 4H), 2.00(s, 3H), 1.80(m, 2H), 1.71(m, 2H), 1.63(m, 2H) | | | | | |
| 243 | 4-(benzyl)piperazin-1-yl | S | 2 | phenoxy | H | c-Pen |
| | (500 Hz, $CDCl_3$); δ 7.32-7.24(m, 7H), 7.01(m, 3H), 6.77(s, 1H), 6.59(s, 1H), 6.29(s, 1H), 4.71(m, 1H), 3.87(m, 1H), 3.56(dd, 1H), 3.50(s, 2H), 3.08(dd, 1H), 2.80(br s, 8H), 2.60(br s, 2H), 2.11-1.99(m, 4H), 1.80(m, 2H), 1.71(m, 2H), 1.61(m, 2H) | | | | | |
| 244 | 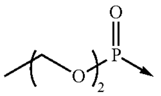 | S | 2 | methyl | H | (THP-4-yl)methyl |
| | (400 MHz, $CDCl_3$); δ 10.08(s, 1H), 6.82(s, 1H), 6.80(s, 1H), 6.29(s, 1H), 4.66(s, 1H), 4.10-3.90(m, 6H), 3.52(dd, 1H), 3.40(m, 2H), 3.10(m, 2H), 2.39(s, 3H), 2.10-1.95(m, 3H), 2.95-2.85(m, 2H), 2.72(d, 2H), 1.42-1.30(m, 2H), 1.25(q, 6H) | | | | | |
| 245 | morpholin-4-yl | S | 2 | methyl | H | (THP-4-yl)methyl |
| | (500 MHz, $CDCl_3$); δ 11.13 (s, 1H), 6.84 (s, 1H), 6.81 (s, 1H), 6.24 (s, 1H), 4.81-4.78 (m, 1H), 3.87 (d, 2H), 3.60-3.46 (m, 5H), 3.35-3.30 (m, 2H), 3.19-3.17 (m, 1H), 3.01 (br, 2H), 2.38-2.36 (m, 7H), 2.14 (br, 2H), 1.91-1.88 (m, 1H), 1.75-1.71 (m, 2H), 1.28-1.21 (m, 2H) | | | | | |
| 246 | pyrrolidin-1-yl | R | 2 | phenoxy | H | c-Pen |
| | (500 MHz, $CDCl_3$); δ 7.26-7.23 (2H, m), 6.98-6.95 (1H, m), 6.91-6.90 (2H, m), 6.74 (1H, s), 6.46-6.45 (1H, m), 6.12 (1H, brs), 4.60-4.58 (1H, m), 3.82-3.80 (2H, m), 3.60-3.50 (2H, m), 3.33-3.28 (5H, m), 3.14-3.10 (1H, m), 2.14-2.03 (6H, m), 2.00-1.94 (2H, m), 1.78 (2H, brs), 1.66-1.60 (4H, m) | | | | | |
| 247 | morpholin-4-yl | S | 2 | phenoxy | H | (THP-4-yl)methyl |
| | (400 MHz, $CDCl_3$); δ 10.19 (brs, 1H), 7.29 (m, 2H), 7.01(m, 3H), 6.84(d, 1H), 6.65(d, 1H), 6.27(d, 1H), 4.77(m, 1H), 3.93(m, 2H), 3.83(m, 1H), 3.63-3.55(m, 6H), 3.35(m, 6H), 3.19(m, 1H), 3.04(m, 2H), 2.46 (m, 2H), 2.34(m, 4H), 2.00(m, 1H), 1.83(m, 2H), 1.60(m, 2H), 1.30(m, 2H) | | | | | |
| 248 | 2-oxopiperazin-4-yl | S | 2 | phenoxy | H | (THP-4-yl)methyl |
| | (400 MHz, $CDCl_3$); δ 10.7 (brs, 1H), 7.28 (m, 2H), 7.00(m, 3H), 6.85(brs, 1H), 6.81(d, 1H), 6.60(d, J = 1.6 Hz, 1H), 6.20(d, J = 2.0 Hz, 1H), 5.03(m, 1H), 4.70(m, 1H), 3.98(m, 2H), 3.56(m, 1H), 3.49-3.36(m, 6H), 3.15-3.06(m, 4H), 2.80 (m, 1H), 2.71(m, 3H), 1.95-1.91(m, 3H), 1.72(m, 2H), 1.42(m, 2H). | | | | | |
| 249 | pyrrolidin-1-yl | S | 2 | phenoxy | H | c-Pen |
| | (500 MHz, $CDCl_3$); δ 7.31-7.27 (2H, m), 7.03-7.00 (1H, m), 6.96-6.94 (2H, m), 6.50 (1H, d, J = 2.0 Hz), 6.17 (1H, d, J = 2.0 Hz), 4.73-4.66 (1H, m), 3.86 (brs, 1H), 3.74-3.58 (2H, m), 3.46-3.37 (4, m), 3.23-3.19 (1H, m), 2.24-2.10 (6, m), 2.10-1.80 (2H, m), 1.70-1.65 (5H m) | | | | | |
| 250 | 2-oxopiperazin-4-yl | S | 2 | methyl | H | 4,4-difluorocyclohexane |
| | (400 MHz, $CDCl_3$); δ 10.14 (brs, 1H), 6.82 (s, 1H), 6.80 (s, 1H), 6.31 (s, 1H), 4.65 (m, 1H), 3.54 (m, 1H), 3.53 (dd, J = 8 Hz, 1H), 3.39 (m, 2H), 3.30 (m, 1H), 3.22-3.08 (m, 4H), 2.78-2.65 (m, 4H), 2.38 (s, 3H), 2.28-2.04 (m, 4H), 1.96-1.86 (m, 2H), 1.73 (m, 2H) | | | | | |
| 251 | morpholin-4-yl | S | 2 | methyl | H | 4,4-difluorocyclohexane |
| | (400 MHz, $CDCl_3$); δ 9.67 (brs, 1H), 6.87(s, 1H), 6.82(s, 1H), 6.34 (s, 1H), 4.71 (m, 1H), 3.65(m, 6H), 3.55 (dd, J = 8 Hz, 1H), 3.51(m, 1H), 3.15(dd, J = 8 Hz, 1H), 2.52-2.29(m, 9H), 2.15-2.04(m, 4H), 1.96-1.90(m, 2H), 1.58-1.51(m, 2H) | | | | | |
| 252 | 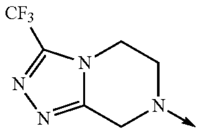 | S | 2 | methyl | H | (THP-4-yl)methyl |
| | (500 MHz, $CDCl_3$); δ 9.47(br s, 1H), 6.88(s, 1H), 6.47(s, 1H), 6.39(s, 1H), 5.87(br s, 1H), 4.12-4.00(m, 2H), 3.85(br s, 4H), 3.66(m, 1H), 3.58(t, 2H), 3.08(br s, 4H), 2.95(m, 1H), 2.85-2.70(m, 3H), 2.41(s, 3H), 2.10(m, 2H), 1.96(m, 2H), 1.60(m, 2H) | | | | | |
| 253 | 2-oxopiperazin-4-yl | S | 2 | methyl | H | (THP-4-yl)methyl |
| | (500 MHz, $CDCl_3$); δ 11.03(s, 1H), 8.19(br s, 1H), 6.82(s, 1H), 6.79(s, 1H), 6.31(s, | | | | | |

-continued

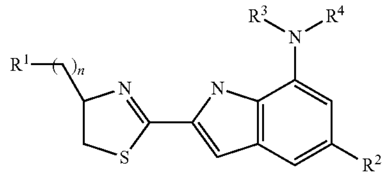

| Example | $R^1$ | * | n | $R^2$ | $R^3$ | $R^4$ |
|---|---|---|---|---|---|---|
| | $H^1$ NMR data | | | | | |
| | 1H), 4.84-4.65(m, 3H), 4.24(m, 1H), 3.91(m, 2H), 3.82-3.55(m, 4H), 3.31(m, 2H), 3.19(m, 1H), 3.14(m, 2H), 2.95(m, 2H), 2.69(m, 1H), 2.20(m, 1H), 1.98(m, 1H), 1.81(d, 2H), 1.39(m, 2H) | | | | | |
| 254 | 1-(pyridin-2-yl)piperazin-4-yl | S | 2 | chloro | H | THP-4-yl |
| | (400 MHz, $CDCl_3$); δ 9.71 (brs, 1H), 8.17 (s, 1H), 7.47 (m, 1H), 7.03 (s, 1H), 6.82 (s, 1H), 6.62 (m, 1H), 6.45 (s, 1H), 4.73 (m, 1H), 4.01 (m, 2H), 3.61-3.49 (m, 8H), 3.20 (m, 1H), 2.69-2.50 (m, 6H), 2.11-2.01 (m, 3H), 1.92 (m, 1H), 1.52 (m, 2H) | | | | | |
| 255 | 1-[(tetrahydrofuran-2-yl)carbonyl] piperazin-4-yl | S | 2 | chloro | H | THP-4-yl |
| | (400 MHz, $CDCl_3$); δ 9.89 (brs, 1H), 7.02 (s, 1H), 6.82 (s, 1H), 6.45 (s, 1H), 4.73 (m, 1H), 4.57 (m, 1H), 4.01 (m, 2H), 3.94 (m, 1H), 3.85 (m, 1H), 3.78-3.49 (m, 8H), 3.15 (m, 2H), 2.64-2.21 (m, 7H), 2.11-1.81 (m, 7H), 1.48 (m, 1H) | | | | | |
| 256 | 2-oxopiperazin-4-yl | R | 2 | methoxy | H | THP-4-yl |
| | (400 MHz, $CDCl_3$); δ 10.75(br s, 1H), 7.02(br s, 1H), 6.83(s, 1H), 6.41(s, 1H), 6.14(s, 1H), 4.70(m, 1H), 4.01(d, J = 12 Hz, 2H), 3.58(s, 3H), 3.54(m, 4H), 3.11~3.36(m, 5H), 2.66(m, 4H), 2.12(m, 2H), 1.97(m, 1H), 1.88(m, 1H), 1.56(m, 2H) | | | | | |
| 257 | 1-(hydroxymethylcarbonyl) piperazin-4-yl | R | 2 | methoxy | H | THP-4-yl |
| | (400 MHz, $CDCl_3$); δ 11.13(br s, 1H), 6.91(s, 1H), 6.47(s, 1H), 6.17(s, 1H), 4.86(m, 1H), 4.13(m, 2H), 3.97(m, 3H), 3.84(m, 3H), 3.62(m, 2H), 3.47(m, 4H), 3.03(m, 3H), 2.43(m, 3H), 2.17(m, 5H), 1.98(m, 3H), 1.44(m, 2H) | | | | | |

Example 258

[(R)-2-(5-aminomethyl-7-cyclopentylamino-1H-indol-2-yl)-4,5-dihydro-thiazol-4-yl]-methanol 2-[7-Cyclopentylamino-2((R)-4-hydroxymethyl-4,5-dihydro-thiazol-2-yl)-1H -indol-5-ylmethyl]-isoindol-1,3-dione (27 mg, 0.07 mmol) prepared in Example 64 was dissolved in ethanol (3 mL). Hydrazine hydrate (0.6 mL, 0.11 mmol) was added thereto, and the mixture was stirred for 3 h at 80° C. After completion of the reaction, the reaction mixture was distilled under reduced pressure, and purified by column chromatography to give the title compound (7 mg, Yield 37%).

$^1$H-NMR (500 HMz, $CDCl_3$); δ 10.50(brs, 1H), 6.98(s, 1H), 6.88(s, 1H), 6.46(s, 1H), 4.72(m, 1H), 4.40(m, 1H), 3.86(s, 2H), 3.81(m, 1H), 3.70(m, 1H), 3.44(m, 2H), 1.97(m, 2H), 1.59(m, 4H), 1.41(m, 2H)

Example 259

Furan-2-carboxylic acid [7-cyclopentylamino-2-((R)-4-hydroxymethyl-4,5-dihydro-thiazol-2-yl)-1H-indol-5-ylmethyl]-amide

[(R)-2-(5-aminomethyl-7-cyclopentylamino-1H-indol-2-yl)-4,5-dihydro-thiazol-4-yl]-methanol prepared in Example 258 and furan-2-carboxylic acid were reacted according to the same procedure as Step B of Preparation 101 to give the title compound.

$^1$H-NMR ($CDCl_3$); δ□11.01(1H, br), 7.38(1H, s), 7.12 (1H, d, J=3.7 Hz), 7.03(1H, s), 6.90(1H, s), 6.58(1H, br), 6.49~6.45(2H, m), 4.76~4.67(1H, m), 4.60(2H, d, J=5.5 Hz), 4.06~4.01(1H, m), 3.80~3.73(1H, m), 3.70~3.64(1H, m), 3.52~3.46(1H, m), 3.45~3.38(1H, m), 1.99~1.86(2H, m), 1.62~1.46(4H, m), 1.41~1.32(1H, m), 1.32~1.24(1H, m)

Example 260

[(R)-2-(7-cyclopentylamino-1H-indol-2-yl)-4,5-dihydro-thiazol-4-ylmethoxy]-acetic acid methyl ester

[(R)-2-(7-cyclopentylamino-1H-indol-2-yl)-4,5-dihydro-1,3-thiazol-4-yl]-methanol prepared in Example 2 and bromoethyl acetate were reacted according to the same procedure as Step B of Preparation 29 to give the title compound.

$^1$H-NMR (400 MHz, $CDCl_3$); δ 10.16(br s, 1H), 6.87(s, 1H), 6.66(dd, J=2.4, 9.2 Hz, 1H), 6.30(dd, J=2.4, 11.8 Hz, 1H), 4.94(m, 1H), 4.25(q, 2H), 4.13(d, J=5.6 Hz, 2H), 3.87 (m, 1H), 3.76(d, J=6.4 Hz, 2H), 3.56(m, 1H), 3.44(m, 1H), 2.07(m, 2H), 1.67(m, 4H), 1.51(m, 2H), 1.30(t, 3H)

Example 261

[(R)-2-(7-cyclopentylamino-1H-indol-2-yl)-4,5-dihydro-thiazol-4-ylmethoxy]-acetic acid

[(R)-2-(7-cyclopentylamino-1H-indol-2-yl)-4,5-dihydro-thiazol-4-ylmethoxy]-acetic acid methyl ester prepared in Example 260 was reacted according to the same procedure as Step A of Preparation 101 to give the title compound.

$^1$H-NMR (400 MHz, DMSO-$d_6$); δ 12.70(br s, 1H), 7.07(s, 1H), 6.57(d, J=8.8 Hz, 1H), 6.23(d, J=12 Hz, 1H), 5.13(m, 1H), 4.34(m, 1H), 4.07(m, 2H), 3.89(m, 1H), 3.63(m, 3H), 2.03(m, 2H), 1.58(m, 6H)

Example 262

Cyclopentyl-{2-[(R)-4-(3-cyclopentyl-[1,2,4]oxadiazol-5-ylmethyl)-4,5-dihydro-thiazol-2-yl]-1H-indol-7-yl}-amine

[(7-Cyclopentylamino-1H-indol-2-yl)-4,5-dihydro-thiazol-4-yl]acetic acid (140 mg, 0.41 mmol) prepared in Example 75 was dissolved in N,N-dimethylformamide (5 mL). 1,1'-Dicarbonyldiimidazole (73 mg, 0.45 mmol) was added thereto, and the mixture was stirred for 30 min at room temperature. N-hydroxy-cyclopentanecarboxamidine (260 mg, 2.03 mmol) was added thereto, and the mixture was stirred for 5 h at 80° C. After completion of the reaction, water was added. The reaction mixture was extracted with ethyl acetate, dried over anhydrous magnesium sulfate, and filtered. The filtrate was distilled under reduced pressure, and the residue was purified by column chromatography to give the title compound (100 mg, Yield 56%).

$^1$H-NMR (400 HMz, $CDCl_3$); δ 10.62(br s, 1H), 7.04(d, 1H), 6.97(t, 1H), 6.92(d, 1H), 6.49(d, 1H), 5.20(m, 1H), 3.83(m, 2H), 3.64(m, 1H), 3.39(m, 1H), 3.31(m, 1H), 3.17(m, 1H), 3.01(m, 1H), 1.97(m, 4H), 1.73(m, 4H), 1.60(m, 6H), 1.46(m, 2H), 1.34(m, 2H)

Example 263

Cyclopentyl-{2-[(R)-4-(3-piperidin-1-yl-[1,2,4]oxadiazol-5-ylmethyl)-4,5-dihydro-thiazol-2-yl]-1H-indol-7-yl}-amine

[(7-Cyclopentylamino-1H-indol-2-yl)-4,5-dihydro-thiazol-4-yl]acetic acid prepared in Example 75 and N-hydroxypiperidinecarboxamidine were reacted according to the same procedure as Example 262 to give the title compound.

$^1$H-NMR (400 HMz, $CDCl_3$); δ 10.56(br s, 1H), 7.01(d, 1H), 6.96(t, 1H), 6.90(d, 1H), 6.46(d, 1H), 5.23(m, 1H), 3.83(m, 2H), 3.64(m, 1H), 3.36(m, 1H), 3.31(m, 1H), 3.17(m, 2H), 3.01(m, 1H), 1.95(m, 2H), 1.68-1.43(m, 11H), 1.35(m, 1H)

Experimental Example 1

Measurements and Analysis of the Example Compounds for the Hepatocyte Protective Effect Against the Substances Deriving Hepatocyte Toxicity Various endogenous/exogenous attacks on the cells trigger the mechanisms of cell death which is broadly classified into two types, i.e. apoptosis or necrosis. Using these cell death mechanisms, in the present experimental example, primary hepatocytes isolated from rats were treated with drugs which were clinically shown to result in serious side-effects of hepatocyte toxicity or various chemicals which derive cell death, and the compounds synthesized in the Examples were estimated for their hepatocyte protective effects, after 24-48 h. The substances used to derive hepatocyte death include $CCl_4$, ActD, $H_2O_2$, doxorubicin, anti-Fas Ab/Actinomycin D, acetaminophen, EtOH, $CdCl_2$, palmitate, stearate, cyclophosphamide, terfenadine, diclofenac, simvastatin, and adefovir. Primary hepatocytes were isolated using the method of Seglen PO (Experimental Cell Research 74 (1972) pp 450~454). Briefly, hepatocytes were isolated according to the two-step collagenase perfusion method, and dead cells were removed by low speed (500 rpm) centrifugation for 10 min using percoll gradient (Kreamer BL etc, In Vitro Cellular & Developmental Biology 22 (1986) pp 201~211). During this step, the viability of cells was maintained 90% or above. The cells were suspended in HepatoZYME media (Gibco BRL), and the number of cells was counted. 1.5×10$^4$ cells in 100 μl were placed into the collagen-coated 96-well plate (BD biocoat), and adhered on the bottom for 3-4 h.

In order to assess the hepatocyte protective effect, above adhered cells were pretreated with the Example compounds for 30 min. At this time, the concentration of the Example compounds were serially diluted by 2-fold or 3-fold over 5 steps starting from 30 uM, 10 uM or 1 uM depending on the experiments, and the final concentration of DMSO was adjusted to 0.2%. 30 min after the treatment by compounds, cells were treated by the substances deriving hepatocyte death or hepatotoxic drugs at the concentrations indicated in Table 1. After 24-48 h, the viability of cells was determined to estimate the hepatocyte protective effects. The viability of cells was determined using WST-1 (MK-400, Takeda) method by the absorbance at 440 nm. Hepatocyte protective effects of the Example compounds were represented by "$EC_{50}$" which was calculated from measured values. "$EC_{50}$," herein means the concentration of the compound at which 50% of maximum protective effect is observed in the experiment.

Preferably, $EC_{50}$ of the Example compound is 30 uM or less, more preferably, 10 uM or less, and especially preferably, 1.0 uM or less.

Table 1 shows the treatment concentrations of various substances deriving hepatotoxity and the hepatocyte protective effect of the compound of Example 4. Table 2 shows the hepatocyte protective effects of the Example compounds against a substance which results in hepatotoxicity, doxorubicin.

TABLE 1

Cell protective effect of the compound of Example 4 against the substances deriving hepatotoxicity

| Substances deriving hepatocyte toxicity | Treatment concentration | $EC_{50}$ (μM) | Note on the substances deriving hepatocyte toxicity |
|---|---|---|---|
| Terfenadine | 10 μM | 0.4 | Anti-allergic drug |
| Simvastatin | 16 μM | <10 uM | Lipid-lowering drug |
| Diclofenac | 350 μM | 40% viability at 3-100 uM | Nonsteroidal anti-inflammatory drug (NSAID) |
| Adefovir | 100 μM | 50% viability at 3-30 uM | Anti-viral drug |

TABLE 2

Cell protective effects against doxorubicin in hepatocytes

| Example | $EC_{50}$, uM |
|---|---|
| 1 | >1 |
| 2 | 0.1 |
| 4 | 0.3 |
| 6 | 4.93 |
| 7 | 1.17 |
| 8 | 0.41 |
| 9 | >2 |
| 10 | 0.6 |
| 11 | 2.8 |
| 12 | 3.25 |
| 13 | 1.13 |
| 14 | 0.19 |
| 15 | 0.6 |

TABLE 2-continued

Cell protective effects against doxorubicin in hepatocytes

| Example | $EC_{50}$, uM |
|---|---|
| 16 | 1.29 |
| 17 | 0.315 |
| 18 | 2.42 |
| 19 | 0.35 |
| 20 | 5.77 |
| 21 | 0.3 |
| 22 | 0.25 |
| 23 | 0.14 |
| 24 | 0.13 |
| 25 | 0.76 |
| 26 | 0.2 |
| 32 | 2.12 |
| 33 | 4.04 |
| 34 | 5.58 |
| 38 | 2.0 |
| 40 | 15.58 |
| 43 | 1~10 |
| 45 | 1.32 |
| 46 | 0.4 |
| 47 | 0.36 |
| 48 | 0.2 |
| 50 | 0.25 |
| 51 | 0.6 |
| 52 | 0.75 |
| 61 | 0.78 |
| 62 | 3.77 |
| 64 | 0.54 |
| 67 | >1 |
| 68 | 0.49 |
| 71 | 1.1 |
| 78 | 29.44 |
| 83 | 0.6 |
| 84 | 1.6 |
| 85 | 0.4 |
| 88 | 1.87 |
| 90 | 7.92 |
| 93 | 0.55 |
| 94 | 28.14 |
| 97 | 4.1 |
| 101 | 1~10 |
| 108 | <0.5 |
| 109 | 0.61 |
| 115 | <1 |
| 117 | <0.5 |
| 118 | 0.41 |
| 119 | 0.17 |
| 120 | 1.12 |
| 121 | 0.47 |
| 122 | 0.96 |
| 127 | 1.18 |
| 128 | 0.2 |
| 130 | 0.1 |
| 133 | 0.31 |
| 134 | 0.51 |
| 135 | 1.26 |
| 158 | 0.91 |
| 173 | 1.98 |
| 176 | >1 |
| 177 | >1 |
| 178 | 0.23 |
| 182 | 0.375 |
| 184 | 0.18 |
| 193 | 0.65 |
| 201 | 0.33 |
| 205 | 0.34 |
| 218 | 0.26 |
| 222 | 0.18 |
| 228 | 0.13 |
| 229 | 0.25 |
| 230 | >0.32 |
| 231 | 0.2 |
| 232 | 0.24 |
| 233 | 0.27 |
| 234 | 0.09 |
| 235 | >0.54 |
| 236 | 0.16 |
| 237 | 0.2 |
| 238 | 0.33 |
| 239 | 0.83 |
| 240 | 0.28 |
| 241 | 0.21 |
| 244 | 0.195 |
| 246 | 0.35 |
| 247 | 0.86 |
| 249 | 0.11 |
| 250 | 0.09 |
| 251 | 0.3 |
| 252 | 0.51 |
| 253 | 0.2 |
| 254 | 1.0 |
| 257 | <0.4 |

Experimental Example 2

Protective Effects when tBHP (Tert-Butyl Hydroxy Peroxide; t-BuOOH) was Treated on Hepatocytes and Other Cells Derived from Various Tissues 1) Protective Effect when tBHP was Treated on Primary Hepatocytes Hepatocytes were isolated according to the same procedure as Experimental Example 1, suspended in DMEM (Gibco+10% FBS+1× antibiotics) media, and distributed to the plate. After 24 h from the distribution of hepatocytes, the compounds were serially diluted by 3-fold to the final concentration of 30, 10, 3, 1, 0.3, 0.1 uM, by which the cells were pretreated for 30 min. Cells were treated with tBHP at the final concentration of 300 uM, and the protective effects were determined after 1 h. As in Experimental Example 1, after the treatment with WST-1 (Takeda, 10 uL) for 1.5 h, $EC_{50}$ values were calculated by absorbance measurements at 440 nm using SpectraMax (Molecular Device).

Preferably, $EC_{50}$ of the Example compound is 30 uM or less, more preferably, 10 uM or less, and especially preferably, 1.0 uM or less.

2) Protective Effect when tBHP was Treated on Pancreatic Cells (Linm5F)

In order to determine the protective effect on pancreatic cells, Linm5F cells, a sort of the beta cells, were distributed into the 96-well plate in the amount of $2\times10^4$ cells/well, and incubated for 24 h. The Example compounds were serially diluted by 3-fold to the final concentration of 30, 10, 3, 1, 0.3, 0.1 uM, by which each well was treated for 1 h. Cells were treated with tBHP at the final concentration of 400 uM, and further incubated for 5 h. Protective effects were determined using SRB (Sulforhodamine B Protein) method in which total amount of cellular protein is stained. Briefly, cells were incubated for 5 h, 50 uL of 4% formaldehyde solution was added to each well to fix the cells, and stored for about 30 min at room temperature. After discarding the media, each well was washed with distilled water 2-3 times, and the plate was dried in an oven at 50° C. 50 uL of SRB solution was added to each well, and placed for about 30 min at room temperature. After removing SRB solution, the plate was washed with 1% acetic acid solution 2-3 times. After drying the plate in an oven at 50° C., 100 uL of 10 mM Tris was added to elute SRB which was staining the intracellular protein. Absorbance was measured at 590 nm and 650 nm using SpectrMax, and the absorbance at 650 nm was subtracted from the absorbance at 590 nm to calculate $EC_{50}$ value.

Preferably, $EC_{50}$, of the Example compound is 30 uM or less, more preferably, 10 uM or less, and especially preferably, 1.0 uM or less. Representatively, $EC_{50}$ of the compound of Example 14 was 0.15 uM, and that of the compound of Example 22 was 0.20 uM.

3) Protective Effect when tBHP was Treated on Cardiac Cells (H9C2, White Rat Cardiomyocyte)

In order to assess the protective effect on cardiac cells, H9C2 cells were distributed in the amount of $1.5\times10^4$ cells/well, and incubated for 24 h. The Example compounds were serially diluted by 3-fold to the final concentration of 30, 10, 3, 1, 0.3, 0.1 uM, by which each well was treated for 45 min. Cells were treated with tBHP at the final concentration of 400 uM, and incubated for 2 h. Protective effect of each compound was determined using the same SRB method as in Linm5F of above mentioned 2).

Preferably, $EC_{50}$ of the Example compound is 30 uM or less, more preferably, 10 uM or less, and especially preferably, 1.0 uM or less. $EC_{50}$ values of the representative Example compounds were as follows: Example 22: 0.17 uM, and Example 85: 0.7 uM.

4) Protective Effect when tBHP was Treated on Kidney Cells (LLC-PK1)

In order to determine the protective effect on kidney cells, $4\times10^4$ cells were distributed into each well, and incubated for 24 h. Cells were treated with the Example compounds at the final concentration of 30, 10, 3, 1, 0.3, 0.1 uM, and incubated for 30 min. Cells were treated with 400 uM tBHP, and further incubated for 6 h. Protective effect of each compound was determined using the same SRB method as in Linm5F of above mentioned 2).

Preferably, $EC_{50}$ of the Example compound is 30 uM or less, more preferably, 10 uM or less, and especially preferably, 1.0 uM or less.

5) Protective Effect when tBHP was Treated on Chondrocytes

In order to determine the protective effect on chondrocytes, chondrocytes were isolated from 2 hind legs of 16 week-old SD rats (body weight: 450-460 g). Isolation method is as follows. Cartilage isolated from the knee regions of rat hind legs was transferred to a 100 pi plate containing PBS (+1× antibiotics). PBS was maintained 4° C. in an ice-bath. PBS was exchanged with fresh one, and centrifuged at 1000 rpm. After removal of PBS, 3 mL of 1× trypsin (Gibco) at the temperature of 37° C. was added and followed by the treatment for 15 min. Supernatant was discarded after centrifugation, and washed again with PBS. Supernatant was discarded after centrifugation. After the addition of 0.2% collagenase (Worthington, type II) thereto, the cells were isolated by the overnight incubation in a rotating 37° C. incubator. Filtered cell solution was centrifuged, and the supernatant was discarded. Following the washing with PBS, cells were suspended in 10 mL of DMEM/F-12 (Gibco, 10% FBS). $2\times10^4$ cells were distributed to each well, and incubated for 24 h. The Example compounds were serially diluted by 3-fold to the final concentration of 30, 10, 3, 1, 0.3, 0.1 uM, by which each well was treated for 1 h. Cells were treated with tBHP at the final concentration of 500 uM, and incubated for 3 h. Protective effect of each compound was determined using the same SRB staining method as in Linm5F of above mentioned 2).

Preferably, $EC_{50}$ of the Example compound is 30 uM or less, more preferably, 10 uM or less, and especially preferably, 1.0 uM or less.

6) Protective Effect when tBHP was Treated on Brain Cells (SK-N-MC)

In order to assess the protective effect on brain cells, $2\times10^4$ brain cells were distributed into the 96-well plate using DMEM media (Gibco, 10% FBS), and incubated for 24 h. The Example compounds were serially diluted by 3-fold to the final concentration of 30, 10, 3, 1, 0.3, 0.1 uM, by which each well was treated for 1 h.

Cells were treated with tBHP at the final concentration of 400 uM, and incubated for 6 h. 50 uL of media was taken from each well to proceed with LDH assay (Promega). In LDH assay, 50 uL of media was mixed with 50 uL of assay solution. After the reaction for 30 min at room temperature, absorbance was measured at 490 nm using SpectraMax (Molecular Device).

Preferably, $EC_{50}$ of the Example compound is 30 uM or less, more preferably, 10 uM or less, and especially preferably, 1.0 uM or less. Representatively, the compound of Example 4, for example, showed an excellent activity in the present experiment, and its $EC_{50}$ value was 0.1 uM or less.

[Industrial Applicability]

As is demonstrated in above results, the novel compounds according to the present invention not only exhibit the effects for hepatoprotection and hepatic functional improvement, but also can be useful for the prevention and treatment of the chronic hepatic diseases such as fatty liver, hepatic fibrosis, hepatocirrhosis, etc. and acute/chronic hepatic diseases such as hepatitis, etc. caused by virus or drugs. The compounds of the present invention also exhibit the necrosis inhibitory efficacy in the cells from pancreas, kidney, brain, cartilage, and heart.

Thus, the compounds of the present invention can be useful in the prevention and treatment of necrosis and associated diseases.

It will be within the ability of those skilled in the art, to conduct various applications and modifications without departing from the scope of the present invention.

The invention claimed is:

1. A method for the treatment of necrosis and necrosis-associated diseases comprising administering a composition which comprises an indole compound of the following formula (1), pharmaceutically acceptable salt or stereoisomer thereof as an active ingredient together with a pharmaceutically acceptable carrier or diluent to a subject in need thereof:

(1)

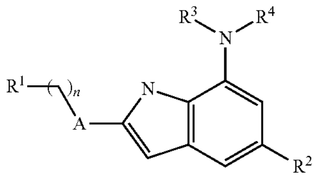

in which n denotes a number of 0 to 3,

A represents 5 membered heteroaryl or heterocycle each of which has 1 to 3 hetero atoms selected from N, O and S, $R^1$ represents $R^5$—X—B—X'—, B represents a direct bond, or represents 3~10 membered heterocycle or heteroaryl each of which has 1 to 4 hetero atoms selected from N, O and S, X and X' independently of one another represent a direct bond, or are selected from the group consisting of —$NR^6$—, —CO—, —$CONR^6$—, —$CO_2$—, —OC(O)—, —$S(O)_m$—, —O—$(CH_2)_m$—, —$(CH_2)_m$—O—, $—(CH_2)_m—$, $—NR^6CO—$, and $—NHCO_2—$, wherein m denotes a number of 0 to 3, and $R^6$ represents hydrogen or $C_1$-$C_6$-alkyl, $R^5$ represents hydrogen, hydroxy, $C_1$-$C_6$-alkyl, $C_1$-$C_6$-alkoxy, $C_4$-$C_6$-cycloalkyl or phenyl, or represents 3~10 membered monocyclic or fused cyclic heterocycle or heteroaryl each of which has 1 to 3 hetero atoms selected from N, O and S, and is optionally substituted by oxo or $C_1$-$C_6$-alkyl, $R^2$ represents $—(CR^8R^9)_p—Y—R^7$, p denotes a number of 0 to 2, $R^8$ and $R^9$ independently of one another represent hydrogen or $C_1$-$C_6$-alkyl, Y represents a direct bond, or is selected from the group consisting of —O—, $—NR^6—$, $—NR^6C(O)—$, and $—S(O)_q—$, wherein q denotes a number of 0 to 2, $R^7$ represents hydrogen, halogen, hydroxyl, $C_1$-$C_6$-alkyl, phenyl, or represents 3~10 membered heterocycle or heteroaryl each of which has 1 to 3 hetero atoms selected from N, S and O and which optionally contains oxo, $R^3$ represents hydrogen or $C_1$-$C_6$-alkyl, $R^4$ represents $C_3$-$C_6$-cycloalkyl, where alkyl, alkoxy, phenyl, cycloalkyl, heterocycle and heteroaryl may be optionally substituted, and the substituents are one or more selected from the group consisting of hydroxy, halogen, amino, $C_1$-$C_6$-alkylamino, di-$C_1$-$C_6$-alkylamino, $C_1$-$C_6$-alkyl, halo-$C_1$-$C_6$-alkyl, $C_1$-$C_6$-alkylsulfonyl, carboxy-$C_1$-$C_6$alkyl, and oxo, and wherein necrosis and necrosis-associated diseases are selected from the group consisting of neurodegenerative disease, diabetes, pancreatitis, bacterial/viral sepsis, bacterial infection, viral infection, leukemia, lymphoma, spinal cord injury, muscular dystrophy and anthrax.

2. The method of claim 1, wherein necrosis and necrosis-associated diseases are caused by drugs and toxic substances and are selected from the group consisting of the necrosis associated with alcoholism, the exposure to, or administration or self-administration of, cocaine, drugs, antibiotics, anti-cancer agent, adriamycin, puromycin, bleomycin, NSAID, cyclosporine, chemical toxins, poison gas, agrochemicals, heavy metals, or injury due to the exposure to radioactivity/UV and associated necrosis thereof.

3. The method of claim 1, wherein a prophylactic or therapeutic agent for drug-derived necrosis and necrosis-associated diseases is co-administered.

4. The method of claim 3, wherein the prophylactic or therapeutic agent for drug-derived necrosis and necrosis-associated diseases is selected from the group consisting of antibiotics, anti-cancer agents, anti-viral agents, anti-infectives, anti-inflammatory agents, anti-coagulants, lipid-improving agents, cell death inhibitors, anti-hypertensive agents, anti-diabetic/anti-obesity agents, therapeutic agents for cardiovascular disease, therapeutic agents for neurodegenerative disease, anti-aging agents and therapeutic agents for metabolic disease.

5. The method of claim 1, wherein the neurodegenerative disease is dementia, Parkinson's disease or Huntington's disease.

6. The method of claim 1, wherein the diabetes is caused by pancreatic cell destroying substances, diabetic complications or diabetic vascular disease.

7. The method of claim 6, wherein the diabetes is mediated by virus, hyperglycemia, fatty acid, diet, toxin or streptozotocin.

8. A method of preparing a composition for the treatment of necrosis and necrosis-associated diseases, which comprises mixing the compound of formula (1), a pharmaceutically acceptable salt or stereoisomer thereof as defined in claim 1 as an active ingredient together with a pharmaceutically acceptable carrier.

* * * * *